US010774062B2

(12) United States Patent
Sakai et al.

(10) Patent No.: US 10,774,062 B2
(45) Date of Patent: Sep. 15, 2020

(54) PHOTOCURING METHOD, COMPOUND AND COMPOSITION USED THEREIN

(71) Applicants: FUJIFILM Wako Pure Chemical Corporation, Osaka-shi, Osaka (JP); Tokyo University of Science Foundation, Tokyo (JP)

(72) Inventors: Nobuhiko Sakai, Saitama (JP); Kosuke Yanaba, Saitama (JP); Shigeaki Imazeki, Saitama (JP); Koji Arimitsu, Tokyo (JP)

(73) Assignees: FUJIFILM Wako Pure Chemical Corporation, Tokyo (JP); TOKYO UNIVERSITY OF SCIENCE FOUNDATION, Tokyo (JP)

(*) Notice: Subject to any disclaimer, the term of this patent is extended or adjusted under 35 U.S.C. 154(b) by 0 days.

(21) Appl. No.: 16/072,794

(22) PCT Filed: Jan. 25, 2017

(86) PCT No.: PCT/JP2017/002588
§ 371 (c)(1),
(2) Date: Jul. 25, 2018

(87) PCT Pub. No.: WO2017/131047
PCT Pub. Date: Aug. 3, 2017

(65) Prior Publication Data
US 2019/0055210 A1 Feb. 21, 2019

(30) Foreign Application Priority Data
Jan. 26, 2016 (JP) .................................. 2016-012881

(51) Int. Cl.
| | | |
|---|---|---|
| C08F 2/46 | (2006.01) |
| C08F 2/50 | (2006.01) |
| C08G 61/04 | (2006.01) |
| C07D 335/16 | (2006.01) |
| C08G 75/045 | (2016.01) |
| C07C 59/84 | (2006.01) |
| C07D 311/86 | (2006.01) |
| C08F 299/08 | (2006.01) |

(Continued)

(52) U.S. Cl.
CPC ............ *C07D 335/16* (2013.01); *C07C 59/84* (2013.01); *C07C 66/02* (2013.01); *C07C 279/26* (2013.01); *C07D 311/86* (2013.01); *C08F 2/50* (2013.01); *C08F 299/08* (2013.01); *C08G 75/045* (2013.01); *C08G 77/20* (2013.01); *C08G 77/28* (2013.01); *C07C 2603/24* (2017.05); *G03F 7/004* (2013.01)

(58) Field of Classification Search
CPC ..... C07D 335/16; C07D 311/86; C07C 66/02; C07C 2603/24; C07C 279/26; C07C 59/84; G03F 7/004; C08G 77/28; C08G 77/20; C08G 75/045; C08F 2/50; C08F 299/08

USPC .......... 522/9, 8, 7, 6, 189, 184, 71, 1; 520/1
See application file for complete search history.

(56) References Cited

U.S. PATENT DOCUMENTS

| | | |
|---|---|---|
| 4,410,716 A | 10/1983 | Hayasaka et al. |
| 5,281,620 A | 1/1994 | Denny et al. |

(Continued)

FOREIGN PATENT DOCUMENTS

| | | |
|---|---|---|
| JP | 50-28092 B | 9/1975 |
| JP | 50-28446 B | 9/1975 |

(Continued)

OTHER PUBLICATIONS

Arimitsu, JP 2009-280785 Machine Translation, Dec. 3, 2009 (Year: 2009).*

(Continued)

*Primary Examiner* — Jessica Whiteley
(74) *Attorney, Agent, or Firm* — Hamre, Schumann, Mueller & Larson, P.C.

(57) ABSTRACT

An object of the present invention is to provide a photocuring method, which makes it possible to rapidly and efficiently obtain a crosslinked product (resin), a compound used in the photocuring method, and a photocuring resin composition containing the compound.

The present invention relates to a photocuring method, which comprises a step 1 and a step 2 performed after the step 1, a compound used in the photocuring method, and a photocuring resin composition containing the compound.

Step 1: this is a step in which in the presence of (A) compound having a carbonyl group generating a radical by photoirradiation and a carboxyl group decarboxylated by photoirradiation, (B) silane coupling agent having a mercapto group or a (meth)acryl group is reacted with (C) water under acidic conditions to obtain (D) silane compound having a mercapto group or a (meth)acryl group and at least one silanol group.

Step 2: this is a step in which in the presence of the compound (A) and (E) compound having a carbonyl group generating a radical by photoirradiation and a group generating a base by being decarboxylated by photoirradiation, the compound (A) and the compound (E) are irradiated with light to create alkaline conditions in a reaction system by decarboxylating the carboxyl group of the compound (A) and generating a base from the compound (E), and radicals are generated from the compound (A) and the compound (E) to generate a crosslinked product containing a constitutional unit derived from the silane compound (D) from the silane compound (D) and, if necessary, from (F) compound having two or more polymerizable unsaturated groups.

19 Claims, No Drawings

(51) Int. Cl.

| | | |
|---|---|---|
| C07C 66/02 | (2006.01) | |
| C07C 279/26 | (2006.01) | |
| C08G 77/20 | (2006.01) | |
| C08G 77/28 | (2006.01) | |
| G03F 7/004 | (2006.01) | |

(56) References Cited

U.S. PATENT DOCUMENTS

| | | | |
|---|---|---|---|
| 2007/0066702 A1* | 3/2007 | Okazaki | C08G 75/08 522/160 |
| 2009/0286015 A1 | 11/2009 | Matsukawa et al. | |
| 2010/0215937 A1 | 8/2010 | Matsukawa et al. | |
| 2011/0097669 A1* | 4/2011 | Fukui | C08F 2/50 430/281.1 |
| 2013/0267625 A1* | 10/2013 | Noguchi | C09D 4/00 522/75 |
| 2014/0045965 A1* | 2/2014 | Noguchi | C09D 11/30 522/175 |
| 2016/0122292 A1 | 5/2016 | Sakai et al. | |
| 2016/0342084 A1 | 11/2016 | Sakai et al. | |

FOREIGN PATENT DOCUMENTS

| | | |
|---|---|---|
| JP | 56-49337 | 5/1981 |
| JP | 63-278936 | 11/1988 |
| JP | 2007-291313 | 11/2007 |
| JP | 2009-280785 * | 12/2009 |
| JP | 2010-084144 | 4/2010 |
| JP | 2011-236416 * | 11/2011 |
| JP | 2012-162639 * | 8/2012 |
| JP | 2014-015559 * | 1/2014 |
| WO | 2006/117315 | 11/2006 |
| WO | 2014/208632 | 12/2014 |
| WO | 2015/076395 | 5/2015 |

OTHER PUBLICATIONS

Arimitsu, JP 2011-236416 Machine Translation, Nov. 24, 2011 (Year: 2011).*

Takashima et al, JP 2012-162639 Machine Translation, Aug. 30, 2012 (Year: 2012).*

Takeuchi et al, JP 2014-015559 Machine Translation, Jan. 30, 2014 (Year: 2014).*

Rewcastle, et al., "Potential antitumor agents. 58. Synthesis and structure-activity relationships of substituted xanthenone-4-acetic acids active against the colon 38 tumor in vivo", Journal of Medicinal Chemistry, vol. 32 No. 4, Apr. 1, 1989, pp. 793-799.

Tomioka, et al, "Synthesis and solubility properties of C60 fullerene derivatives bearing carboxy groups", Journal of the Chemical Society, Perkin Transactions 1, No. 1, 1996, pp. 63-66.

Tanaka, et al., "Dibenzo [a, d] cycloheptenylacetic Acids", Yakugaku Zasshi—Journal of the Pharmaceutical Society of Japan, vol. 101, No. 7, 1981, pp. 614-628.

Extended European Search Report issued in corresponding European Patent Application No. 17744277.9, dated May 17, 2019, 7 pages.

Katogi, et al., Photobase Generation from Amineimide Derivatives and Their Use for Curing an Epoxide/Thiol System, J. Polym. Sci.: Part A: Pol. Chem., (2002) 40, 4045-4052.

Arimitsu, et al., "Application to Photoreactive Materials of Photochemical Generation of Superbases with High Efficiency Based on Photodecarboxylation Reactions", Chem. Mater., (2013) 25, 4461-4463.

Salmi, et al., "Quaternary ammonium salts of phenylglyoxylic acid as photobase generators for thiol-promoted epoxide photopolymerization", Polym. Chem., (2014) 5, 6577-6583.

Kesmez, et al., "Effect of amine catalysts on preparation of nanometric SiO2 particles and antireflective films via sol-gel method", J. Sol-Gel Sci. Technol., (2010) 56: 167-176.

Ishikawa, et al., "Photosensitivity Characteristics of UV Curable Organic-Inorganic Hybrids Sensitized with Benzoin Derivatives as Photobase Generators", J. Photopolym. Sci. Technol., (2014) 27(2), 223-225.

Inoue, et al., "Photo-Curing of Acryl-Functional Alkoxysilane with Benzoin Sulfonates", J. Photopolym. Sci. Technol., (1999) 12(1), 129-132.

Schreck, et al., "Hybrid Organic/Inorganic Thiol-Ene-Based Photopolymerized Networks", Macromolecules, (2011) 44, 7520-7529.

Igarashi, et al., "Thiol-Containing Polysilsesquioxane Liquid and Photocurable Sulfur-Containing Transparent Organic-Inorganic Hybrid Monoliths Obtained via Cosolvent-Free Hydrolytic Polycondensation" Bull. Chem. Soc. Jpn., (2013) 86(7), 880-883.

* cited by examiner

PHOTOCURING METHOD, COMPOUND AND COMPOSITION USED THEREIN

TECHNICAL FIELD

The present invention relates to a photocuring method for obtaining a crosslinked product, which contains a constitutional unit derived from a silane compound, and a compound and a composition which are used in the photocuring method.

BACKGROUND ART

In recent years, in the fields of photoresist, adhesion, coating, and the like, the research and development of a photocuring method for curing various resin compositions by using a photobase generator have been vigorously carried out. As a resin composition curing system using a photobase generator, a method of curing a compound having an epoxy group is known (for example, Non-Patent Literature 1). In the curing system of the compound having an epoxy group, by applying the phenomenon in which the compound having an epoxy group is cured by causing a crosslinking reaction by the action of a base, the irradiation of light (active energy rays) is performed to generate a base from a photobase generator in the resin composition comprising the compound having an epoxy group, and then a heating treatment is performed to cure the compound having an epoxy group. In addition, a method is also known in which a photobase generator generating a strong base such as amidine, guanidine, biguanide, or phosphazene, a compound having an epoxy group, and, for example, a crosslinking agent having an acidic proton such as a polyfunctional thiol are used in combination such that the compound having an epoxy group and the crosslinking agent are rapidly cured at a low temperature (for example, Patent Literature 1 and Non-Patent Literature 2 and 3).

As a resin composition curing system using a general base, a sol-gel method by the hydrolysis and the polycondensation of a silane coupling agent having alkoxysilyl groups is known. During the hydrolysis by a base, in a case where one alkoxysilyl group is hydrolyzed to become a silanol group, steric hindrance is reduced, and accordingly, the remaining alkoxysilyl groups can be easily hydrolyzed to become silanol groups. Accordingly, because the polycondensation proceeds in the presence of more silanol groups having high polarity than in a case where an acid is used, the insolubilization of gel easily occurs, and clouding and precipitation easily occur before the molecular weight increases. In a case where the silanol group and the base form a salt and are precipitated at this time, the base is driven out of the reaction system, and accordingly, a problem in that the silane coupling agent as a raw material remains occurs. Therefore, in the sol-gel method using a base, generally, a method is used in which first the silane coupling agent having alkoxysilyl groups is heated together with water or an acid catalyst is caused to act such that the alkoxysilyl groups are partially hydrolyzed and polycondensed, and then the remaining silanol groups are polycondensed by adding a base such that the silane compound is cured (Non-Patent Literature 4).

As the sol-gel method, for example, a method is known in which a silane coupling agent having alkoxysilyl groups is heated in advance by adding water thereto to prepare a resin composition comprising a silane compound in which the alkoxysilyl groups are partially hydrolyzed and polycondensed, a photobase generator is added to the resin composition, and then the resin composition is irradiated with light (active energy rays) to generate a base from the photobase generator and polycondense the remaining alkoxysilyl groups or silanol groups (for example, Patent Literature 2). Because the sol-gel method is started by heating before the irradiation of light (active energy rays), the hydrolysis and the polycondensation can be finished in a desired state. However, because heating needs to be performed for a long period of time for preparing the resin composition, and the molecular weight of the resin easily increases, the sol-gel method is unstable, and the pot life of the resin composition is easily shortened.

In addition, for example, a method is known in which a sol-gel method and photo-radical polymerization are allowed to simultaneously proceed by using a polymer obtained by partially hydrolyzing and polycondensing a silane coupling agent having a methacryl group and using a photobase generator and a photo-radical generator in combination (for example, Non-Patent Literature 5). However, because the photobase generator and the photo-radical generator described in Non-Patent Literature 5 are oil-soluble and have low affinity (solubility) with a solvent such as water or an alcohol, a solvent imposing a high environmental load such as chloroform needs to be used. In addition, because the base generated from the photobase generator is a weak base such as a primary or secondary amine, the base has a problem in that the rate of hydrolysis or polycondensation is lower than that obtained by a strong base.

Meanwhile, a method is being examined in which a photoacid generator and a photo-radical generator are used in combination to cure a silane coupling agent having an acryl group by causing a sol-gel method and photo-radical polymerization to simultaneously proceed (for example, Non-Patent Literature 6). With the method of Non-Patent Literature 6, because a low-molecular weight monomer can be handled as it is, the pot life of a resin composition is long, and a polymer having high uniformity at a molecular level can be prepared. However, the strong acid generated from the photoacid generator has a problem in that curing consumes a long time or a metal may be corroded by the acid remaining in the resin. Furthermore, in the method of Non-Patent Literature 6, the silane coupling agent is hydrolyzed by the moisture in the atmosphere, which leads to problems in that the humidity control is difficult, the reproducibility is poor, the moisture in the atmosphere cannot easily permeate the inside of the resin composition, and curing failure easily occurs.

Therefore, for photocuring a silane compound (a silane coupling agent), a method which does not use a sol-gel method performed by only using light, that is, a method is mainly used in which hydrolysis and polycondensation of alkoxysilyl groups of the silane coupling agent are finished first by using an acid, and then the silane coupling agent is subjected to general photocuring (radical polymerization between acrylate compounds, an ene-thiol reaction between an allyl compound and a thiol compound, or cationic polymerization between epoxy compounds) (for examples, Non-Patent Literature 7 and 8, and Patent Literature 3).

In addition, as a composition using hydrolysis and polycondensation of a silane coupling agent having alkoxysilyl groups, a polysiloxane-based coating composition is known (for example, Patent Literature 4 and 5). In the coating composition described in Patent Literature 4, an alkali metal thiocyanate is used for hydrolysis and polycondensation of the silane coupling agent. In addition, in the coating composition described in Patent Literature 5, instead of the alkali metal thiocyanate, for example, an alkali metal salt of an organic carboxylic acid such as sodium acetate and acetic acid are used in combination. In a case where the alkali metal salt of an organic carboxylic acid and acetic acid are used in combination, the composition at the early stage of curing is slightly acidic because the amount of acetic acid is larger than that of the alkali metal salt of an organic carboxylic acid. However, after coating, due to the volatilization of acetic acid, the ratio of the existing alkali metal salt of an organic carboxylic acid becomes relatively high, and hence the composition becomes basic. It is considered that as a result, polycondensation can occur, and the pot life can be improved.

CITATION LIST

Patent Literature

Patent Literature 1: WO2014/208632
Patent Literature 2: JP2014-15559 A
Patent Literature 3: JP2007-291313 A
Patent Literature 4: JP1975-28092 B (JP-S50-28092 B)
Patent Literature 5: JP1975-28446 B (JP-S50-28446 B)

Non-Patent Literature

Non-Patent Literature 1: J. Polym. Sci. Pol. Chem., 2002, 4045
Non-Patent Literature 2: Chem. Mater., 2013, 25, 4461-4463
Non-Patent Literature 3: Polym. Chem., 2014, 5, 6577-6583
Non-Patent Literature 4: J. Sol-Gel Sci. Technol., 2010, 56, 167-176
Non-Patent Literature 5: J. Photopolym. Sci. Tec., 2014, 27, 2, 223-225
Non-Patent Literature 6: J. Photopolym. Sci. Tec., 1999, 2, 129-132
Non-Patent Literature 7: Macromolecules 2011, 44, 7520-7529
Non-Patent Literature 8: Bull. Chem. Soc. Jpn. 2013, 86, 7, 880-883

SUMMARY OF INVENTION

Technical Problem

Under the circumstances described above, there is a demand for the development of a photocuring method which solves the problems of the curing system using a strong acid generated from a photoacid generator and makes it possible to rapidly and efficiently obtain a crosslinked product (resin) by the irradiation of light (active energy rays).

In recent years, for the curing by the irradiation of light (active energy rays), from the viewpoint of energy saving, a UV-LED lamp has been used instead of a high-pressure mercury lamp, and a photobase generator having a photosensitive region at 365 nm or 405 nm which is a main wavelength of the UV-LED lamp has been required. Meanwhile, in the field of coating material and the like, for the purpose of improving the durability of a crosslinked product (resin), a UV absorber is added in some cases. Because some of the UV absorbers absorb light (active energy rays) having a wavelength of around 100 to 365 nm, a problem occurs in which light does not reach the photobase generator and hence the photobase generator cannot sense light.

Although the coating compositions described in Patent Literature 4 and 5 use an alkali metal salt such as alkali metal thiocyanate or an alkali metal salt of an organic carboxylic acid, because the alkali metal salt is poorly soluble in an organic component, a problem occurs in which as the proportion of the organic component in the composition increases, precipitation or whitening occurs. Particularly, in a case where the composition is used for electronic materials, because the alkali metal salt remains as an impurity, a problem such as short circuit of metal wiring may occur due to the alkali metal salt. Furthermore, because the coating composition described in Patent Literature 5 uses an acidic component such as acetic acid, there are problems in that the acidic component should be removed by performing a heating treatment for a long period of time so as to prevent the acidic component from corroding a metal by remaining in the resin, and that the volatilized acidic component negatively affects the human body or the environment.

The present invention has been made in consideration of the circumstances described above and provides a photocuring method, which makes it possible to rapidly and efficiently obtain a crosslinked product (resin) by causing a sol-gel reaction and a photo-radical polymerization reaction to proceed simultaneously by using a photobase generator and a photo-radical generator in combination, a compound used in the photocuring method, and a photocuring resin composition comprising the compound.

In addition, the present invention provides a photocuring method which makes it possible to rapidly and efficiently obtain a crosslinked product (resin) by using light (active energy rays) having a main wavelength at 365 nm or 405 nm even in a case where a UV absorber coexists.

Furthermore, the present invention provides a photocuring method which makes it possible to secure a long pot life, does not easily cause the corrosion of a metal, and is suitable for polysiloxane-based coating, a compound used in the photocuring method, and a photocuring resin composition comprising the compound.

Solution to Problem

The present invention is constituted as below.

(1) A photocuring method comprising a step 1 and a step 2 performed after the step 1; wherein in the step 1, in the presence of (A) compound having a carbonyl group generating a radical by photoirradiation and a carboxyl group decarboxylated by photoirradiation, (B) silane coupling agent having a mercapto group or a (meth)acryl group is reacted with (C) water under acidic conditions to obtain (D) silane compound having a mercapto group or a (meth)acryl group and at least one silanol group, and in the step 2, in the presence of the compound (A) and (E) compound having a carbonyl group generating a radical by photoirradiation and a group generating a base by being decarboxylated by photoirradiation, the compound (A) and the compound (E) are irradiated with light to create alkaline conditions in a reaction system by decarboxylating the carboxyl group of the compound (A) and generating a base from the compound (E), and radicals are generated from the compound (A) and the compound (E) to generate a crosslinked product containing a constitutional unit derived from the silane compound (D) from the silane compound (D) and, if necessary, from (F) compound having two or more polymerizable unsaturated groups.

(2) A compound represented by a general formula [16];

general formula [16]

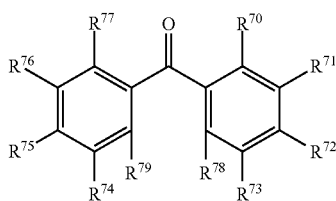

[16]

wherein $R^{70}$ to $R^{77}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], and $R^{78}$ and $R^{79}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{78}$ and $R^{79}$ are bonded to each other through an oxygen atom, a sulfur atom, or a carbonyl group, provided that at least two among the groups represented by $R^{70}$ to $R^{77}$ are groups represented by the general formula [2];

general formula [2]

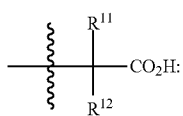

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

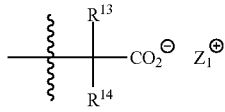

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

(3) A compound represented by a general formula [17];

general formula [17]

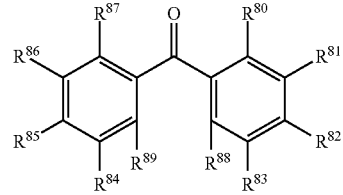

[17]

wherein $R^{80}$ to $R^{87}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], and $R^{88}$ and $R^{89}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{88}$ and $R^{89}$ are bonded to each other through an oxygen atom, a sulfur atom, or a carbonyl group, provided that at least one of the groups represented by $R^{80}$ to $R^{87}$ is the group represented by the general formula [3], and at least one of the remaining 7 groups is the group represented by the general formula [2] or the group represented by the general formula [3];

general formula [2]

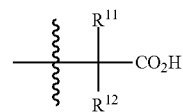

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

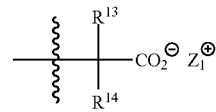

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

(4) A photocuring resin composition comprising (A) compound having a carbonyl group generating a radical by photoirradiation and a carboxyl group decarboxylated by photoirradiation, (D) silane compound having a mercapto group or a (meth)acryl group and at least one silanol group, and (E) compound having a carbonyl group generating a radical by photoirradiation and a group generating a base by being decarboxylated by photoirradiation, wherein the composition may further comprise (F) compound having two or more polymerizable unsaturated groups.

Advantageous Effects of Invention

In the photocuring method of the present invention, before and after the irradiation of light (active energy rays), the pH of the composition comprising the silane coupling agent (the silane compound) is caused to shift to an alkaline pH from an acidic pH. In this way, the hydrolysis and the polycondensation (the sol-gel process) of the alkoxysilyl groups in the silane coupling agent (the silane compound) can be efficiently performed in the same system. Furthermore, by generating a radical through the irradiation of light (active energy rays), the radical polymerization between (meth)acrylates in the silane coupling agent (the silane compound) or the ene-thiol reaction or the yne-thiol reaction between the mercapto group in the silane coupling agent (the silane compound) and the polymerizable unsaturated groups in the compound having polymerizable unsaturated groups can be efficiently performed in the same system. Accordingly, the photocuring method of the present invention makes it possible to obtain a crosslinked product (resin) containing a constitutional unit derived from the silane compound in a simple manner.

In addition, the photocuring method of the present invention is a method in which the hydrolysis of the alkoxysilyl groups in the silane coupling agent (the silane compound) is performed using a carboxylic acid, which is decarboxylated by photoirradiation, and water. Therefore, unlike in the method of the related art performed by heating, the hydrolysis does not consume a long period of time, and the photocuring method does not depend on the humidity of the environment surrounding the reaction system or the film thickness of the obtained crosslinked product (resin). In addition, because the carboxylic acid decarboxylated by the photoirradiation is decarboxylated and loses an acidic group (a carboxyl group) after being irradiated with light (active energy rays), the problem of the corrosion of a metal by an acid is reduced, and the carboxylic acid does not need to be removed from the system. Therefore, the photocuring method of the present invention using the carboxylic acid is an efficient photocuring method.

Furthermore, the photocuring method of the present invention is a method in which a sol-gel process is smoothly performed using a silane coupling agent as a raw material. Accordingly, the storage stability of the resin composition used in the photocuring method can be improved.

The compound represented by the general formula [16] of the present invention is a compound having at least two groups represented by the general formula [2] among "(A) compound having a carbonyl group generating a radical by photoirradiation and a carboxyl group decarboxylated by photoirradiation" according to the photocuring method of the present invention. That is, the compound has at least two carboxyl groups decarboxylated by photoirradiation. Accordingly, the compound is a useful compound (a photo-radical generator) which can function as an acid catalyst even being added in a small amount and can generate a radical by photoirradiation.

The compound represented by the general formula [17] of the present invention contains (1) compound having at least one group represented by the general formula [2] and at least one group represented by the general formula [3] and (2) compound having at least two groups represented by the general formula [3], among "(E) compound having a carbonyl group generating a radical by photoirradiation and a group generating a base by being decarboxylated by photoirradiation" according to the photocuring method of the present invention. Between these, (1) compound having at least one group represented by the general formula [2] and at least one group represented by the general formula [3] is a compound having at least one carboxyl group decarboxylated by photoirradiation and at least one group generating a base by being decarboxylated by photoirradiation. Accordingly, this compound is a compound having functions of both the compounds including "(A) compound having a carbonyl group generating a radical by photoirradiation and a carboxyl group decarboxylated by photoirradiation" and "(E) compound having a carbonyl group generating a radical by photoirradiation and a group generating a base by being decarboxylated by photoirradiation" according to the photocuring method of the present invention. That is, the compound (1) is a useful compound which can become "(A/E) compound having a carbonyl group generating a radical by photoirradiation, a carboxyl group decarboxylated by photoirradiation, and a group generating a base by being decarboxylated by photoirradiation". Meanwhile, (2) compound having at least two groups represented by the general formula [3] is a compound having at least two groups generating a base by being decarboxylated by photoirradiation. Therefore, the compound (2) is a useful compound (a photobase and photo-radical generator) which can function as a photobase generator by being added in a small amount and can generate a radical by photoirradiation.

The photocuring resin composition of the present invention is a composition obtained after the step 1 in the photocuring method of the present invention, that is, a composition not yet being subjected to the step 2. In a case where the composition is irradiated with light (active energy rays), the pH of the composition shifts to an alkaline pH from an acidic pH, and a radical is generated in the composition. Therefore, this composition is a useful composition which makes it possible to efficiently obtain a crosslinked product containing a constitutional unit derived from a silane compound and to secure a long pot life.

DESCRIPTION OF EMBODIMENTS

In the present invention, except for a case where the wavelength is specified, light (active energy rays) includes electromagnetic waves (visible rays) having a wavelength in a visible range and electromagnetic waves having a wavelength in a non-visible range such as electromagnetic waves (ultraviolet rays) having a wavelength in an ultraviolet range, electromagnetic waves (infrared rays) having a wavelength in an infrared range, and X-rays. In the present invention, a base generator exhibiting sensitivity with respect to light (active energy rays) (base generator generating a base by the irradiation of active energy rays) is described as a photobase generator in some cases, and a radical generator exhibiting sensitivity with respect to light (active energy rays) (radical generator generating a radical by the irradiation of active energy rays) is described as a photo-radical generator in some cases. In addition, light (active energy rays) having a wavelength of 365 nm, 405 nm, and 436 nm is described as an i-line, an h-line, and a g-line respectively in some cases.

—Photocuring Method of the Present Invention—

The photocuring method of the present invention is a method comprising the following step 1 and step 2, in which the step 2 is performed after the step 1 is performed.

Step 1: this is a step in which in the presence of (A) compound having a carbonyl group generating a radical by photoirradiation and a carboxyl group decarboxylated by photoirradiation, (B) silane coupling agent having a mercapto group or a (meth)acryl group is reacted with (C) water under acidic conditions to obtain (D) silane compound having a mercapto group or a (meth)acryl group and at least one silanol group.

Step 2: this is a step in which in the presence of the compound (A) and (E) compound having a carbonyl group generating a radical by photoirradiation and a group generating a base by being decarboxylated by photoirradiation, the compound (A) and the compound (E) are irradiated with light to create alkaline conditions in a reaction system by decarboxylating the carboxyl group of the compound (A) and generating a base from the compound (E), and radicals are generated from the compound (A) and the compound (E) to generate a crosslinked product containing a constitutional unit derived from the silane compound (D) from the silane compound (D) and, if necessary, from (F) compound having two or more polymerizable unsaturated groups.

The step 1 in the photocuring method of the present invention is a step in which the silane coupling agent (B) and (C) water are reacted with each other under acidic conditions by using the compound (A), which is a carboxylic acid, as an acid catalyst such that the alkoxysilyl groups in the silane coupling agent (B) are hydrolyzed and converted into silanol groups, thereby obtaining the silane compound (D). The step 2 in the photocuring method of the present invention is a step in which the photocuring resin composition containing the silane compound (D) obtained in the step 1, the compound (A), the compound (E), and the compound (F) used if necessary is irradiated with light (active energy rays) such that (1) the carboxyl group in the compound (A) is decarboxylated, the compound (A) loses an acidic group (a carboxyl group), a base is generated from the compound (E), the pH in the reaction system, that is, the pH in the composition shifts to an alkaline pH from an acidic pH, and hence a sol-gel reaction is caused between the silanol groups in the silane compound (D), and (2) a radical is simultaneously generated from the compound (A) and the compound (E) by the irradiation of light (active energy rays), and hence the (meth)acrylates in the silane compound (D) in the composition are radically polymerized or the mercapto group in the silane compound (D) and the polymerizable unsaturated groups in the compound (F) are reacted with each other (ene-thiol reaction or yne-thiol reaction). That is, the step 2 in the photocuring method of the present invention is a step of obtaining a crosslinked product (resin) containing a constitutional unit derived from the silane compound (D) by causing the sol-gel reaction and the radical polymerization, the ene-thiol reaction, or the yne-thiol reaction to proceed simultaneously. The photocuring method of the present invention is a method which makes it possible to efficiently obtain a crosslinked product (resin) containing a constitutional unit derived from the silane compound (D) by performing the step 1 and then performing the step 2. It should be noted that the crosslinked product (resin) mentioned herein is not limited to a crosslinked product (resin) obtained by reacting the silane compounds (D) with each other or a crosslinked product formed only of the constitutional unit derived from the silane compound (D) or the constitutional unit derived from the compound (F), and may also be a crosslinked product (resin) containing a constitutional unit other than the silane compound (D) and the compound (F).

In a case where the silane coupling agent (B) in the photocuring method of the present invention is (B') silane coupling agent having a mercapto group, the silane compound (D) is (D') silane compound having a mercapto group and at least one silanol group, and the crosslinked product in the step 2 that contains (F) compound having polymerizable unsaturated groups and is obtained using the compound (F) further contains a constitutional unit derived from the compound (F).

In a case where the silane coupling agent (B) is (B') silane coupling agent having a mercapto group, the step 1 and the step 2 are specifically as described below.

Step 1: this is a step in which in the presence of (A) compound having a carbonyl group generating a radical by photoirradiation and a carboxyl group decarboxylated by photoirradiation, (B') silane coupling agent having a mercapto group is reacted with (C) water under acidic conditions to obtain (D') silane compound having a mercapto group and at least one silanol group.

Step 2: this is a step in which in the presence of the compound (A) and (E) compound having a carbonyl group generating a radical by photoirradiation and a group generating a base by being decarboxylated by photoirradiation, the compound (A) and the compound (E) are irradiated with light to create alkaline conditions in a reaction system by decarboxylating the carboxyl group of the compound (A) and generating a base from the compound (E), and radicals are generated from the compound (A) and the compound (E) to generate a crosslinked product containing a constitutional unit derived from the silane compound (D') and a constitutional unit derived from the compound (F) from the silane compound (D') and (F) compound having two or more polymerizable unsaturated groups.

In a case where the silane coupling agent (B) is (B') silane coupling agent having a mercapto group, the step 2 is a step in which a sol-gel reaction is caused between the silanol groups in the silane compound (D'), and the mercapto group in the silane compound (D') is reacted with the polymerizable unsaturated groups in the compound (F) (ene-thiol reaction or yne-thiol reaction) in the composition by generating radicals from the compound (A) and the compound (E). That is, the step 2 in the photocuring method of the present invention is a step of obtaining a crosslinked product (resin) containing a constitutional unit derived from the silane compound (D') and a constitutional unit derived from the compound (F) by causing the sol-gel reaction and the ene-thiol reaction or the yne-thiol reaction to simultaneously proceed. It should be noted that the crosslinked product (resin) mentioned herein is not limited to a crosslinked product formed only of the constitutional unit derived from the silane compound (D') and the constitutional unit derived from the compound (F), and may also be a crosslinked product (resin) containing a constitutional unit other than the silane compound (D') and the compound (F).

In a case where the silane coupling agent (B) in the photocuring method of the present invention is (B") silane coupling agent having a (meth)acryl group, the silane compound (D) is (D") silane compound having a (meth)acryl group and at least one silanol group, and in the step 2, the crosslinked product is obtained by reacting the silane compounds (D") with each other. It should be noted that the (meth)acryl group mentioned herein means an acryl group and/or a methacryl group.

In a case where the silane coupling agent (B) is (B") silane coupling agent having a (meth)acryl group, the step 1 and the step 2 are specifically as described below.

Step 1: this is a step in which in the presence of (A) compound having a carbonyl group generating a radical by photoirradiation and a carboxyl group decarboxylated by photoirradiation, (B") silane coupling agent having a (meth) acryl group is reacted with (C) water under acidic conditions to obtain (D") silane compound having a (meth)acryl group and at least one silanol group.

Step 2: this is a step in which in the presence of the compound (A) and (E) compound having a carbonyl group generating a radical by photoirradiation and a group generating a base by being decarboxylated by photoirradiation, the compound (A) and the compound (E) are irradiated with light to create alkaline conditions in a reaction system by decarboxylating the carboxyl group of the compound (A) and generating a base from the compound (E), and radicals are generated from the compound (A) and the compound (E) to generate a crosslinked product containing a constitutional unit derived from the silane compound (D") from the silane compound (D").

In a case where the silane coupling agent (B) is (B") silane coupling agent having a (meth)acryl group, the step 2 is a step in which a sol-gel reaction is caused between the silanol groups in the silane compound (D"), and the (meth)acryl groups (acrylates) in the silane compound (D") are radically polymerized with each other in the composition by generating radicals from the compound (A) and the compound (E). That is, the step 2 in the photocuring method of the present invention is a step of obtaining a crosslinked product (resin) containing a constitutional unit derived from the silane compound (D") by causing the sol-gel reaction and the radical polymerization to simultaneously proceed. It should be noted that the crosslinked product (resin) mentioned herein is not limited to a crosslinked product (resin) obtained by reacting only the silane compounds (D") with each other. The crosslinked product may be obtained by radically polymerizing the silane compounds (D") with each other through the compound (F) having polymerizable unsaturated groups or through another general monomer component such as a crosslinking agent, and may also be a crosslinked product (resin) containing a constitutional unit derived from the compound (F) and/or a constitutional unit other than the compound (F).

The reaction system of the step 1 in the photocuring method of the present invention contains at least the compound (A), the silane coupling agent (B), and (C) water. However, considering the compatibility of (A) to (C), the workability, and the like, it is preferable that the reaction system of the step 1 further contains the compound (E). A base stays hidden in the compound (E) unless the compound is irradiated with light (active energy rays). Therefore, the compound does not negatively affect the step 1, and rather has an effect of improving the compatibility between the compound (A), the silane coupling agent (B), and (C) water. In addition, in a case where the compound (E) is incorporated into the reaction system in advance, a step of adding the compound (E) does not need to be performed between the step 1 and the step 2, and hence the workability is improved. Therefore, it is preferable that the reaction system of the step 1 further contains the compound (E).

The reaction system of the step 2 in the photocuring method of the present invention contains the silane compound (D) obtained in the step 1, the compound (A) and the compound (E), and the compound (F) which is used if necessary, and a mixture of these is referred to as a photocuring resin composition in some cases. More specifically, in a case where the silane compound (D) obtained in the step 1 is (D') silane compound having a mercapto group and at least one silanol group, the reaction system of the step 2 contains at least the silane compound (D'), the compound (A), the compound (E), and the compound (F). In a case where the silane compound (D) obtained in the step 1 is (D") silane compound having a (meth)acryl group and at least one silanol group, the reaction system of the step 2 contains at least the silane compound (D"), the compound (A), and the compound (E).

The reaction system of the step 1 may contain components other than (A) to (C) described above and (E) which is used if necessary. Examples of the components include an organic solvent, additives for imparting various other characteristics, and the like. In addition, the reaction system (photocuring resin composition) of the step 2 may contain components other than (A), (D), and (E) described above and (F) which is used if necessary. Examples of the components include an organic solvent, additives for imparting various other characteristics, and the like. The organic solvent can improve the compatibility of (A) to (F) or improve the workability by enhancing the coating properties of the composition applied to the surface of a solid such as a substrate. It should be noted that it goes without saying that the step 2 may contain (C) water used in the step 1 or the unreacted silane coupling agent (B).

The step 1 in the photocuring method of the present invention is acidic because the reaction system of the step 1 contains the compound (A). "Acidic" generally means that the pH is equal to or higher than 0 and less than 7. Particularly, the step 1 is preferably in a pH range of 3 to 5. In a case where the step 1 is performed at the preferred pH, a compound (A) (carboxylic acid) having a pKa of 3 to 5 may be used as the compound (A). In this case, it is possible to inhibit polycondensation (sol-gel process) between the silane compounds (D) in the step 1, and hence a uniform crosslinked product (resin) is easily obtained.

The step 2 in the photocuring method of the present invention is a step of causing the sol-gel reaction and the radical polymerization, the ene-thiol reaction, or the yne-thiol reaction to simultaneously proceed. A characteristic of the step 2 is that the sol-gel reaction among the above reactions is performed under alkaline conditions. The step 2 is acidic before the irradiation of light (active energy rays) is performed. However, by the irradiation of light (active energy rays), the carboxyl group in the compound (A) is decarboxylated. As a result, an acidic group (a carboxyl group) is lost, and a base is generated from the compound (E). Accordingly, the pH in the reaction system shifts to an alkaline pH, and hence alkaline conditions are created. "Alkaline" generally means that the pH is higher than 7 and equal to or lower than 14. Particularly, the step 2 is preferably in a pH range of 8 to 14. In a case where the step 2 is performed at the preferred pH, the compound (E) which can generate a base with a pH of 8 to 14 may be used. In this case, the sol-gel process in the step 2 smoothly proceeds, and hence a uniform crosslinked product (resin) is easily obtained.

The reaction between the silane coupling agent (B) and (C) water in the step 1 in the photocuring method of the present invention may or may not be completed. However, it is preferable that the reaction is not completed. In other words, although the step 1 is a hydrolysis reaction of the alkoxysilyl groups in the silane coupling agent (B), the alkoxysilyl groups may be partially hydrolyzed such that only some of the alkoxysilyl groups are converted into silanol groups, or the alkoxysilyl groups may be totally hydrolyzed such that all the alkoxysilyl groups are converted into silanol groups. Particularly, it is preferable that the alkoxysilyl groups are partially hydrolyzed such that only some of the alkoxysilyl groups are converted into silanol groups. It is preferable that the step 1 is finished in a state where only some of the alkoxysilyl groups are converted into silanol groups, that is, at the stage where the alkoxysilyl groups are not totally hydrolyzed but partially hydrolyzed, because then the polycondensation (the sol-gel process) between the silane compounds (D) in the step 1 can be inhibited, and hence a uniform crosslinked product (resin) is easily obtained. It should be noted that whether only some of the alkoxysilyl groups are converted into silanol groups or all of the alkoxysilyl groups are converted into silanol groups can be controlled by the number of equivalent of water with respect to the silane coupling agent (B), the reaction time, and the like. It should be noted that "alkoxysilyl groups are partially hydrolyzed" means that generally 10% to 90% and preferably 30% to 70% of alkoxysilyl groups in all of the alkoxysilyl groups are hydrolyzed.

The compound (A) and the compound (E) in the step 2 in the photocuring method of the present invention are compounds exhibiting sensitivity with respect to light. More specifically, the compound (A) is a compound which exhibits sensitivity with respect to light (active energy rays) generally having a wavelength of 100 to 780 nm, preferably having a wavelength of 200 to 450 nm, and more preferably having a wavelength of 350 to 450 nm, generates a radical from the carbonyl group in the compound (A) by absorbing the light (active energy rays), and loses the acidic group (the carboxyl group) by the decarboxylation of the carboxyl group. The generation of a radical from the carbonyl group in the compound (A) and the decarboxylation of the carboxyl group in the compound (A) do not need to be caused by the light (active energy rays) in the same wavelength range. However, because the step 2 is a step of causing the sol-gel reaction and the radical polymerization, the ene-thiol reaction, or the yne-thiol reaction to simultaneously proceed, it is preferable that the generation of a radical from the carbonyl group in the compound (A) and the decarboxylation of the carboxyl group in the compound (A) are caused by the light (active energy rays) in the same wavelength range. In other words, it is preferable that the compound (A) has a photosensitive group that allows the generation of a radical from the carbonyl group and the decarboxylation of the carboxyl group to proceed by the light (active energy rays) in the same wavelength range. It should be noted that from the viewpoint of versatility, it is preferable that the compound (A) absorbs at least one or more kinds of light (active energy rays) among the i-line, the h-line, and the g-line in the wavelength range. The compound (E) is a compound which exhibits sensitivity with respect to light (active energy rays) generally having a wavelength of 100 to 780 nm, preferably having a wavelength of 200 to 450 nm, and more preferably having a wavelength of 350 to 450 nm, generates a radical from the carbonyl group in the compound (E) by absorbing the light (active energy rays), and generates a base by being decarboxylated. The generation of a radical from the carbonyl group in the compound (E) and the generation of a base in the compound (E) do not need to be caused by the light (active energy rays) in the same wavelength range. However, because the step 2 is a step of causing the sol-gel reaction and the radical polymerization, the ene-thiol reaction, or the yne-thiol reaction to simultaneously proceed, it is preferable that the generation of a radical from the carbonyl group in the compound (E) and the generation of a base in the compound (E) are caused by the light (active energy rays) in the same wavelength range. In other words, it is preferable that the compound (E) has a photosensitive group that allows the generation of a radical from the carbonyl group and the generation of a base to proceed by the light (active energy rays) in the same wavelength range. It should be noted that from the viewpoint of versatility, it is preferable that the compound (E) absorbs at least one or more kinds of light (active energy rays) among the i-line, the h-line, and the g-line in the wavelength range.

It is preferable that the compound (A) and the compound (E) in the step 2 in the photocuring method of the present invention are decomposed by the light (active energy rays) in the same wavelength range. That is, it is preferable that the generation of a radical from the carbonyl group in the compound (A), the decarboxylation of the carboxyl group in the compound (A), the generation of a radical from the carbonyl group in the compound (E), and the generation of a base in the compound (E) are caused by the light (active energy rays) in the same wavelength range. In other words, it is preferable that each of the compound (A) and the compound (E) has a photosensitive group that allows the generation of a radical from the carbonyl group in the compound (A), the decarboxylation of the carboxyl group in the compound (A), the generation of a radical from the carbonyl group in the compound (E), and the generation of a base in the compound (E) to proceed by the light (active energy rays) in the same wavelength range. Particularly, it is more preferable that the photosensitive groups of the compound (A) and the compound (E) have the same structure. In a case where the compound (A) and the compound (E) having photosensitive groups of the same structure are selected, radicals of the compound (A) and the compound (E) can be simultaneously generated, the radical polymerization, the ene-thiol reaction, or the yne-thiol reaction can smoothly proceed, and the loss of the carboxyl group through decarboxylation of the compound (A) and the generation of a base from the compound (E) can simultaneously proceed. Accordingly, the pH in the reaction system can rapidly shift to an alkaline pH from an acidic pH, and the sol-gel reaction can be efficiently performed.

In the photocuring method of the present invention, the compound (A) and the compound (E) may be the same compound, and a compound functioning as both the compound (A) and the compound (E) may be used instead of the compound (A) and the compound (E). Specific examples of such a compound include (A/E) compound having a carbonyl group generating a radical by photoirradiation, a carboxyl group decarboxylated by photoirradiation, and a group generating a base by being decarboxylated by photoirradiation. The compound (A/E) is a compound showing acidity because it has a carboxyl group and is hiding a base therein. However, in a case where the compound is irradiated with light (active energy rays), the carboxyl group is decarboxylated, and a base is generated. As a result, the compound can generate a radical while exhibiting alkalinity. That is, the compound (A/E) is a compound which is a carboxylic acid and can function as both the photobase generator and the photo-radical generator. In a case where the compound (A/E) is used instead of the compound (A) and the compound (E), it is possible to significantly reduce the equivalent (used amount) of the compound (A) and the compound (E) with respect to the silane coupling agent (B). It should be noted that in a case where the compound (A/E) is used instead of the compound (A) and the compound (E), the step 1 and the step 2 are specifically as described below.

Step 1: this is a step in which in the presence of (A/E) compound having a carbonyl group generating a radical by photoirradiation, a carboxyl group decarboxylated by photoirradiation, and a group generating a base by being decarboxylated by photoirradiation, (B) silane coupling agent having a mercapto group or a (meth)acryl group is reacted with (C) water under acidic conditions to obtain (D) silane compound having a mercapto group or a (meth)acryl group and at least one silanol group.

Step 2: this is a step in which in the presence of the compound (A/E), the compound (A/E) is irradiated with light to create alkaline conditions in a reaction system by decarboxylating the carboxyl group of the compound (A/E) and generating a base, and a radical is generated from the compound (A/E) to generate a crosslinked product containing a constitutional unit derived from the silane compound (D) from the silane compound (D) and, if necessary, from (F) compound having two or more polymerizable unsaturated groups.

The content of the compound (A) in the step 1 may be appropriately determined based on the molar amount of the silane coupling agent (B). The content of the compound (A) with respect to the molar amount of the silane coupling agent (B) is generally 0.001 to 1 equivalent, preferably 0.005 to 0.1 equivalents, and more preferably 0.005 to 0.05 equivalents. In a case where the compound (A) having the number of equivalent in a preferred range or having the number of equivalent in a more preferred range is used, the step 1 can smoothly proceed using the compound (A) at a smaller content.

The content of (C) water in the step 1 may be appropriately determined based on the molar amount of the silane coupling agent (B). The content of (C) water with respect to the molar amount of the silane coupling agent (B) is generally 0.1 to 10 equivalents, preferably 0.5 to 5 equivalents, and more preferably 1 to 2 equivalents. In a case where (C) water having the number of equivalent in a preferred range or having the number of equivalent in a more preferred range is used, it is easy to finish the step 1 in a state where only some of the alkoxysilyl groups are converted into silanol groups, that is, at the state where the alkoxysilyl groups are partially hydrolyzed.

The content of the silane compound (D) in the step 1 depends on the amount of the silane coupling agent (B) used. That is, in the step 1, in a case where the entirety of the used silane coupling agent (B) reacts with (C) water, a silane compound (D) of the same molar amount as the molar amount of the silane coupling agent (B) is generated. In contrast, in a case where the used silane coupling agent (B) is incompletely reacted and remains in the reaction system after the step 1 is finished, or in a case where a side reaction of the silane coupling agent (B) occurs, a silane compound (D) of the molar amount smaller than the molar amount of the silane coupling agent (B) used is generated.

The content of the compound (E) in the step 2 may be appropriately determined based on the molar amount of the silane coupling agent (B). The content of the compound (E) with respect to the molar amount of the silane coupling agent (B) is generally 0.001 to 1 equivalent, preferably 0.005 to 0.1 equivalents, and more preferably 0.005 to 0.05 equivalents. In a case where the compound (E) having the number of equivalent in a preferred range or having the number of equivalent in a more preferred range is used, the step 2 can smoothly proceed using the compound (E) at a smaller content.

The content of the compound (A/E) in the step 1 and the step 2 may be appropriately determined based on the molar amount of the silane coupling agent (B). The content of the compound (A/E) with respect to the molar amount of the silane coupling agent (B) is generally 0.001 to 1 equivalent, preferably 0.005 to 0.1 equivalents, and more preferably 0.005 to 0.05 equivalents. In a case where the compound (A/E) having the number of equivalent in a preferred range or having the number of equivalent in a more preferred range is used, the step 1 and the step 2 can smoothly proceed using the compound (A/E) at a smaller content.

In the step 2, in a case where the reaction system contains the compound (F), the content of the compound (F) may be determined as the molar amount of the polymerizable unsaturated groups in the compound (F), based on the molar amount of the mercapto group or the (meth)acryl group in the silane coupling agent (B). The content of the compound (F) may be determined such that the molar amount of the polymerizable unsaturated groups in the compound (F) with respect to the molar amount of the mercapto group or the (meth)acryl group in the silane coupling agent (B) generally becomes 0.01 to 10 moles, preferably becomes 0.1 to 5 moles, more preferably becomes 0.5 to 3 moles, and even more preferably becomes 0.7 to 1.5 moles. In a case where the compound (F) of a molar amount converted from the mol number in a preferred range, the mol number in a more preferred range, or the mol number in an even more preferred range is used, a uniform crosslinked product (resin) is easily obtained.

The light (active energy rays) according to the step 2 in the photocuring method of the present invention is not particularly limited as long as the compound (A) and the compound (E) or the compound (A/E) senses the light and generate a radical, and the light (active energy rays) has a wavelength at which decarboxylation or the generation of an acid can occur. Particularly, light (active energy rays) having a main wavelength in a range of 100 to 780 nm is preferable, light (active energy rays) having a main wavelength in a range of 200 to 450 nm is more preferable, and light (active energy rays) having a main wavelength in a range of 350 to 450 nm is even more preferable. In a case where a UV absorber is used in the photocuring method of the present invention, it is desirable to select a wavelength of light (active energy rays) such that the sol-gel reaction and the radical polymerization, the ene-thiol reaction, or the yne-thiol reaction proceed without hindering the absorption of light (active energy rays) by the UV absorber.

The irradiation amount (cumulative exposure amount) of the light (active energy rays) is not particularly limited, as long as the sol-gel reaction and the radical polymerization, the ene-thiol reaction, or the yne-thiol reaction proceed in the reaction of the step 2, and a crosslinked product containing a constitutional unit derived from the silane compound (D) is obtained. The irradiation amount (cumulative exposure amount) of the light (active energy rays) is preferably equal to or greater than 0.1 J, more preferably equal to or greater than 0.5 J, and even more preferably equal to or greater than 1.0 J. In a case where the irradiation amount (cumulative exposure amount) of the light (active energy rays) is equal to or greater than 1.0 J, a crosslinked product (resin) having high crosslinking density tends to be obtained, and as a result, a crosslinked product (resin) having excellent solvent resistance and high hardness tends to be obtained.

In the step 2 of the photocuring method of the present invention, the irradiation of light (active energy rays) may be performed by appropriately selecting light (active energy rays) having a main wavelength within the range described above, for a time by which the irradiation amount (cumulative exposure amount) of the light (active energy rays) becomes equal to or greater than the irradiation amount (cumulative exposure amount) described above. It should be noted that the irradiation of light (active energy rays) may be performed using a general exposure device which can radiate light (active energy rays) having the wavelength described above.

In the photocuring method of the present invention, the step 1 may be performed at a temperature generally in a range of −20° C. to 60° C., preferably in a range of 0° C. to 50° C., and more preferably in a range of 100° C. to 40° C. In addition, in the photocuring method of the present invention, the step 2 may be performed at a temperature generally in a range of −20° C. to 60° C., preferably in a range of 0° C. to 50° C., and more preferably in a range of 10° C. to 40° C. The photocuring method of the present invention can be performed under mild conditions as described above. Therefore, the photocuring method of the present invention is an excellent photocuring method.

The step 1 and the step 2 in the photocuring method of the present invention are not particularly limited as long as they are performed at a pressure in a range in which a series of steps can be smoothly carried out. The step 1 and the step 2 may be generally performed at normal pressure.

In the step 1 and the step 2 in the photocuring method of the present invention, the reaction time (time for which the step 1 and the step 2 are performed) may be set such that a crosslinked product which has desired crosslinking density, hardness, and the like and contains a constitutional unit derived from the silane compound (D) is obtained. In the step 1, the reaction time varies with the number of equivalent of the compound (A) and/or (C) water with respect to the silane coupling agent (B), the reaction temperature, the pressure, and the like. In the step 2, the reaction time varies with the wavelength and/or the irradiation amount (cumulative exposure amount) of the light (active energy rays), the number of equivalent of the compound (E) with respect to the silane compound (D), the reaction temperature, the pressure, and the like. Therefore, the reaction time cannot be mentioned as fixed numbers. However, for example, the reaction time of the step 1 (time for which the step 1 is performed) is generally 1 minute to 24 hours, preferably 10 minutes to 12 hours, and more preferably 20 minutes to 6 hours. Furthermore, for example, the reaction time of the step 2 (time for which the step 2 is performed) is generally 1 minute to 24 hours, preferably 10 minutes to 12 hours, and more preferably 20 minutes to 6 hours.

The specific procedure of a method for obtaining a crosslinked product (resin) by using the photocuring method of the present invention will be described below. First, a reaction container is prepared which contains (A) compound having a carbonyl group generating a radical by photoirradiation and a carboxyl group decarboxylated by photoirradiation, (B) silane coupling agent having a mercapto group or a (meth)acryl group, (E) compound having a carbonyl group generating a radical by photoirradiation and a group generating a base by being decarboxylated by photoirradiation, and an organic solvent which is used if necessary. Then, (C) water is added to the reaction container such that the silane coupling agent (B) reacts with (C) water for a predetermined time, thereby obtaining (D) silane compound having a mercapto group or a (meth)acryl group and at least one silanol group (step 1). Then, if necessary, (F) compound having two or more polymerizable unsaturated groups is added to a composition (photocuring resin composition) containing the silane compound (D) obtained in the step 1, the surface of an appropriate solid such as a substrate is coated with the composition (photocuring resin composition), and, if necessary, a drying operation such as baking is performed to form a coating film. Thereafter, the obtained coating film is irradiated with light (active energy rays) having an appropriate wavelength such that the irradiation amount (cumulative exposure amount) becomes equal to or greater than a predetermined amount. In this way, the carboxyl group in the compound (A) is decarboxylated, a base is generated from the compound (E), alkaline conditions are created in the reaction system, and radicals are generated from the compound (A) and the compound (E). By simultaneously generating the base and the radicals, the sol-gel reaction of the silane compound (D) and the radical polymerization, the ene-thiol reaction, or the yne-thiol reaction are performed. In this way, a crosslinked product (resin) containing a constitutional unit derived from the silane compound (D) can be obtained (step 2). In a case where a pattern is formed using the photocuring method of the present invention, by performing the irradiation of light (active energy rays) in the step 2 through an appropriate pattern mask and then performing a development treatment by using an appropriate developer, it is possible to obtain a crosslinked product (resin) which has an appropriate pattern and contains a constitutional unit derived from the silane compound (D). As described above, the step 1 and the step 2 in the photocuring method of the present invention do not need to be consecutively performed. Between the step 1 and the step 2, for example, the coating step, the baking step, the drying step, and the like may be performed, or the step 1 and the step 2 may be consecutively performed.

As the coating method in the coating step, the baking method in the baking step, the drying method in the drying step, the development treatment method in the developing step, and the like, known methods may be appropriately adopted. For example, a baking temperature in the baking step is generally 80° C. to 200° C. and preferably 100° C. to 180° C., and a baking time is generally 30 seconds to 30 minutes and preferably 1 minute to 15 minutes. Examples of the development treatment method in the developing step include a method in which the crosslinked product (resin) obtained using the photocuring method of the present invention is immersed in an organic solvent such as acetone or methyl ethyl ketone for 10 seconds to 5 minutes, a method in which the crosslinked product (resin) is immersed in an aqueous alkaline solution containing potassium hydroxide, tetramethylammoniumhydroxide (TMAH), and the like for 10 seconds to 5 minutes, and the like.

(A) compound having a carbonyl group generating a radical by photoirradiation and a carboxyl group decarboxylated by photoirradiation according to the photocuring method of the present invention is a carboxylic acid exhibiting sensitivity with respect to light (active energy rays). More specifically, the compound (A) has a photosensitive group exhibiting sensitivity with respect to light (active energy rays), in which the photosensitive group has a carbonyl group that can generate a radical by absorbing light and a carboxyl group that loses acidity by decarboxylated by absorbing light. Specific examples of the compound (A) include a compound represented by the following general formula [1].

General formula [1]

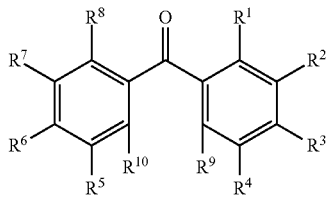

wherein $R^1$ to $R^8$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by the following general formula [2], or a group represented by the following general formula [3], $R^9$ and $R^{10}$ each independently represent a hydrogen atom, an alkyl group having 1 to 12 carbon atoms, an aryl group having 6 to 14 carbon atoms, an arylalkyl group having 7 to 15 carbon atoms, ah alkoxy group having 1 to 12 carbon atoms, a halogen atom, or a nitro group; or represent a state where $R^9$ and $R^{10}$ are bonded to each other through an oxygen atom, a sulfur atom, or a carbonyl group, provided that at least one of the groups represented by $R^1$ to $R^8$ is the group represented by the following general formula [2].

General formula [2]

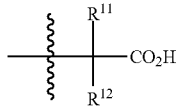

wherein $R^{11}$ and $R^{12}$ each independently represent a hydrogen atom, an alkyl group having 1 to 6 carbon atoms, or a hydroxyalkyl group having 1 to 6 carbon atoms.

General formula [3]

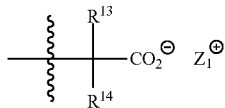

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

The alkyl group having 1 to 12 carbon atoms represented by $R^1$ to $R^{10}$ in the general formula [1] may be any of linear, branched, and cyclic alkyl groups. Examples thereof include a methyl group, an ethyl group, a n-propyl group, an isopropyl group, a cyclopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a n-undecyl group, a cycloundecyl group, a n-dodecyl group, a cyclododecyl group, a norbornyl group (norbornan-χ-yl group), a bornyl group (bornan-χ-yl group), a menthyl group (menth-χ-yl group), an adamantyl group, a decahydronaphthyl group, and the like. Among these alkyl groups, a linear, branched, or cyclic alkyl group having 1 to 6 carbon atoms is preferable. Among these, a linear, branched, or cyclic alkyl group having 1 to 4 carbon atoms is more preferable, and a methyl group is particularly preferable.

The aryl group having 6 to 14 carbon atoms represented by $R^1$ to $R^{10}$ in the general formula [1] may be any of monocyclic or fused polycyclic rings. Examples thereof include a phenyl group, a naphthyl group, an anthracenyl group, and the like. Among these aryl groups, the phenyl group is preferable.

The arylalkyl group having 7 to 15 carbon atoms represented by $R^1$ to $R^{10}$ in the general formula [1] may be any of monocyclic or fused polycyclic rings. Examples thereof include a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (anthrylmethyl group), a phenanthrenylmethyl group (phenanthrylmethyl group), and the like. Among these arylalkyl groups, the benzyl group is preferable.

The alkoxy group having 1 to 12 carbon atoms represented by $R^1$ to $R^{10}$ in the general formula [1] may be any of linear, branched, and cyclic alkoxy groups. Examples thereof include a methoxy group, an ethoxy group, a n-propoxy group, an isopropoxy group, a cyclopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, a n-heptyloxy group, an isoheptyloxy group, a sec-heptyloxy group, a tert-heptyloxy group, a neoheptyloxy group, a cycloheptyloxy group, a n-octyloxy group, an isooctyloxy group, a sec-octyloxy group, a tert-octyloxy group, a neooctyloxy group, a 2-ethylhexyloxy group, a cyclooctyloxy group, a n-nonyloxy group, an isononyloxy group, a sec-nonyloxy group, a tert-nonyloxy group, a neononyloxy group, a cyclononyloxy group, a n-decyloxy group, an isodecyloxy group, a sec-decyloxy group, a tert-decyloxy group, a neodecyloxy group, a cyclodecyloxy group, a n-undecyloxy group, a cycloundecyloxy group, a n-dodecyloxy group, a cyclododecyloxy group, a norbornyloxy group (norbornan-χ-yloxy group), a bornyloxy group (bornan-χ-yloxy group), a menthyloxy group (menth-χ-yloxy group), an adamantyloxy group, a decahydronaphthyloxy group, and the like. Among these alkyloxy groups, alkoxy groups having 1 to 6 carbon atoms is preferable. Among these, a linear, branched, or cyclic alkoxy group having 1 to 4 carbon atoms is more preferable, and a methoxy group is particularly preferable.

Examples of the halogen atom represented by $R^1$ to $R^{10}$ in the general formula [1] include a fluorine atom, a chlorine atom, a bromine atom, an iodine atom, and the like. Among these, the fluorine atom and the chlorine atom are preferable.

The alkyl group having 1 to 6 carbon atoms represented by $R^{11}$ and $R^{12}$ in the general formula [2] and $R^{13}$ and $R^{14}$ in the general formula [3] may be any of linear, branched, and cyclic alkyl groups. Examples thereof include a methyl group, an ethyl group, a n-propyl group, an isopropyl group, a cyclopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, and the like. Among these alkyl groups, a linear, branched, or cyclic alkyl group having 1 to 3 carbon atoms is preferable, and a methyl group is particularly preferable.

The hydroxyalkyl group having 1 to 6 carbon atoms represented by $R^{11}$ and $R^{12}$ in the general formula [2] and $R^{13}$ and $R^{14}$ in the general formula [3] may be any of linear, branched, and cyclic hydroxyalkyl groups, and the number of hydroxy groups bonded to the alkyl group is not limited to 1 and may be plural such as 2 to 4. Examples of such a hydroxyalkyl group include a hydroxymethyl group, a 1-hydroxyethyl group, a 2-hydroxyethyl group, a 1,2-dihydroxyethyl group, a 1-hydroxy-n-propyl group, a 2-hydroxy-n-propyl group, a 3-hydroxy-n-propyl group, a 1-hydroxy-1-methylethyl group, a 1-hydroxymethylethyl group, a 4-hydroxy-n-butyl group, a 5-hydroxy-n-pentyl group, a 6-hydroxy-n-hexyl group, and the like. Among these hydroxyalkyl groups, a linear, branched, or cyclic hydroxyalkyl group having 1 to 3 carbon atoms is preferable, and a hydroxymethyl group is more preferable.

The state where $R^9$ and $R^{10}$ in the general formula [1] are bonded to each other through an oxygen atom, a sulfur atom, or a carbonyl group means that $R^9$ and $R^{10}$ form a group represented by —O—, —S—, or —C(=O)— together.

In a case where $R^9$ and $R^{10}$ in the general formula [1] each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, or in a case where $R^9$ and $R^{10}$ are bonded to each other through an oxygen atom or a sulfur atom, it is desirable that the group represented by the general formula [2] and the group represented by the general formula [3] are bonded to any of $R^2$, $R^4$, $R^5$, and $R^7$. That is, in a case where $R^9$ and $R^{10}$ are bonded to each other through a carbonyl group, the group represented by the general formula [2] and the group represented by the general formula [3] may be bonded to any of $R^1$ to $R^8$. However, in a case where $R^9$ and $R^{10}$ are groups other than the above, it is desirable that the group represented by the general formula [2] and the group represented by the general formula [3] are bonded to any of $R^2$, $R^4$, $R^5$, and $R^7$.

As $R^1$ and $R^2$ in the general formula [1], a hydrogen atom and the group represented by the general formula [2] are preferable.

As $R^3$ and $R^6$ in the general formula [1], a hydrogen atom is preferable.

As $R^4$, $R^5$, and $R^8$ in the general formula [1], a hydrogen atom, the group represented by the general formula [2], and the group represented by the general formula [3] are preferable.

As $R^7$ in the general formula [1], a hydrogen atom, the group represented by the general formula [2], and the group represented by the general formula [3] are preferable. Among these, the hydrogen atom is more preferable.

As $R^9$ and $R^{10}$ in the general formula [1], a hydrogen atom or a group formed by $R^9$ and $R^{10}$ bonded to each other through an oxygen atom or a sulfur atom is preferable. Among these, the hydrogen atom or the group formed by $R^9$ and $R^{10}$ bonded to each other through the sulfur atom is more preferable.

As $R^{11}$ in the general formula [2] and $R^{13}$ in the general formula [3], a hydrogen atom and an alkyl group having 1 to 6 carbon atoms are preferable. Among these, the alkyl group having 1 to 6 carbon atoms is more preferable.

As $R^{12}$ in the general formula [2] and $R^{14}$ in the general formula [3], a hydrogen atom and an alkyl group having 1 to 6 carbon atoms are preferable. Among these, the hydrogen atom is more preferable.

Specific examples preferred as the compound (A) represented by the general formula [1] include compounds represented by the following general formulae [1-A] to [1-C].

General formula [1-A]

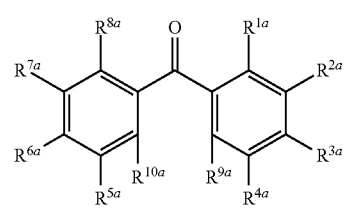

[1-A]

wherein $R^{2a}$, $R^{4a}$, $R^{5a}$, and $R^{7a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], and $R^{1a}$, $R^{3a}$, $R^{6a}$, $R^{8a}$, $R^{9a}$, and $R^{10a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of groups represented by $R^{2a}$, $R^{4a}$, $R^{5a}$, and $R^{7a}$ is the group represented by the general formula [2].

General formula [1-B]

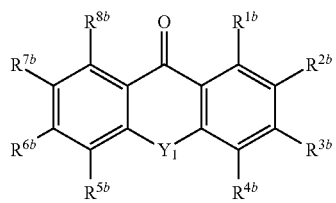

[1-B]

wherein $R^{2b}$, $R^{4b}$, $R^{5b}$, and $R^{7b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{1b}$, $R^{3b}$, $R^{6b}$, and $R^{8b}$ each independently represent a hydrogen atom, and an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and $Y_1$ represents an oxygen atom or a sulfur atom, provided that at least one of the groups represented by $R^{2b}$, $R^{4b}$, $R^{5b}$, and $R^{7b}$ is the group represented by the general formula [2].

General formula [1-C]

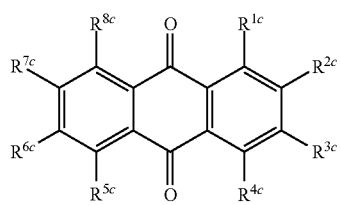

[1-C]

wherein $R^{1c}$ to $R^{8c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{1c}$ to $R^{8c}$ is the group represented by the general formula [2].

Specific examples of the alkyl group having 1 to 12 carbon atoms represented by $R^{1a}$ to $R^{10a}$ in the general formula [1-A], $R^{1b}$ to $R^{8b}$ in the general formula [1-B], and $R^{1c}$ to $R^{8c}$ in the general formula [1-C] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{1a}$ to $R^{10a}$ in the general formula [1-A], $R^{1b}$ to $R^{8b}$ in the general formula [1-B], and $R^{1c}$ to $R^{8c}$ in the general formula [1-C] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{1a}$ to $R^{10a}$ in the general formula [1-A], $R^{1b}$ to $R^{8b}$ in the general formula [1-B], and $R^{1c}$ to $R^{8c}$ in the general formula [1-C] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{1a}$ to $R^{10a}$ in the general formula [1-A], $R^{1b}$ to $R^{8b}$ in the general formula [1-B], and $R^{1c}$ to $R^{8c}$ in the general formula [1-C] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{1a}$ to $R^{10a}$ in the general formula [1-A], $R^{1b}$ to $R^{8b}$ in the general formula [1-B], and $R^{1c}$ to $R^{8c}$ in the general formula [1-C] are the same as the specific examples of the halogen atom represented by $R^1$ to $R^{10}$ in the general formula [1], and preferred specific examples are also the same.

As $R^{1a}$, $R^{3a}$, $R^{6a}$, $R^{8a}$, $R^{9a}$, and $R^{10a}$ in the general formula [1-A], a hydrogen atom is preferable.

As $R^{2a}$ in the general formula [1-A], the group represented by the general formula [2] is preferable.

As $R^{4a}$ in the general formula [1-A], a hydrogen atom, the group represented by the general formula [2], and the group represented by the general formula [3] are preferable.

As $R^{5a}$ and $R^{7a}$ in the general formula [1-A], a hydrogen atom, the group represented by the general formula [2], and the group represented by the general formula [3] are preferable. Among these, the hydrogen atom is more preferable.

Examples of the preferred combination of $R^{1a}$ to $R^{10a}$ in the general formula [1-A] include combinations represented by <1> to <6> in Table 1.

TABLE 1

| Combination | $R^{1a}$ | $R^{2a}$ | $R^{3a}$ | $R^{4a}$ | $R^{5a}$ | $R^{6a}$ | $R^{7a}$ | $R^{8a}$ | $R^{9a}$ | $R^{10a}$ |
|---|---|---|---|---|---|---|---|---|---|---|
| <1> | Hydrogen atom | General formula [2] | Hydrogen atom | Hydrogen atom | Hydrogen atom | Hydrogen atom | Hydrogen atom | Hydrogen atom | Hydrogen atom | Hydrogen atom |
| <2> | Hydrogen atom | General formula [2] | Hydrogen atom | Hydrogen atom | Hydrogen atom | Hydrogen atom | General formula [2] | Hydrogen atom | Hydrogen atom | Hydrogen atom |
| <3> | Hydrogen atom | General formula [2] | Hydrogen atom | General formula [2] | Hydrogen atom | Hydrogen atom | Hydrogen atom | Hydrogen atom | Hydrogen atom | Hydrogen atom |
| <4> | Hydrogen atom | General formula [2] | Hydrogen atom | General formula [2] | Hydrogen atom | Hydrogen atom | General formula [2] | Hydrogen atom | Hydrogen atom | Hydrogen atom |
| <5> | Hydrogen atom | General formula [2] | Hydrogen atom | General formula [2] | General formula [2] | Hydrogen atom | General formula [2] | Hydrogen atom | Hydrogen atom | Hydrogen atom |
| <6> | Hydrogen atom | General formula [2] | Hydrogen atom | General formula [3] | Hydrogen atom | Hydrogen atom | Hydrogen atom | Hydrogen atom | Hydrogen atom | Hydrogen atom |

As $R^{1b}$, $R^{3b}$, $R^{6b}$, and $R^{8b}$ in the general formula [1-B], a hydrogen atom is preferable.

As $R^{2b}$ in the general formula [1-B], the group represented by the general formula [2] is preferable.

As $R^{4b}$ in the general formula [1-B], a hydrogen atom, the group represented by the general formula [2], and the group represented by the general formula [3] are preferable.

As $R^{5b}$ and $R^{7b}$ in the general formula [1-B], a hydrogen atom, the group represented by the general formula [2], and the group represented by the general formula [3] are preferable. Among these, the hydrogen atom is more preferable.

As $Y_1$ in the general formula [1-B], a sulfur atom is preferable.

Examples of the preferred combination of $Y_1$ and $R^{1b}$ to $R^{8b}$ in the general formula [1-B] include combinations represented by <1> to <12> in Table 2.

TABLE 2

| Combination | $Y_1$ | $R^{1b}$ | $R^{2b}$ | $R^{3b}$ | $R^{4b}$ | $R^{5b}$ | $R^{6b}$ | $R^{7b}$ | $R^{8b}$ |
|---|---|---|---|---|---|---|---|---|---|
| <1> | Oxygen atom | Hydrogen atom | General formula [2] | Hydrogen atom | Hydrogen atom | Hydrogen atom | Hydrogen atom | Hydrogen atom | Hydrogen atom |
| <2> | Oxygen atom | Hydrogen atom | General formula [2] | Hydrogen atom | Hydrogen atom | Hydrogen atom | Hydrogen atom | General formula [2] | Hydrogen atom |
| <3> | Oxygen atom | Hydrogen atom | General formula [2] | Hydrogen atom | General formula [2] | Hydrogen atom | Hydrogen atom | Hydrogen atom | Hydrogen atom |
| <4> | Oxygen atom | Hydrogen atom | General formula [2] | Hydrogen atom | General formula [2] | Hydrogen atom | Hydrogen atom | General formula [2] | Hydrogen atom |
| <5> | Oxygen atom | Hydrogen atom | General formula [2] | Hydrogen atom | General formula [2] | General formula [2] | Hydrogen atom | General formula [2] | Hydrogen atom |
| <6> | Oxygen atom | Hydrogen atom | General formula [2] | Hydrogen atom | General formula [3] | Hydrogen atom | Hydrogen atom | Hydrogen atom | Hydrogen atom |
| <7> | Sulfur atom | Hydrogen atom | General formula [2] | Hydrogen atom | Hydrogen atom | Hydrogen atom | Hydrogen atom | Hydrogen atom | Hydrogen atom |
| <8> | Sulfur atom | Hydrogen atom | General formula [2] | Hydrogen atom | Hydrogen atom | Hydrogen atom | Hydrogen atom | General formula [2] | Hydrogen atom |
| <9> | Sulfur atom | Hydrogen atom | General formula [2] | Hydrogen atom | General formula [2] | Hydrogen atom | Hydrogen atom | Hydrogen atom | Hydrogen atom |
| <10> | Sulfur atom | Hydrogen atom | General formula [2] | Hydrogen atom | General formula [2] | Hydrogen atom | Hydrogen atom | General formula [2] | Hydrogen atom |
| <11> | Sulfur atom | Hydrogen atom | General formula [2] | Hydrogen atom | General formula [2] | General formula [2] | Hydrogen atom | General formula [2] | Hydrogen atom |
| <12> | Sulfur atom | Hydrogen atom | General formula [2] | Hydrogen atom | General formula [3] | Hydrogen atom | Hydrogen atom | Hydrogen atom | Hydrogen atom |

As $R^{1c}$ and $R^{2c}$ in the general formula [1-C], a hydrogen atom and the group represented by the general formula [2] are preferable.

As $R^{3c}$ and $R^{6c}$ in the general formula [1-C], a hydrogen atom is preferable.

As $R^{4c}$, $R^{5c}$, and $R^{8c}$ in the general formula [1-C], a hydrogen atom, the group represented by the general formula [2], and the group represented by the general formula [3] are preferable.

As $R^{7c}$ in the general formula [1-C], a hydrogen atom, the group represented by the general formula [2], and the group represented by the general formula [3] are preferable. Among these, the hydrogen atom is more preferable.

Examples of the preferred combination of $R^{1c}$ to $R^{8c}$ in the general formula [1-C] include combinations represented by <1> to <12> in Table 3.

TABLE 3

| Combination | $R^{1c}$ | $R^{2c}$ | $R^{3c}$ | $R^{4c}$ | $R^{5c}$ | $R^{6c}$ | $R^{7c}$ | $R^{8c}$ |
|---|---|---|---|---|---|---|---|---|
| <1> | Hydrogen atom | General formula [2] | Hydrogen atom | Hydrogen atom | Hydrogen atom | Hydrogen atom | Hydrogen atom | Hydrogen atom |
| <2> | Hydrogen atom | General formula [2] | Hydrogen atom | Hydrogen atom | Hydrogen atom | Hydrogen atom | General formula [2] | Hydrogen atom |

TABLE 3-continued

| Combination | $R^{1c}$ | $R^{2c}$ | $R^{3c}$ | $R^{4c}$ | $R^{5c}$ | $R^{6c}$ | $R^{7c}$ | $R^{8c}$ |
|---|---|---|---|---|---|---|---|---|
| <3> | Hydrogen atom | General formula [2] | Hydrogen atom | General formula [2] | Hydrogen atom | Hydrogen atom | Hydrogen atom | Hydrogen atom |
| <4> | Hydrogen atom | General formula [2] | Hydrogen atom | General formula [2] | Hydrogen atom | Hydrogen atom | General formula [2] | Hydrogen atom |
| <5> | Hydrogen atom | General formula [2] | Hydrogen atom | General formula [2] | General formula [2] | Hydrogen atom | General formula [2] | Hydrogen atom |
| <6> | Hydrogen atom | General formula [2] | Hydrogen atom | General formula [2] | Hydrogen atom | Hydrogen atom | Hydrogen atom | Hydrogen atom |
| <7> | General formula [2] | Hydrogen atom | Hydrogen atom | Hydrogen atom | Hydrogen atom | Hydrogen atom | Hydrogen atom | Hydrogen atom |
| <8> | General formula [2] | Hydrogen atom | Hydrogen atom | General formula [2] | Hydrogen atom | Hydrogen atom | Hydrogen atom | Hydrogen atom |
| <9> | General formula [2] | Hydrogen atom | Hydrogen atom | Hydrogen atom | General formula [2] | Hydrogen atom | Hydrogen atom | Hydrogen atom |
| <10> | General formula [2] | Hydrogen atom | Hydrogen atom | Hydrogen atom | Hydrogen atom | Hydrogen atom | Hydrogen atom | General formula [2] |
| <11> | General formula [2] | Hydrogen atom | Hydrogen atom | General formula [2] | General formula [2] | Hydrogen atom | Hydrogen atom | General formula [2] |
| <12> | General formula [2] | General formula [2] | General formula [2] | General formula [2] | General formula [2] | General formula [2] | General formula [2] | General formula [2] |

Specific examples of the compound (A) represented by the general formula [1-A] include compounds represented by the following formulae [1-A1] to [1-A10].

Formulae [1-A1] to [1-A10]

[1-A1]
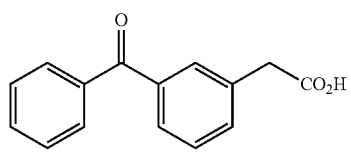

[1-A2]
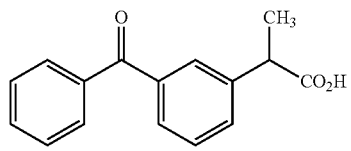

[1-A3]
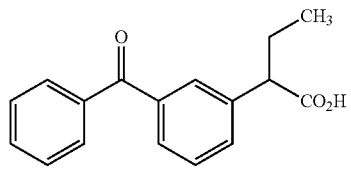

[1-A4]
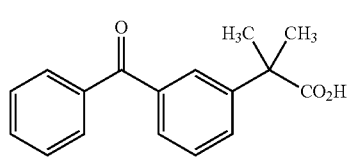

[1-A5]
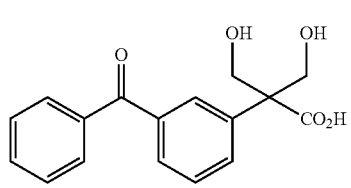

[1-A6]
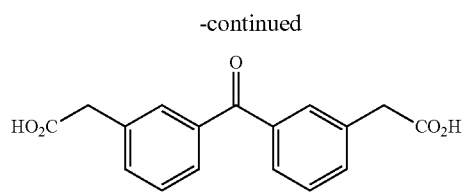

[1-A7]
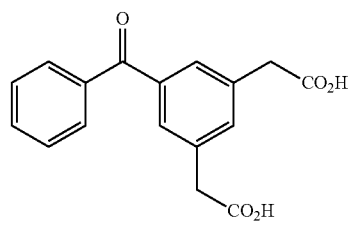

[1-A8]
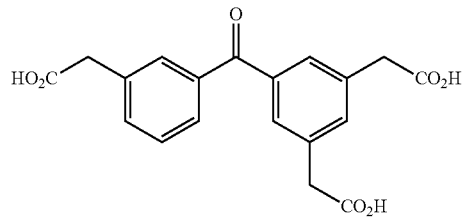

[1-A9]
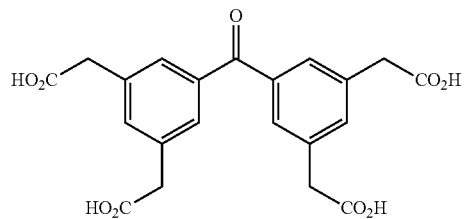

[1-A10]
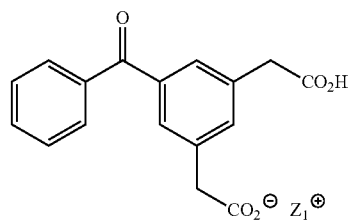

Specific examples of the compound (A) represented by the general formula [1-B] include compounds represented by the following formulae [1-B1] to [1-B12].
Formulae [1-B1] to [1-B12]
[1-B1]
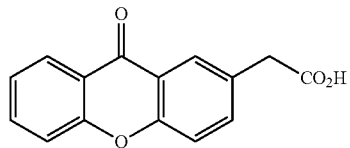
[1-B2]
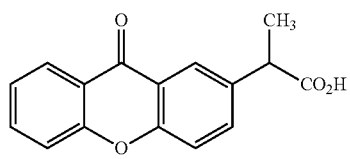
[1-B3]
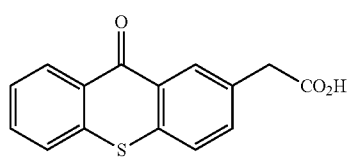
[1-B4]
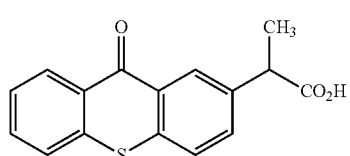
[1-B5]
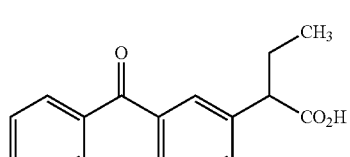
[1-B6]
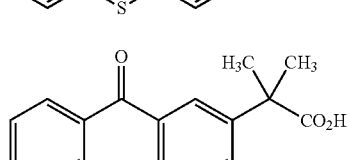
[1-B7]
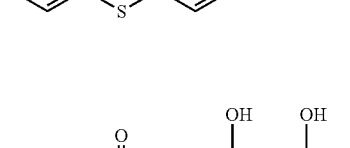
[1-B8]
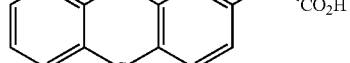
[1-B9]
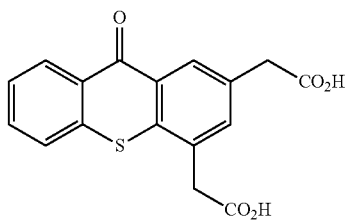
[1-B10]
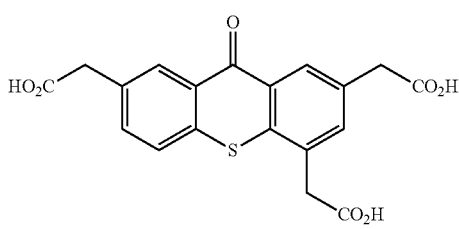
[1-B11]
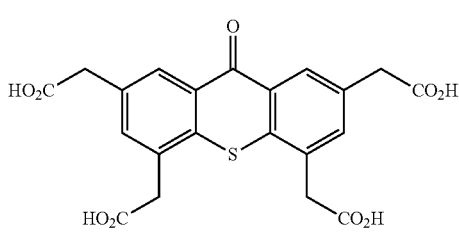
[1-B12]
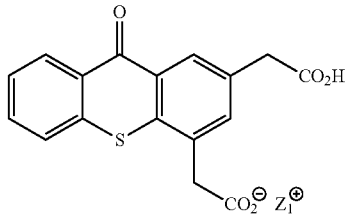
Specific examples of the compound (A) represented by the general formula [1-C] include compounds represented by the following formulae [1-C1] to [1-C14].
Formulae [1-C1] to [1-C14]
[1-C1]
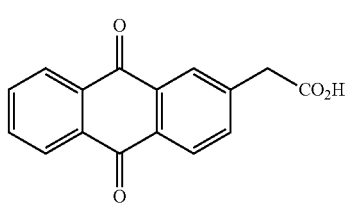
[1-C2]
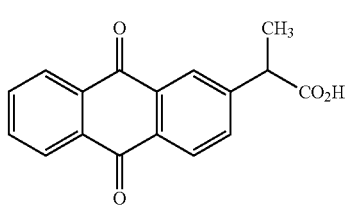
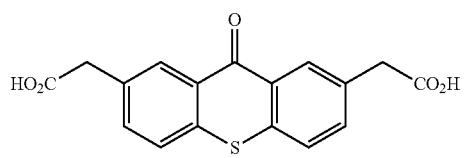

[1-C3]
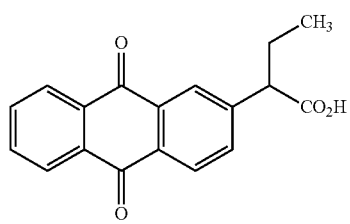

[1-C4]
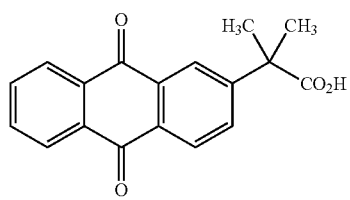

[1-C5]
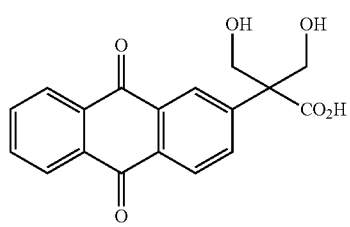

[1-C6]
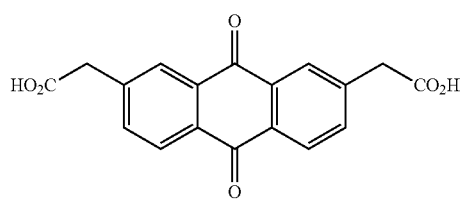

[1-C7]
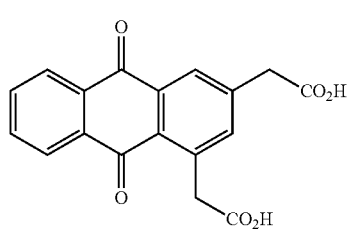

[1-C8]
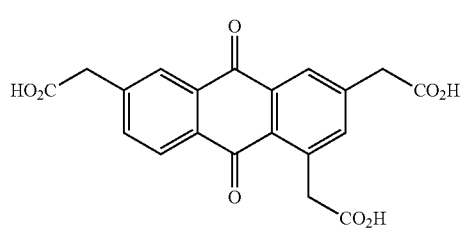

[1-C9]
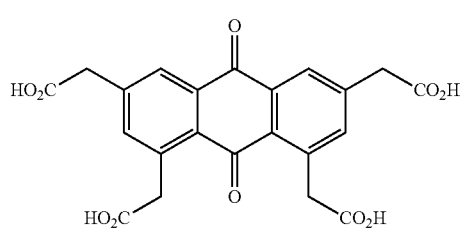

[1-C10]

[1-C11]

[1-C12]

[1-C13]

[1-C14]

As the compound (A), from the viewpoint of ease of availability of raw materials at the time of manufacturing the compound (A) and economic efficiency, the compound represented by the general formula [1-A] and the compound represented by the general formula [1-B] are preferable. In addition, in a case where the UV absorber is used in the photocuring method of the present invention, among the compounds (A), sometimes the compound represented by the general formula [1-B] in which $Y_1$ represents a sulfur atom is preferable. Such a compound exhibits sensitivity with respect to light (active energy rays) having a main wavelength at 350 to 450 nm. Therefore, it is possible to allow the sol-gel reaction and the radical polymerization, the ene-thiol reaction, or the yne-thiol reaction to smoothly proceed without hindering the absorption of the light (active energy rays) by the UV absorber.

The compound represented by the formula [1-A10], the compound represented by the formula [1-B12], and the compound represented by the formula [1-C10] among the above formulae have a carbonyl group generating a radical by the irradiation of light (active energy rays), a carboxyl group decarboxylated by the irradiation of light (active energy rays), and a group generating a base through the decarboxylation of the carboxyl group by the irradiation of light (active energy rays). These compounds correspond to (A/E) compound having a carbonyl group generating a radical by photoirradiation, a carboxyl group decarboxylated by photoirradiation, and a group generating a base by being decarboxylated by photoirradiation. That is, these compounds are included in the compound (A/E) according to the photocuring method of the present invention.

(E) compound having a carbonyl group generating a radical by photoirradiation and a group generating a base by being decarboxylated by photoirradiation according to the photocuring method of the present invention is a photobase generator which exhibits sensitivity with respect to light (active energy rays). More specifically, the compound (E) has a photosensitive group exhibiting sensitivity with respect to light (active energy rays), in which the photosensitive group has a carbonyl group that can generate a radical by absorbing light and a group that generates a base by being decarboxylated by absorbing light. Specific examples of the compound (E) include a compound represented by the following general formula [4].

General formula [4]

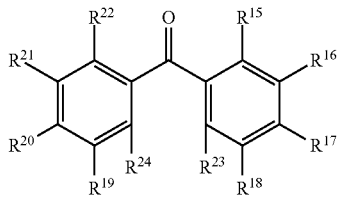

[4]

wherein $R^{15}$ to $R^{22}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by the following general formula [2], or a group represented by the following general formula [3], $R^{23}$ and $R^{24}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{23}$ and $R^{24}$ are bonded to each other through an oxygen atom, a sulfur atom, or a carbonyl group, provided that at least one of the groups represented by $R^{15}$ to $R^{22}$ is the group represented by the following general formula [3].

General formula [2]

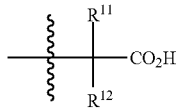

[2]

wherein $R^{11}$ and $R^{12}$ each independently represent a hydrogen atom, an alkyl group having 1 to 6 carbon atoms, or a hydroxyalkyl group having 1 to 6 carbon atoms.

General formula [3]

[3]

wherein $Z_1^+$ represents an amidinium cation, a guanidium cation, a biguanidinium cation, or a phosphazenium cation, and $R^{13}$ and $R^{14}$ each independently represent a hydrogen atom an alkyl group having 1 to 6 carbon atoms, or a hydroxyalkyl group having 1 to 6 carbon atoms.

Specific examples of the alkyl group having 1 to 12 carbon atoms represented by $R^{15}$ to $R^{24}$ in the general formula [4] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{15}$ to $R^{24}$ in the general formula [4] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{15}$ to $R^{24}$ in the general formula [4] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{15}$ to $R^{24}$ in the general formula [4] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{15}$ to $R^{24}$ in the general formula [4] are the same as the specific examples of the halogen atom represented by $R^1$ to $R^{10}$ in the general formula [1], and preferred specific examples are also the same.

The state where $R^{23}$ and $R^{24}$ in the general formula [4] are bonded to each other through an oxygen atom, a sulfur atom, or a carbonyl group means that $R^{23}$ and $R^{24}$ form a group represented by —O—, —S—, or —C(=O)— together.

In a case where $R^{23}$ and $R^{24}$ in the general formula [4] each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, or in a case where $R^{23}$ and $R^{24}$ are bonded to each other an oxygen atom or a sulfur atom, it is preferable that the group represented by the general formula [2] and the group represented by the general formula [3] are bonded to any of $R^{16}$, $R^{18}$, $R^{19}$, and $R^{21}$. That is, in a case where $R^{23}$ and $R^{24}$ are bonded to each other through a carbonyl group, the group represented by the general formula [2] and the group represented by the general formula [3] may be bonded to any of $R^{15}$ to $R^{22}$. However, in a case where $R^{23}$ and $R^{24}$ are groups other than the above, it is desirable that the group represented by the general formula [2] and the group represented by the general formula [3] are bonded to any of $R^{16}$, $R^{18}$, $R^{19}$, and $R^{21}$.

As $R^{15}$ and $R^{16}$ in the general formula [4], a hydrogen atom and the group represented by the general formula [3] are preferable.

As $R^{17}$ and $R^{20}$ in the general formula [4], a hydrogen atom is preferable.

As $R^{18}$, $R^{19}$, and $R^{22}$ in the general formula [4], a hydrogen atom, the group represented by the general formula [2], and the group represented by the general formula [3] are preferable.

As $R^{21}$ in the general formula [4], a hydrogen atom, the group represented by the general formula [2], and the group represented by the general formula [3] are preferable. Among these, the hydrogen atom is more preferable.

As $R^{23}$ and $R^{24}$ in the general formula [4], a hydrogen atom or a group formed by $R^{23}$ and $R^{24}$ bonded to each other through an oxygen atom or a sulfur atom is preferable. Among these, a hydrogen atom or the group formed by $R^{23}$ and $R^{24}$ bonded to each other through a sulfur atom is more preferable.

Specific examples preferred as the compound (E) represented by the general formula [4] include compounds represented by the following general formulae [4-A] to [4-C].

General formula [4-A]

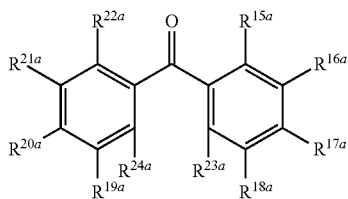

[4-A]

wherein $R^{16a}$, $R^{18a}$, $R^{19a}$, and $R^{21a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2] or the group represented by the general formula [3], and $R^{15a}$, $R^{17a}$, $R^{20a}$, $R^{22a}$, $R^{23a}$, and $R^{24a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of the groups represented by $R^{16a}$, $R^{18a}$, $R^{19a}$, and $R^{21a}$ is the group represented by the general formula [3].

General formula [4-B]

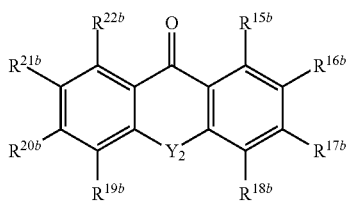

[4-B]

wherein $R^{16b}$, $R^{18b}$, $R^{19b}$, and $R^{21b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{15b}$, $R^{17b}$, $R^{20b}$, and $R^{22b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and $Y_2$ represents an oxygen atom or a sulfur atom, provided that at least one of the groups represented by $R^{16b}$, $R^{18b}$, $R^{19b}$, and $R^{21b}$ is the group represented by the general formula [3].

General formula [4-C]

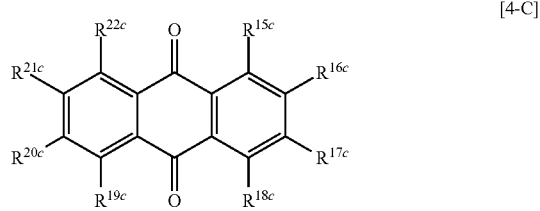

[4-C]

wherein $R^{15c}$ to $R^{22c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{15c}$ to $R^{22c}$ is the group represented by the general formula [3].

Specific examples of the alkyl group having 1 to 12 carbon atoms represented by $R^{15a}$ to $R^{24a}$ in the general formula [4-A], $R^{15b}$ to $R^{22b}$ in the general formula [4-B], and $R^{15c}$ to $R^{22c}$ in the general formula [4-C] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{15a}$ to $R^{24a}$ in the general formula [4-A], $R^{15b}$ to $R^{22b}$ in the general formula [4-B], and $R^{15c}$ to $R^{22c}$ in the general formula [4-C] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{15a}$ to $R^{24a}$ in the general formula [4-A], $R^{15b}$ to $R^{22b}$ in the general formula [4-B], and $R^{15c}$ to $R^{22c}$ in the general formula [4-C] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{15a}$ to $R^{24a}$ in the general formula [4-A], $R^{15b}$ to $R^{22b}$ in the general formula [4-B], and $R^{15c}$ to $R^{22c}$ in the general formula [4-C] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{15a}$ to $R^{24a}$ in the general formula [4-A], $R^{15b}$ to $R^{22b}$ in the general formula [4-B], and $R^{15c}$ to $R^{22c}$ in the general formula [4-C] are the same as the specific examples of the halogen atom represented by $R^1$ to $R^{10}$ in the general formula [1], and preferred specific examples are also the same.

As $R^{15a}$, $R^{17a}$, $R^{20a}$, $R^{22a}$, $R^{23a}$, and $R^{24a}$ in the general formula [4-A], a hydrogen atom is preferable.

As $R^{16a}$ in the general formula [4-A], the group represented by the general formula [3] is preferable.

As $R^{18a}$ in the general formula [4-A], a hydrogen atom, the group represented by the general formula [2], and the group represented by the general formula [3] are preferable.

As $R^{19a}$ and $R^{21a}$ in the general formula [4-A], a hydrogen atom, the group represented by the general formula [2], and the group represented by the general formula [3] are preferable. Among these, the hydrogen atom is more preferable.

Examples of the preferred combination of $R^{15a}$ to $R^{24a}$ in the general formula [4-A] include combinations represented by <1> to <6> in Table 4.

TABLE 4

| Combination | $R^{15a}$ | $R^{16a}$ | $R^{17a}$ | $R^{18a}$ | $R^{19a}$ | $R^{20a}$ | $R^{21a}$ | $R^{22a}$ | $R^{23a}$ | $R^{24a}$ |
|---|---|---|---|---|---|---|---|---|---|---|
| <1> | Hydrogen atom | General formula [3] | Hydrogen atom | Hydrogen atom | Hydrogen atom | Hydrogen atom | Hydrogen atom | Hydrogen atom | Hydrogen atom | Hydrogen atom |
| <2> | Hydrogen atom | General formula [3] | Hydrogen atom | Hydrogen atom | Hydrogen atom | Hydrogen atom | General formula [3] | Hydrogen atom | Hydrogen atom | Hydrogen atom |
| <3> | Hydrogen atom | General formula [3] | Hydrogen atom | General formula [3] | Hydrogen atom | Hydrogen atom | Hydrogen atom | Hydrogen atom | Hydrogen atom | Hydrogen atom |
| <4> | Hydrogen atom | General formula [3] | Hydrogen atom | General formula [3] | Hydrogen atom | Hydrogen atom | General formula [3] | Hydrogen atom | Hydrogen atom | Hydrogen atom |
| <5> | Hydrogen atom | General formula [3] | Hydrogen atom | General formula [3] | General formula [3] | Hydrogen atom | General formula [3] | Hydrogen atom | Hydrogen atom | Hydrogen atom |
| <6> | Hydrogen atom | General formula [3] | Hydrogen atom | General formula [3] | Hydrogen atom | Hydrogen atom | Hydrogen atom | Hydrogen atom | Hydrogen atom | Hydrogen atom |

As $R^{15b}$, $R^{17b}$, $R^{20b}$, and $R^{22b}$ in the general formula [4-B], a hydrogen atom is preferable.

As $R^{16b}$ in the general formula [4-B], the group represented by the general formula [3] is preferable.

As $R^{18b}$ in the general formula [4-B], a hydrogen atom, the group represented by the general formula [2], and the group represented by the general formula [3] are preferable.

As $R^{19b}$ and $R^{21b}$ in the general formula [4-B], a hydrogen atom, the group represented by the general formula [2], and the group represented by the general formula [3] are preferable. Among these, the hydrogen atom is more preferable.

AS $Y_2$ in the general formula [4-B], a sulfur atom is preferable.

Examples of the preferred combination of $Y_2$ and $R^{15b}$ to $R^{22b}$ in the general formula [4-B] include combinations represented by <1> to <12> in Table 5.

TABLE 5

| Combination | $Y_2$ | $R^{15b}$ | $R^{16b}$ | $R^{17b}$ | $R^{18b}$ | $R^{19b}$ | $R^{20b}$ | $R^{21b}$ | $R^{22b}$ |
|---|---|---|---|---|---|---|---|---|---|
| <1> | Oxygen atom | Hydrogen atom | General formula [3] | Hydrogen atom | Hydrogen atom | Hydrogen atom | Hydrogen atom | Hydrogen atom | Hydrogen atom |
| <2> | Oxygen atom | Hydrogen atom | General formula [3] | Hydrogen atom | Hydrogen atom | Hydrogen atom | Hydrogen atom | General formula [3] | Hydrogen atom |
| <3> | Oxygen atom | Hydrogen atom | General formula [3] | Hydrogen atom | General formula [3] | Hydrogen atom | Hydrogen atom | Hydrogen atom | Hydrogen atom |
| <4> | Oxygen atom | Hydrogen atom | General formula [3] | Hydrogen atom | General formula [3] | Hydrogen atom | Hydrogen atom | General formula [3] | Hydrogen atom |
| <5> | Oxygen atom | Hydrogen atom | General formula [3] | Hydrogen atom | General formula [3] | General formula [3] | Hydrogen atom | General formula [3] | Hydrogen atom |
| <6> | Oxygen atom | Hydrogen atom | General formula [3] | Hydrogen atom | General formula [2] | Hydrogen atom | Hydrogen atom | Hydrogen atom | Hydrogen atom |

TABLE 5-continued

| Combination | $Y_2$ | $R^{15b}$ | $R^{16b}$ | $R^{17b}$ | $R^{18b}$ | $R^{19b}$ | $R^{20b}$ | $R^{21b}$ | $R^{22b}$ |
|---|---|---|---|---|---|---|---|---|---|
| <7> | Sulfur atom | Hydrogen atom | General formula [3] | Hydrogen atom | Hydrogen atom | Hydrogen atom | Hydrogen atom | Hydrogen atom | Hydrogen atom |
| <8> | Sulfur atom | Hydrogen atom | General formula [3] | Hydrogen atom | Hydrogen atom | Hydrogen atom | Hydrogen atom | General formula [3] | Hydrogen atom |
| <9> | Sulfur atom | Hydrogen atom | General formula [3] | Hydrogen atom | General formula [3] | Hydrogen atom | Hydrogen atom | Hydrogen atom | Hydrogen atom |
| <10> | Sulfur atom | Hydrogen atom | General formula [3] | Hydrogen atom | General formula [3] | Hydrogen atom | Hydrogen atom | General formula [3] | Hydrogen atom |
| <11> | Sulfur atom | Hydrogen atom | General formula [3] | Hydrogen atom | General formula [3] | General formula [3] | Hydrogen atom | General formula [3] | Hydrogen atom |
| <12> | Sulfur atom | Hydrogen atom | General formula [3] | Hydrogen atom | General formula [2] | Hydrogen atom | Hydrogen atom | Hydrogen atom | Hydrogen atom |

As $R^{15c}$ and $R^{16c}$ in the general formula [4-C], a hydrogen atom and the group represented by the general formula [3] are preferable.

As $R^{17c}$ and $R^{20c}$ in the general formula [4-C], a hydrogen atom is preferable.

As $R^{18c}$, $R^{19c}$, and $R^{22c}$ in the general formula [4-C], a hydrogen atom, the group represented by the general formula [2], and the group represented by the general formula [3] are preferable.

As $R^{21c}$ in the general formula [4-C], a hydrogen atom, the group represented by the general formula [2], and the group represented by the general formula [3] are preferable. Among these, the hydrogen atom is more preferable.

Examples of the preferred combination of $R^{15c}$ to $R^{22c}$ in the general formula [4-C] include combinations represented by <1> to <12> in Table 6.

TABLE 6

| Combination | $R^{15c}$ | $R^{16c}$ | $R^{17c}$ | $R^{18c}$ | $R^{19c}$ | $R^{20c}$ | $R^{21c}$ | $R^{22c}$ |
|---|---|---|---|---|---|---|---|---|
| <1> | Hydrogen atom | General formula [3] | Hydrogen atom | Hydrogen atom | Hydrogen atom | Hydrogen atom | Hydrogen atom | Hydrogen atom |
| <2> | Hydrogen atom | General formula [3] | Hydrogen atom | Hydrogen atom | Hydrogen atom | Hydrogen atom | General formula [3] | Hydrogen atom |
| <3> | Hydrogen atom | General formula [3] | Hydrogen atom | General formula [3] | Hydrogen atom | Hydrogen atom | Hydrogen atom | Hydrogen atom |
| <4> | Hydrogen atom | General formula [3] | Hydrogen atom | General formula [3] | Hydrogen atom | Hydrogen atom | General formula [3] | Hydrogen atom |
| <5> | Hydrogen atom | General formula [3] | Hydrogen atom | General formula [3] | General formula [3] | Hydrogen atom | General formula [3] | Hydrogen atom |
| <6> | Hydrogen atom | General formula [3] | Hydrogen atom | General formula [2] | Hydrogen atom | Hydrogen atom | Hydrogen atom | Hydrogen atom |
| <7> | General formula [3] | Hydrogen atom | Hydrogen atom | Hydrogen atom | Hydrogen atom | Hydrogen atom | Hydrogen atom | Hydrogen atom |
| <8> | General formula [3] | Hydrogen atom | Hydrogen atom | General formula [3] | Hydrogen atom | Hydrogen atom | Hydrogen atom | Hydrogen atom |
| <9> | General formula [3] | Hydrogen atom | Hydrogen atom | Hydrogen atom | General formula [3] | Hydrogen atom | Hydrogen atom | Hydrogen atom |
| <10> | General formula [3] | Hydrogen atom | Hydrogen atom | Hydrogen atom | Hydrogen atom | Hydrogen atom | Hydrogen atom | General formula [3] |
| <11> | General formula [3] | Hydrogen atom | Hydrogen atom | General formula [3] | General formula [3] | Hydrogen atom | Hydrogen atom | General formula [3] |
| <12> | General formula [3] | General formula [3] | General formula [3] | General formula [3] | General formula [3] | General formula [3] | General formula [3] | General formula [3] |

Specific examples of the compound (E) represented by the general formula [4-A] include compounds represented by the following formulae [4-A1] to [4-A10].
Formulae [4-A1] to [4-A10]
[4-A1]
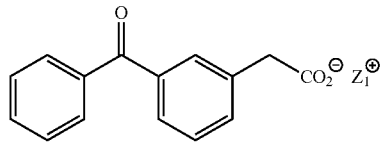
[4-A2]
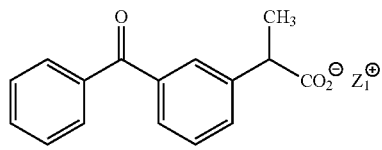
[4-A3]
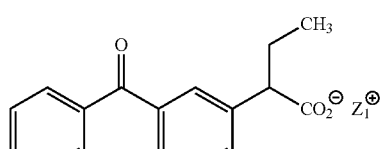
[4-A4]
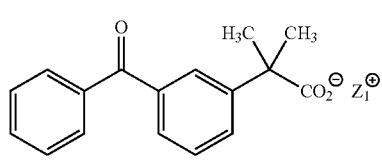
[4-A5]
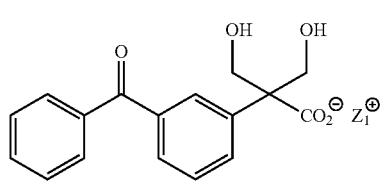
[4-A6]
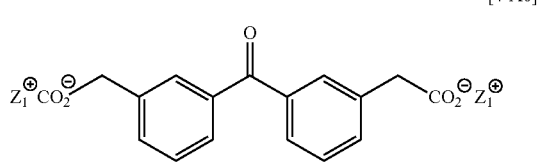
[4-A7]
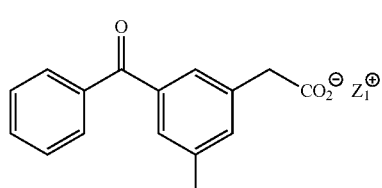
[4-A8]
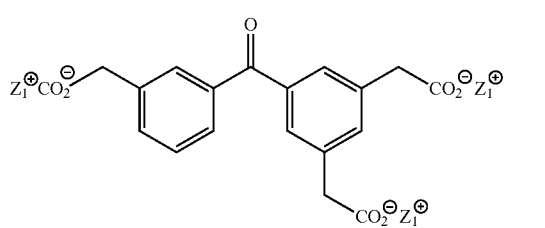
-continued
[4-A9]
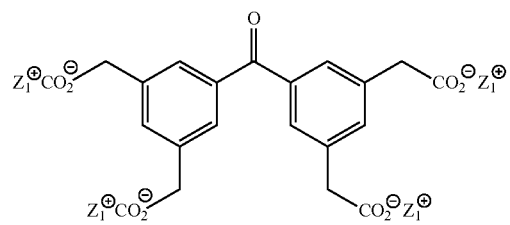
[4-A10]
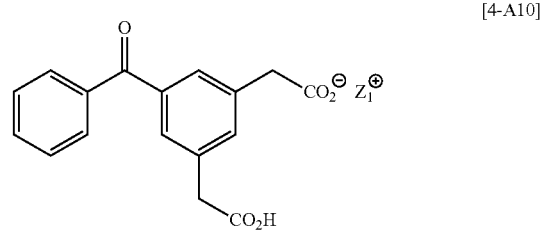
Specific examples of the compound (E) represented by the general formula [4-B] include compounds represented by the following formulae [4-B1] to [4-B12].
Formulae [4-B1] to [4-B12]
[4-B1]
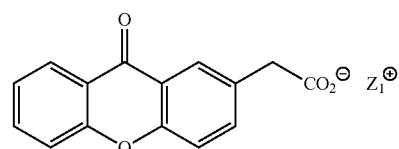
[4-B2]
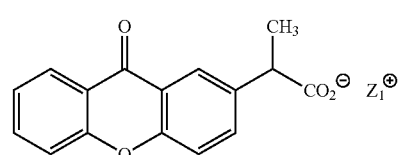
[4-B3]
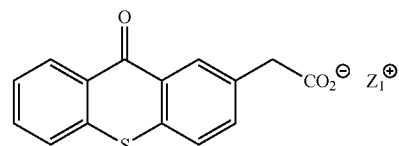
[4-B4]
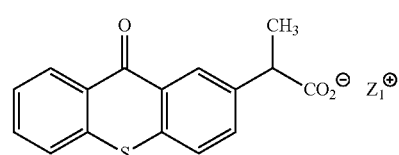
[4-B5]
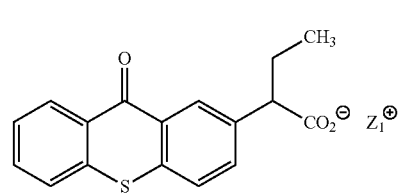

Specific examples of the compound (E) represented by the general formula [4-C] include compounds represented by the following formulae [4-C1] to [4-C14].

[4-C8]

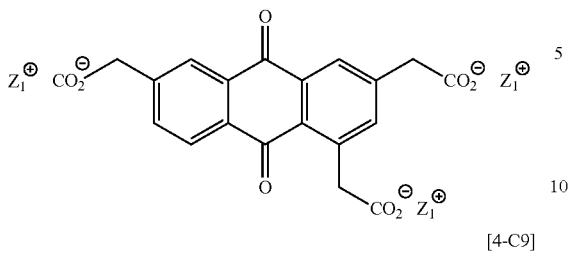

[4-C9]

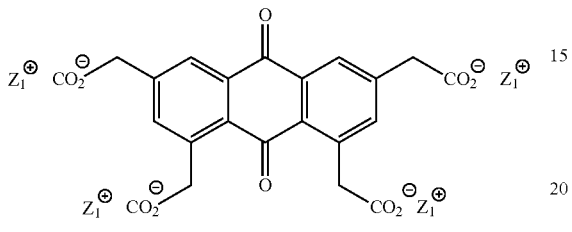

[4-C10]

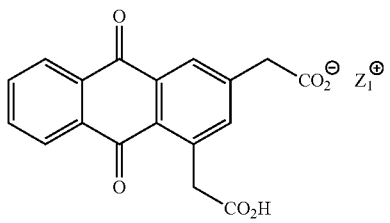

[4-C11]

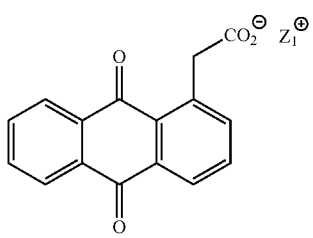

[4-C12]

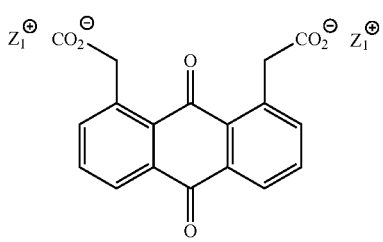

[4-C13]

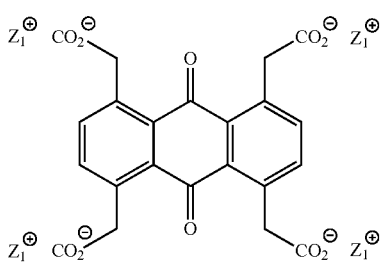

[4-C14]

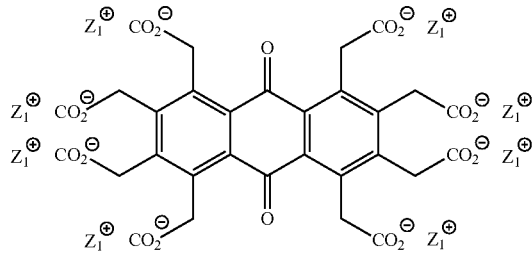

As the compound (E), from the viewpoint of ease of availability of raw materials at the time of manufacturing the compound (E) and economic efficiency, the compound represented by the general formula [4-A] and the compound represented by the general formula [4-B] are preferable. In addition, in a case where the UV absorber is used in the photocuring method of the present invention, among the compounds (E), sometimes the compound represented by the general formula [4-B] in which $Y_2$ represents a sulfur atom is preferable. Such a compound exhibits sensitivity with respect to light (active energy rays) having a main wavelength at 350 to 450 nm. Therefore, it is possible to allow the sol-gel reaction and the radical polymerization, the ene-thiol reaction, or the yne-thiol reaction to smoothly proceed without hindering the absorption of the light (active energy rays) by the UV absorber.

The compound represented by the formula [4-A10], the compound represented by the formula [4-B12], and the compound represented by the formula [4-C10] among the above formulae have a carbonyl group generating a radical by the irradiation of light (active energy rays), a group generating a base by being decarboxylated by the irradiation of light (active energy rays), and a carboxyl group which does not exhibit acidity by being decarboxylated by the irradiation of light (active energy rays). These compounds correspond to (A/E) compound having a carbonyl group generating a radical by photoirradiation, a carboxyl group decarboxylated by photoirradiation, and a group generating a base by being decarboxylated by photoirradiation. That is, these compounds are included in the compound (A/E) according to the photocuring method of the present invention.

Specific examples of the compound (A/E) include a compound represented by the following general formula [5].

General formula [5]

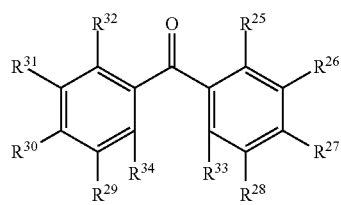

[5]

wherein $R^{25}$ to $R^{32}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by the following general formula [2], or a group represented by the following general formula [3], and $R^{33}$ and $R^{34}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{33}$ and $R^{34}$ are bonded to each other through an oxygen atom, a sulfur atom, or a carbonyl group, provided that at least one of the groups represented by $R^{25}$ to $R^{32}$ is the group represented by the following general formula [2], and at least one of the groups represented by $R^{25}$ to $R^{32}$ is the group represented by the following general formula [3].

General formula [2]

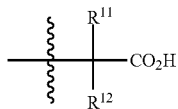

[2]

wherein $R^{11}$ and $R^{12}$ each independently represent a hydrogen atom, an alkyl group having 1 to 6 carbon atoms, or a hydroxyalkyl group having 1 to 6 carbon atoms.

General formula [3]

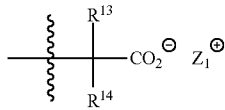

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

Specific examples of the alkyl group having 1 to 12 carbon atoms represented by $R^{25}$ to $R^{34}$ in the general formula [5] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{25}$ to $R^{34}$ in the general formula [5] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{25}$ to $R^{34}$ in the general formula [5] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{25}$ to $R^{34}$ in the general formula [5] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{25}$ to $R^{34}$ in the general formula [5] are the same as the specific examples of the halogen atom represented by $R^1$ to $R^{10}$ in the general formula [1], and preferred specific examples are also the same.

The state where $R^{33}$ and $R^{34}$ in the general formula [5] are bonded to each other through an oxygen atom, a sulfur atom, or a carbonyl group means that $R^{33}$ and $R^{34}$ form a group represented by —O—, —S—, or —C(=O)— together.

In a case where $R^{33}$ and $R^{34}$ in the general formula [5] each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, or in a case where $R^{33}$ and $R^{34}$ are bonded to each other through an oxygen atom or a sulfur atom, it is desirable that the group represented by the general formula [2] and the group represented by the general formula [3] are bonded to any of $R^{26}$, $R^{28}$, $R^{29}$, and $R^{31}$. That is, in a case where $R^{33}$ and $R^{34}$ are bonded to each other through a carbonyl group, the group represented by the general formula [2] and the group represented by the general formula [3] may be bonded to any of $R^{25}$ to $R^{32}$. However, in a case where $R^{33}$ and $R^{34}$ are groups other than the above, it is desirable that the group represented by the general formula [2] and the group represented by the general formula [3] are bonded to any of $R^{26}$, $R^{28}$, $R^{29}$, and $R^{31}$.

As $R^{25}$, $R^{26}$, $R^{28}$, $R^{29}$, and $R^{32}$ in the general formula [5], a hydrogen atom, the group represented by the general formula [2], and the group represented by the general formula [3] are preferable.

As $R^{27}$ and $R^{30}$ in the general formula [5], a hydrogen atom is preferable.

As $R^{31}$ in the general formula [5], a hydrogen atom, the group represented by the general formula [2], and the group represented by the general formula [3] are preferable. Among these, the hydrogen atom is preferable.

As $R^{33}$ and $R^{34}$ in the general formula [5], a hydrogen atom or a group formed by $R^{33}$ and $R^{34}$ bonded to each other through an oxygen atom or a sulfur atom is preferable. Among these, the hydrogen atom or the group formed by $R^{33}$ and $R^{34}$ bonded to each other through a sulfur atom is more preferable.

Specific examples preferred as the compound (A/E) represented by the general formula [5] include compounds represented by the following general formulae [5-A] to [5-C].

General formula [5-A]

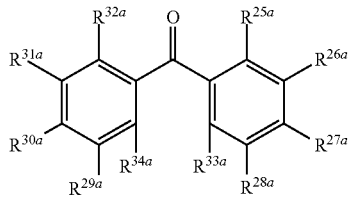

[5-A]

wherein $R^{26a}$, $R^{28a}$, $R^{29a}$, and $R^{31a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], and $R^{25a}$, $R^{27a}$, $R^{30a}$, $R^{32a}$, $R^{33a}$, and $R^{34a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of the groups represented by $R^{26a}$, $R^{28a}$, $R^{29a}$, and $R^{31a}$ is the group represented by the general formula [2], and at least one of the groups represented by $R^{26a}$, $R^{28a}$, $R^{29a}$, and $R^{31a}$ is the group represented by the general formula [3].

General formula [5-B]

[5-B]

wherein $R^{26b}$, $R^{28b}$, $R^{29b}$, and $R^{31b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{25b}$, $R^{27b}$, $R^{30b}$, and $R^{32b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and $Y_3$ represents an oxygen atom or a sulfur atom, provided that at least one of the groups represented by $R^{26b}$, $R^{28b}$, $R^{29b}$, and $R^{31b}$ is the group represented by the general formula [2], and at least one of the groups represented by $R^{26b}$, $R^{28b}$, $R^{29b}$, and $R^{31b}$ is the group represented by the general formula [3].

General formula [5-C]

[5-C]

wherein $R^{25c}$ to $R^{32c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{25c}$ to $R^{32c}$ is the group represented by the general formula [2], and at least one of the groups represented by $R^{25c}$ to $R^{32c}$ is the group represented by the general formula [3].

Specific examples of the alkyl group having 1 to 12 carbon atoms represented by $R^{25a}$ to $R^{34a}$ in the general formula [5-A], $R^{25b}$ to $R^{32b}$ in the general formula [5-B], and $R^{25c}$ to $R^{32c}$ in the general formula [5-C] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{25a}$ to $R^{34a}$ in the general formula [5-A], $R^{25b}$ to $R^{32b}$ in the general formula [5-B], and $R^{25c}$ to $R^{32c}$ in the general formula [5-C] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{25a}$ to $R^{34a}$ in the general formula [5-A], $R^{25b}$ to $R^{32b}$ in the general formula [5-B], and $R^{25c}$ to $R^{32c}$ in the general formula [5-C] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{25a}$ to $R^{34a}$ in the general formula [5-A], $R^{25b}$ to $R^{32b}$ in the general formula [5-B], and $R^{25c}$ to $R^{32c}$ in the general formula [5-C] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{25a}$ to $R^{34a}$ in the general formula [5-A], $R^{25b}$ to $R^{32b}$ in the general formula [5-B], and $R^{25c}$ to $R^{32c}$ in the general formula [5-C] are the same as the specific examples of the halogen atom represented by $R^1$ to $R^{10}$ in the general formula [1], and preferred specific examples are also the same.

As $R^{25a}$, $R^{27a}$, $R^{30a}$, $R^{32a}$, $R^{33a}$, and $R^{34a}$ in the general formula [5-A], a hydrogen atom is preferable.

As $R^{26a}$ and $R^{28a}$ in the general formula [5-A], the group represented by the general formula [2] and the group represented by the general formula [3] are preferable.

As $R^{29a}$ and $R^{31a}$ in the general formula [5-A], a hydrogen atom, the group represented by the general formula [2], and the group represented by the general formula [3] are preferable. Among these, the hydrogen atom is more preferable.

Examples of the preferred combination of $R^{25a}$ to $R^{34a}$ in the general formula [5-A] include combinations represented by <1> and <2> in Table 7.

TABLE 7

| Combination | $R^{26a}$ | $R^{26b}$ | $R^{27a}$ | $R^{28a}$ | $R^{29a}$ | $R^{30a}$ | $R^{31a}$ | $R^{32a}$ | $R^{33a}$ | $R^{34a}$ |
|---|---|---|---|---|---|---|---|---|---|---|
| <1> | Hydrogen atom | General formula [2] | Hydrogen atom | General formula [3] | Hydrogen atom | Hydrogen atom | Hydrogen atom | Hydrogen atom | Hydrogen atom | Hydrogen atom |
| <2> | Hydrogen atom | General formula [3] | Hydrogen atom | General formula [2] | Hydrogen atom | Hydrogen atom | Hydrogen atom | Hydrogen atom | Hydrogen atom | Hydrogen atom |

As $R^{25b}$, $R^{27b}$, $R^{30b}$, and $R^{32b}$ in the general formula [5-B], a hydrogen atom is preferable.

As $R^{26b}$ and $R^{28b}$ in the general formula [5-B], the group represented by the general formula [2] and the group represented by the general formula [3] are preferable.

As $R^{29b}$ and $R^{31b}$ in the general formula [5-B], a hydrogen atom, the group represented by the general formula [2], and the group represented by the general formula [3] are preferable. Among these, the hydrogen atom is more preferable.

As $Y_3$ in the general formula [5-B], a sulfur atom is preferable.

Examples of the preferred combination of $Y_3$ and $R^{25b}$ to $R^{32b}$ in the general formula [5-B] include combinations represented by <1> to <4> in Table 8.

TABLE 8

| Combination | $Y_3$ | $R^{25b}$ | $R^{26b}$ | $R^{27b}$ | $R^{28b}$ | $R^{29b}$ | $R^{30b}$ | $R^{31b}$ | $R^{32b}$ |
|---|---|---|---|---|---|---|---|---|---|
| <1> | Oxygen atom | Hydrogen atom | General formula [2] | Hydrogen atom | General formula [3] | Hydrogen atom | Hydrogen atom | Hydrogen atom | Hydrogen atom |
| <2> | Oxygen atom | Hydrogen atom | General formula [3] | Hydrogen atom | General formula [2] | Hydrogen atom | Hydrogen atom | Hydrogen atom | Hydrogen atom |
| <3> | Sulfur atom | Hydrogen atom | General formula [2] | Hydrogen atom | General formula [3] | Hydrogen atom | Hydrogen atom | Hydrogen atom | Hydrogen atom |
| <4> | Sulfur atom | Hydrogen atom | General formula [3] | Hydrogen atom | General formula [2] | Hydrogen atom | Hydrogen atom | Hydrogen atom | Hydrogen atom |

As $R^{25c}$ and $R^{26c}$ in the general formula [5-C], a hydrogen atom, the group represented by the general formula [2], and the group represented by the general formula [3] are preferable.

As $R^{27c}$, $R^{30c}$, and $R^{31c}$ in the general formula [5-C], a hydrogen atom is preferable.

As $R^{28c}$, $R^{29c}$, and $R^{32c}$ in the general formula [5-C], a hydrogen atom, the group represented by the general formula [2], and the group represented by the general formula [3] are preferable.

Examples of the preferred combination of $R^{25c}$ to $R^{32c}$ in the general formula [5-C] include combinations represented by <1> to <6> in Table 9.

TABLE 9

| Combination | $R^{25c}$ | $R^{26c}$ | $R^{27c}$ | $R^{28c}$ | $R^{29c}$ | $R^{30c}$ | $R^{31c}$ | $R^{32c}$ |
|---|---|---|---|---|---|---|---|---|
| <1> | Hydrogen atom | General formula [2] | Hydrogen atom | General formula [3] | Hydrogen atom | Hydrogen atom | Hydrogen atom | Hydrogen atom |
| <2> | Hydrogen atom | General formula [3] | Hydrogen atom | General formula [2] | Hydrogen atom | Hydrogen atom | Hydrogen atom | Hydrogen atom |
| <3> | General formula [2] | Hydrogen atom | Hydrogen atom | Hydrogen atom | General formula [3] | Hydrogen atom | Hydrogen atom | Hydrogen atom |
| <4> | General formula [3] | Hydrogen atom | Hydrogen atom | Hydrogen atom | General formula [2] | Hydrogen atom | Hydrogen atom | Hydrogen atom |
| <5> | General formula [2] | Hydrogen atom | Hydrogen atom | Hydrogen atom | Hydrogen atom | Hydrogen atom | Hydrogen atom | General formula [3] |
| <6> | General formula [3] | Hydrogen atom | Hydrogen atom | Hydrogen atom | Hydrogen atom | Hydrogen atom | Hydrogen atom | General formula [2] |

Specific examples of the compound (A/E) represented by the general formula general formula [5-A] include the compounds represented by the formula [1-A10] and the formula [4-A10]. That is, the compounds represented by the formula [1-A10] and the formula [4-A10] correspond to both the compound (A) and the compound (E).

Specific examples of the compound (A/E) represented by the general formula general formula [5-B] include the compounds represented by the formula [1-B12] and the formula [4-B12]. That is, the compounds represented by the formula [1-B12] and the formula [4-B12] correspond to both the compound (A) and the compound (E).

Specific examples of the compound (A/E) represented by the general formula general formula [5-C] include the compounds represented by the formula [1-C10] and the formula [4-C10]. That is, the compounds represented by the formula [1-C10] and the formula [4-C10] correspond to both the compound (A) and the compound (E).

In the compound represented by the general formula [5], in a case where pKa of the group represented by the general formula [2] (carboxylic acid: $-CR^{11}R^{12}CO_2H$) bonded to each R in the general formulae [5-A] to [5-C] is the same as or smaller than pKa of a carboxylic acid ($-CR^{13}R^{14}CO_2H$) as the source of a carboxylate anion ($-CR^{13}R^{14}CO_2-$) in the group represented by the general formula [3], the cation represented by $Z_1^+$ in the general formula [3] is exchanged with a proton of the group represented by the general formula [2] in some cases. In this case, an equilibrium relationship is established between the two kinds of compounds. More specifically, the equilibrium relationship is established between the compound represented by the formula [1-A10] and the compound represented by the formula [4-A10], between the compound represented by the formula [1-B12] and the compound represented by the formula [4-B12], and between the compound represented by the formula [1-C10] and the compound represented by the formula [4-C10].

The cation represented by $Z_1^+$ in the general formula [3] in the general formula [1], the general formula [4], and the general formula [5] represents any of cations including "an amidinium cation, a guanidium cation, a biguanidinium cation, and a phosphazenium cation". Specific examples of these cations include "amidinium cation" represented by the following general formula [6], "guanidium cation" represented by the following general formula [7], "biguanidinium cation" represented by the following general formula [8], and "phosphazenium cation" represented by the following general formula [9].

General formula [6]

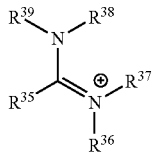
[6]

wherein $R^{35}$ to $R^{39}$ each independently represent a hydrogen atom or an alkyl group having 1 to 12 carbon atoms; or represent a state where $R^{35}$ and $R^{39}$ and/or $R^{37}$ and $R^{38}$ are bonded to each other through an alkylene group having 2 to 8 carbon atoms.

General formula [7]

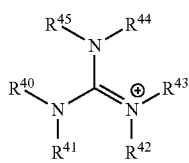
[7]

wherein $R^{40}$ to $R^{45}$ each independently represent a hydrogen atom or an alkyl group having 1 to 12 carbon atoms; or represent a state where $R^{40}$ and $R^{45}$ and/or $R^{41}$ and $R^{42}$ are bonded to each other through an alkylene group having 2 to 4 carbon atoms.

General formula [8]

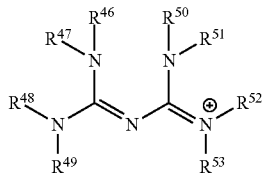
[8]

wherein $R^{46}$ to $R^{50}$ and $R^{53}$ each independently represent a hydrogen atom or an alkyl group having 1 to 12 carbon atoms, and $R^{51}$ and $R^{52}$ each independently represent a hydrogen atom; an alkyl group having 1 to 12 carbon atoms; or an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group, or represent a state where $R^{51}$ and $R^{52}$ are bonded to each other through an alkylene group having 2 to 4 carbon atoms.

General formula [9]

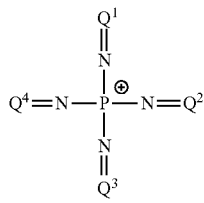
[9]

wherein $Q^1$ to $Q^4$ each independently represent a group represented by the following general formula [10] or a group represented by the following general formula [11].

General formula [10]

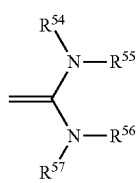
[10]

wherein $R^{54}$ to $R^{57}$ each independently represent a hydrogen atom or an alkyl group having 1 to 6 carbon atoms.

General formula [11]

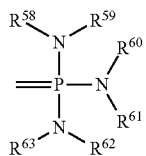
[11]

wherein $R^{58}$ to $R^{63}$ each independently represent a hydrogen atom or an alkyl group having 1 to 6 carbon atoms.

Specific examples of the alkyl group having 1 to 12 carbon atoms represented by $R^{35}$ to $R^{39}$ in the general formula [6] are the same as the specific examples of the alkyl group having 1 to 12 carbon atoms represented by $R^1$ to $R^{10}$ in the general formula [1], and preferred specific examples are also the same.

In a case where "$R^{35}$ and $R^{39}$ and/or $R^{37}$ and $R^{38}$ are bonded to each other through an alkylene group having 2 to 8 carbon atoms" in the general formula [6], the alkylene group having 2 to 8 carbon atoms may be any of linear or branched alkylene groups. Examples thereof include a dimethylene group (ethylene group), a trimethylene group, a propylene group, a tetramethylene group, a 1-methyltrimethylene group, a 2-methyltrimethylene group, a 1,2-dimethyldimethylene group (1,2-dimethylethylene group), a 1,1-dimethyldimethylene group (1,1-dimethylethylene group), an ethyldimethylene group (ethylethylene group), a pentamethylene group, a hexamethylene group, a heptamethylene group, an octamethylene group, and the like. Among these alkylene groups, the trimethylene group, the tetramethylene group, and the pentamethylene group which are linear alkylene groups having 3 to 5 carbon atoms are preferable.

In a case where "$R^{35}$ and $R^{39}$ are bonded to each other through an alkylene group having 2 to 8 carbon atoms" in the general formula [6], the alkylene group and a —C—N— group bonded to the alkylene group form a 4- to 10-membered cyclic structure.

Specific examples of the cyclic structure include a pyrrolidine ring (tetramethylene imine ring), a 2-methylpyrrolidine ring, a 3-methylpyrrolidine ring, a piperidine ring (pentamethylene imine ring), a 2-methylpiperidine ring, a 3-methylpiperidine ring, a 4-methylpiperidine ring, a hexamethylene imine ring, a heptamethylene imine ring, an octamethylene imine ring, a nonamethylene imine ring, a decamethylene imine ring, and the like. Among these cyclic structures, the pyrrolidine ring (tetramethylene imine ring) and the hexamethylene imine ring are preferable.

In a case where "$R^{37}$ and $R^{38}$ are bonded to each other through an alkylene group having 2 to 8 carbon atoms" in the general formula [6], the alkylene group and a —N=C—N— group bonded to the alkylene group form a 5- to 11-membered cyclic structure.

Specific examples of the cyclic structure include an imidazoline ring, a 1,4,5,6-tetrahydropyrimidine ring, a 4-methylimidazoline ring, a 5-methylimidazoline ring, a 1,3-diaza-2-cycloheptene ring, a 1,4,5,6-tetrahydro-4-methylpyrimidine ring, a 1,4,5,6-tetrahydro-5-methylpyrimidine ring, a 1,4,5,6-tetrahydro-6-methylpyrimidine ring, a 4-ethylimidazoline ring, a 5-ethylimidazoline ring, a 4,4-dimethylimidazoline ring, a 4,5-dimethylimidazoline ring, and a 5,5-dimethylimidazoline ring. Among these cyclic structures, the imidazoline ring is preferable.

As $R^{35}$ and $R^{39}$ in the general formula [6], a hydrogen atom, an alkyl group having 1 to 12 carbon atoms, or a group formed by $R^{35}$ and $R^{39}$ bonded to each other through an alkylene group having 2 to 8 carbon atoms is preferable. Among these, the group formed by $R^{35}$ and $R^{39}$ bonded to each other through an alkylene group having 2 to 8 carbon atoms is more preferable.

As $R^{36}$ in the general formula [6], a hydrogen atom and an alkyl group having 1 to 12 carbon atoms are preferable, and the hydrogen atom is more preferable.

As $R^{37}$ and $R^{38}$ in the general formula [6], an alkyl group having 1 to 12 carbon atoms or a group formed by $R^{37}$ and $R^{38}$ bonded to each other through an alkylene group having 2 to 8 carbon atoms is preferable. Among these, the group formed by $R^{37}$ and $R^{38}$ bonded to each other through an alkylene group having 2 to 8 carbon atoms is more preferable.

In the general formula [6], it is preferable that both of $R^{35}$ and $R^{39}$ and $R^{37}$ and $R^{38}$ are bonded to each other through an alkylene group having 2 to 8 carbon atoms. That is, as the amidinium cation represented by the general formula [6], a cation forming a fused ring is preferable.

Specific examples of the alkyl group having 1 to 12 carbon atoms represented by $R^{40}$ to $R^{45}$ in the general formula [7] are the same as the specific examples of the alkyl group having 1 to 12 carbon atoms represented by $R^1$ to $R^{10}$ in the general formula [1], and preferred specific examples are also the same.

In a case where "$R^{40}$ and $R^{45}$ and/or $R^{41}$ and $R^{42}$ are bonded to each other through an alkylene group having 2 to 4 carbon atoms" in the general formula [7], the alkylene group having 2 to 4 carbon atoms may be any of linear or branched alkylene groups. Examples thereof include a dimethylene group (ethylene group), a trimethylene group, a propylene group, a tetramethylene group, a 1-methyltrimethylene group, a 2-methyltrimethylene group, a 1,2-dimethyldimethylene group (1,2-dimethylethylene group), a 1,1-dimethyldimethylene group (1,1-dimethylethylene group), an ethyldimethylene group (ethylethylene group), and the like. Among these alkylene groups, the trimethylene group is preferable.

In a case where "$R^{40}$ and $R^{45}$ are bonded to each other through an alkylene group having 2 to 4 carbon atoms" in the general formula [7], the alkylene group and a —N—C—N— group bonded to the alkylene group form a 5- to 7-membered cyclic structure.

Specific examples of the cyclic structure include an imidazolidine ring, a hexahydropyrimidine ring, a 4-methylimidazolidine ring, a 1,3-diazacycloheptane ring, a hexahydro-4-methylpyrimidine ring, a hexahydro-5-methylpyrimidine ring, a 4-ethylimidazolidine ring, a 4,4-dimethylimidazolidine ring, a 4,5-dimethylimidazolidine ring, and the like. Among these cyclic structures, the hexahydropyrimidine ring is preferable.

In a case where "$R^{41}$ and $R^{42}$ are bonded to each other through an alkylene group having 2 to 4 carbon atoms" in the general formula [7], the alkylene group and a —N—C=N— group bonded to the alkylene group form a 5- to 7-membered cyclic structure together.

Specific examples of the cyclic structure include an imidazoline ring, 1,4,5,6-tetrahydropyrimidine ring, a 4-methylimidazoline ring, a 5-methylimidazoline ring, a 1,3-diaza-2-cycloheptene ring, a 1,4,5,6-tetrahydro-4-methylpyrimidine ring, a 1,4,5,6-tetrahydro-5-methylpyrimidine ring, a 1,4,5,6-tetrahydro-6-methylpyrimidine ring, a 4-ethylimidazoline ring, a 5-ethylimidazoline ring, a 4,4-dimethylimidazoline ring, a 4,5-dimethylimidazoline ring, and a 5,5-dimethylimidazoline ring. Among these cyclic structures, the 1,4,5,6-tetrahydropyrimidine ring is preferable.

As $R^{40}$ and $R^{45}$ in the general formula [7], an alkyl group having 1 to 12 carbon atoms or a group formed by $R^{40}$ and $R^{45}$ bonded to each other through an alkylene group having 2 to 4 carbon atoms is preferable.

As $R^{41}$ and $R^{42}$ in the general formula [7], an alkyl group having 1 to 12 carbon atoms or a group formed by $R^{41}$ and $R^{42}$ bonded to each other through an alkylene group having 2 to 4 carbon atoms is preferable.

In a case where $R^{40}$ and $R^{45}$ in the general formula [7] are bonded to each other through an alkylene group having 2 to 4 carbon atoms, it is preferable that $R^{41}$ and $R^{42}$ are bonded to each other through an alkylene group having 2 to 4 carbon atoms. That is, in a case where $R^{40}$ and $R^{45}$ form a cyclic structure by being bonded to each other, it is preferable that $R^{41}$ and $R^{42}$ also form a cyclic structure by being bonded to each other such that the guanidium cation represented by the general formula [7] becomes a cation forming a fused ring.

As $R^{43}$ in the general formula [7], a hydrogen atom and an alkyl group having 1 to 12 carbon atoms are preferable. Among these, the hydrogen atom is more preferable.

As $R^{44}$ in the general formula [7], a hydrogen atom and an alkyl group having 1 to 12 carbon atoms are preferable.

Specific examples of the alkyl group having 1 to 12 carbon atoms represented by $R^{46}$ to $R^{53}$ in the general formula [8] are the same as the specific examples of the alkyl group having 1 to 12 carbon atoms represented by $R^1$ to $R^{10}$ in the general formula [1].

Among these alkyl groups, as the alkyl group represented by $R^{46}$ to $R^{50}$ and $R^{53}$, a linear, branched, or cyclic alkyl group having 1 to 6 carbon atoms is preferable. Among these, a linear, branched, or cyclic alkyl group having 1 to 4 carbon atoms is preferable, and a methyl group is particularly preferable. Specific preferred examples of these are also the same as the specific examples of the preferred alkyl group represented by $R^1$ to $R^{10}$ in the general formula [1].

In addition, as the alkyl group represented by $R^{51}$ and $R^{52}$, a linear, branched, or cyclic alkyl group having 2 to 8 carbon atoms is preferable. Among these, a linear, branched, or cyclic alkyl group having 3 to 6 carbon atoms is preferable, and a branched or cyclic alkyl group having 3 to 6 carbon atoms is particularly preferable.

As $R^{46}$ to $R^{49}$ in the general formula [8], an alkyl group having 1 to 12 carbon atoms is preferable. Particularly, it is more preferable that all of $R^{46}$ to $R^{49}$ are alkyl groups having 1 to 12 carbon atoms.

As $R^{50}$ and $R^{53}$ in the general formula [8], a hydrogen atom is preferable. Particularly, it is more preferable that both of $R^{50}$ and $R^{53}$ are hydrogen atoms.

In "an alkyl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], "aryl group having 6 to 14 carbon atoms that may have a substituent" means that the aryl group includes both of an aryl group having 6 to 14 carbon atoms that does not have a substituent and an aryl group having 6 to 14 carbon atoms that has a substituent.

In "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the aryl group having 6 to 14 carbon atoms may be a monocyclic aryl group or a fused polycyclic aryl group. Examples thereof include a phenyl group, a naphthyl group, an anthracenyl group, and the like. Among these aryl groups, the phenyl group is preferable. It should be noted that the number of carbon atoms in the aryl group means the number of carbon atoms constituting the aryl group, and the number of carbon atoms constituting a substituent is not included in the number of carbon atoms represented by "6 to 14 carbon atoms" in "aryl group having 6 to 14 carbon atoms".

In "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the alkyl group having 1 to 6 carbon atoms may be a linear, branched, or cyclic alkyl group. Examples thereof include a methyl group, an ethyl group, a n-propyl group, an isopropyl group, a cyclopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, and the like. Among these alkyl groups, a linear, branched, or cyclic alkyl group having 1 to 3 carbon atoms is preferable.

In "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the alkoxy group having 1 to 6 carbon atoms may be a linear, branched, or cyclic alkoxy group. Examples thereof include a methoxy group, an ethoxy group, a n-propoxy group, an isopropoxy group, a cyclopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, and the like. Among these alkyloxy groups, a linear, branched, or cyclic alkoxy group having 1 to 3 carbon atoms is preferable.

In "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the alkylthio group having 1 to 6 carbon atoms may be a linear, branched, or cyclic alkylthio group. Examples thereof include a methylthio group, an ethylthio group, a n-propylthio group, an isopropylthio group, a cyclopropylthio group, a n-butylthio group, an isobutylthio group, a sec-butylthio group, a tert-butylthio group, a cyclobutylthio group, a n-pentylthio group, an isopentylthio group, a sec-pentylthio group, a tert-pentylthio group, a neopentylthio group, a 2-methylbutylthio group, a 1,2-dimethylpropylthio group, a 1-ethylpropylthio group, a cyclopentylthio group, a n-hexylthio group, an isohexylthio group, a sec-hexylthio group, a tert-hexylthio group, a neohexylthio group, a 2-methylpentylthio group, a 1,2-dimethylbutylthio group, a 2,3-dimethylbutylthio group, a 1-ethylbutylthio group, a cyclohexylthio group, and the like. Among these alkylthio groups, a linear, branched, or cyclic alkylthio group having 1 to 3 carbon atoms is preferable.

In "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the dialkylamino group having 2 to 12 carbon atoms may be a linear, branched, or cyclic dialkylamino group. Examples thereof a N,N-dimethylamino group, a N,N-diethylamino group, a N,N-di-n-propylamino group, a N,N-diisopropylamino group, a N,N-dicyclopropylamino group, a N,N-di-n-butylamino group, a N,N-diisobutylamino group, a N,N-di-sec-butylamino group, a N,N-di-tert-butylamino group, a N,N-dicyclobutylamino group, a N,N-di-n-pentylamino group, a N,N-diisopentylamino group, a N,N-di-sec-pentylamino group, a N,N-di-tert-pentylamino group, a N,N-dineopentylamino group, a N,N-di(2-methylbutyl)amino group, a N,N-bis(1,2-dimethylpropyl)amino group, a N,N-di(1-ethylpropyl)amino group, a N,N-dicyclopentylamino group, a N,N-di-n-hexylamino group, a N,N-diisohexylamino group, a N,N-di-sec-hexylamino group, a N,N-di-tert-hexylamino group, a N,N-dineohexylamino group, a N,N-di(2-methylpentyl)amino group, a N,N-bis(1,2-dimethylbutyl)amino group, a N,N-bis(2,3-dimethylbutyl)amino group, a N,N-di(1-ethylbutyl)amino group, a N,N-dicyclohexylamino group, a N,N-ethylmethylamino group, a N,N-methyl-n-propylamino group, a N,N-methylisopropylamino group, a N,N-methylcyclopropylamino group, a N,N-n-butylmethylamino group, a N,N-isobutylmethylamino group, a N,N-sec-butylmethylamino group, a N,N-tert-butylmethylamino group, a N,N-cyclobutylmethylamino group, a N,N-methyl-n-pentylamino group, a N,N-n-hexylmethylamino group, a N,N-n-heptylmethylamino group, a N,N-methyl-n-octylamino group, a N,N-methyl-n-nonylamino group, a N,N-n-decylmethylamino group, a N,N-methyl-n-undecylamino group, a N,N-ethyl-n-propylamino group, a N,N-ethylisopropylamino group, a N,N-ethylcyclopropylamino group, a N,N-n-butylethylamino group, a N,N-isobutylethylamino group, a N,N-sec-butylethylamino group, a N,N-tert-butylethylamino group, a N,N-cyclobutylethylamino group, a N,N-ethyl-n-pentylamino group, a N,N-ethyl-n-hexylamino group, a N,N-ethyl-n-heptylamino group, a N,N-ethyl-n-octylamino group, a N,N-ethyl-n-nonylamino group, a N,N-ethyl-n-decylamino group, a N,N-n-propylisopropylamino group, a N,N-n-propylcyclopropylamino group, a N,N-n-butyl-n-propylamino group, a N,N-isobutyl-n-propylamino group, a N,N-sec-butyl-n-propylamino group, a N,N-tert-butyl-n-propylamino group, a N,N-cyclobutyl-n-propylamino group, a N,N-n-pentyl-n-propylamino group, a N,N-n-hexyl-n-propylamino group, a N,N-n-heptyl-n-propylamino group, a N,N-n-octyl-n-propylamino group, a N,N-n-nonyl-n-propylamino group, a N,N-isopropylcyclopropylamino group, a N,N-n-butylisopropylamino group, a N,N-isobutylisopropylamino group, a N,N-sec-butylisopropylamino group, a N,N-tert-butylisopropylamino group, a N,N-cyclobutylisopropylamino group, a N,N-n-pentylisopropylamino group, a N,N-n-hexylisopropylamino group, a N,N-n-heptylisopropylamino group, a N,N-n-octylisopropylamino group, a N,N-n-nonylisopropylamino group, a N,N-n-butylcyclopropylamino group, a N,N-isobutylcyclopropylamino group, a N,N-sec-butylcyclopropylamino group, a N,N-tert-butylcyclopropylamino group, a N,N-cyclobutylcyclopropylamino group, a N,N-n-pentylcyclopropylamino group, a N,N-n-hexylcyclopropylamino group, a N,N-n-heptylcyclopropylamino group, a N,N-n-octylcyclopropylamino group, a N,N-n-nonylcyclopropylamino group, a N,N-n-butylisobutylamino group, a N,N-n-butyl-sec-butylamino group, a N,N-n-butyl-tert-butylamino group, a N,N-n-butylcyclobutylamino group, a N,N-n-butyl-n-pentylamino group, a N,N-n-butyl-n-hexylamino group, a N,N-n-butyl-n-heptylamino group, a N,N-n-butyl-n-octylamino group, a N,N-isobutyl-sec-butylamino group, a N,N-isobutyl-tert-butylamino group, a N,N-isobutylcyclobutylamino group, a N,N-isobutyl-n-pentylamino group, a N,N-isobutyl-n-hexylamino group, a N,N-isobutyl-n-heptylamino group, a N,N-isobutyl-n-octylamino group, a N,N-sec-butyl-tert-butylamino group, a N,N-sec-butylcyclobutylamino group, a N,N-sec-butyl-n-pentylamino group, a N,N-sec-butyl-n-hexylamino group, a N,N-sec-butyl-n-pentylamino group, a N,N-sec-butyl-n-octylamino group, a N,N-tert-butylcyclobutylamino group, a N,N-tert-butyl-n-pentylamino group, a N,N-tert-butyl-n-hexylamino group, a N,N-tert-butyl-n-heptylamino group, a N,N-tert-butyl-n-octylamino group, a N,N-cyclobutyl-n-pentylamino group, a N,N-cyclobutyl-n-hexylamino group, a N,N-cyclobutyl-n-heptylamino group, a N,N-cyclobutyl-n-octylamino group, a N,N-n-hexyl-n-pentylamino group, a N,N-n-heptyl-n-pentylamino group, and the like. Among these dialkylamino groups, a linear, branched, or cyclic dialkylamino group having 2 to 6 carbon atoms is preferable.

Examples of the halogen atom in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8] include a fluorine atom, a chlorine atom, a bromine atom, an iodine atom, and the like. Among these, the fluorine atom and the chlorine atom are preferable.

As "a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the alkyl group having 1 to 6 carbon atoms, the alkoxy group having 1 to 6 carbon atoms, the halogen atom, and the nitro group are preferable. Among these, the alkyl group having 1 to 6 carbon atoms and the alkoxy group having 1 to 6 carbon atoms are more preferable, and the alkyl group having 1 to 6 carbon atoms is even more preferable.

In "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8], the number of substituents on the aryl group having 6 to 14 carbon atoms is, for example, an integer of 0 (unsubstituted) to 9. The number of substituents is preferably an integer of 0 (unsubstituted) to 5, and even more preferably an integer of 0 (unsubstituted) to 2.

In a case where the aryl group having 6 to 14 carbon atoms in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8] is a phenyl group, the substitution position of the substituent on the phenyl group may be any of position 2 to position 6. Among these, position 2, position 4, or position 6 is preferable, and position 2 or position 6 is more preferable.

In a case where the aryl group having 6 to 14 carbon atoms in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8] is a naphthyl group, the binding position of a nitrogen atom, which is bonded to $R^{51}$ or $R^{52}$, on the naphthyl group may be any of position 1 or position 2.

In the naphthyl group, the substitution position of the substituent on the naphthyl group may be any of position 1 to position 8. Among these, position 1 to position 4 are preferable. Here, the substitution position does not overlap with the binding position of the nitrogen atom bonded to $R^{51}$ or $R^{52}$.

In a case where the aryl group having 6 to 14 carbon atoms in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8] is an anthracenyl group, the binding position of a nitrogen atom, which is bonded to $R^{51}$ or $R^{52}$, on the anthracenyl group may be any of position 1, position 2, and position 9, and preferably position 9.

In the anthracenyl group, in a case where the binding position of a nitrogen atom, which is bonded to $R^{51}$ or $R^{52}$, on the anthracenyl group is position 1 or position 2, the substitution position of the substituent on the anthracenyl group may be any of position 1 to position 10. Among these, position 1 to position 4 are preferable. Here, the substitution position does not overlap with the binding position of the nitrogen atom bonded to $R^{51}$ or $R^{52}$.

In the anthracenyl group, in a case where the binding position of a nitrogen atom, which is bonded to $R^{51}$ or $R^{52}$, on the anthracenyl group is position 9, the substitution position of the substituent on the anthracenyl group may be any of position 1 to position 8 and position 10. Among these, position 10 is preferable.

Specific examples of "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8] include an (unsubstituted) aryl group having 6 to 14 carbon atoms that does not have a substituent, such as a phenyl group, a naphthyl group, or an anthracenyl group; an aryl group having 6 to 14 carbon atoms substituted with an alkyl group having 1 to 6 carbon atoms (having an alkyl group having 1 to 6 carbon atoms), such as a 2-methylphenyl group, a 3-methylphenyl group, a 4-methylphenyl group, a 2,4-dimethylphenyl group, a 2,6-dimethylphenyl group, a 2,4,6-trimethylphenyl group, a 2,6-diethylphenyl group, a 2,6-di-n-propylphenyl group, a 2,6-diisopropylphenyl group, a 1-(2-methyl)naphthyl group, a 2-(1-methyl)naphthyl group, or a 9-(10-methyl)anthracenyl group; an aryl group having 6 to 14 carbon atoms substituted with an alkylthio group having 1 to 6 carbon atoms (having an alkylthio group having 1 to 6 carbon atoms), such as a 2-methylthiophenyl group, a 3-methylthiophenyl group, a 4-methylthiophenyl group, a 2,4-dimethylthiophenyl group, a 2,6-dimethylthiophenyl group, a 2,4,6-trimethylthiophenyl group, a 2,6-diethylthiophenyl group, a 2,6-di-n-propylthiophenyl group, a 2,6-diisopropylthiophenyl group, a 1-(2-methylthio)naphthyl group, a 2-(1-methylthio)naphthyl group, or a 9-(10-methylthio)anthracenyl group; an aryl group having 6 to 14 carbon atoms substituted with a dialkylamino group having 2 to 12 carbon atoms (having a dialkylamino group having 2 to 12 carbon atoms), such as a 2-(N,N-dimethylamino)phenyl group, a 3-(N,N-dimethylamino)phenyl group, a 4-(N,N-dimethylamino)phenyl group, a 2,4-bis(N,N-dimethylamino)phenyl group, a 2,6-bis(N,N-dimethylamino)phenyl group, a 2,4,6-tris(N,N-dimethylamino) phenyl group, a 2,6-bis(N,N-diethylamino) phenyl group, a 2,6-bis(N,N-di-n-propylamino)phenyl group, a 2,6-bis(N,N-diisopropylamino)phenyl group, a 1-[2-(N,N-dimethylamino)]naphthyl group, a 2-[1-(N,N-dimethylamino)]naphthyl group, or a 9-[10-(N,N-dimethylamino)]anthracenyl group; an aryl group having 6 to 14 carbon atoms substituted with a halogen atom (having a halogen atom), such as a 2-fluorophenyl group, a 3-fluorophenyl group, a 4-fluorophenyl group, a 2,4-difluorophenyl group, a 2,6-difluorophenyl group, a 2,4,6-trifluorophenyl group, a 2,6-dichlorophenyl group, a 2,6-dibromophenyl group, a 2,6-iodophenyl group, a 1-(2-fluoro)naphthyl group, a 2-(1-fluoro)naphthyl group, or a 9-(10-fluoro)anthracenyl group; an aryl group having 6 to 14 carbon atoms substituted with a nitro group (having a nitro group), such as a 2-nitrophenyl group, a 3-nitrophenyl group, a 4-nitrophenyl group, a 2,4-dinitrophenyl group, a 2,6-dinitrophenyl group, a 2,4,6-trinitrophenyl group, a 1-(2-nitro)naphthyl group, a 2-(1-nitro)naphthyl group, or a 9-(10-nitro)anthracenyl group; and the like. Among these aryl groups having 6 to 14 carbon atoms, the (unsubstituted) aryl group having 6 to 14 carbon atoms that does not have a substituent; the aryl group having 6 to 14 carbon atoms substituted with an alkyl group having 1 to 6 carbon atoms (having an alkyl group having 1 to 6 carbon atoms); the aryl group having 6 to 14 carbon atoms substituted with an alkoxy group having 1 to 6 carbon atoms (having an alkoxy group having 1 to 6 carbon atoms); the aryl group having 6 to 14 carbon atoms substituted with a halogen atom (having a halogen atom); and the aryl group having 6 to 14 carbon atoms substituted with a nitro group (having a nitro group) are preferable. Among these, the (unsubstituted) aryl group having 6 to 14 carbon atoms that does not have a substituent; the aryl group having 6 to 14 carbon atoms substituted with an alkyl group having 1 to 6 carbon atoms (having an alkyl group having 1 to 6 carbon atoms); and the aryl group having 6 to 14 carbon atoms substituted with an alkoxy group having 1 to 6 carbon atoms (having an alkoxy group having 1 to 6 carbon atoms) are more preferable, and the (unsubstituted) aryl group having 6 to 14 carbon atoms that does not have a substituent; and the aryl group having 6 to 14 carbon atoms substituted with an alkyl group having 1 to 6 carbon atoms (having an alkyl group having 1 to 6 carbon atoms) are even more preferable. It should be noted that in the specific examples described above, the alkyl group, the alkoxy group, the alkylthio group, and the dialkylamino group in "an alkyl group having 1 to 6 carbon atoms, an alkoxy group having 1 to 6 carbon atoms, an alkylthio group having 1 to 6 carbon atoms, and a dialkylamino group having 2 to 12 carbon atoms" substituting the aryl group having 6 to 14 carbon atoms are not limited to a normal-isomer. The specific examples also include branched or cyclic substituents such as a sec-isomer, a tert-isomer, an iso-isomer, and a neo-isomer. In addition, the number of carbon atoms constituting the substituents means the number of carbon atoms contained in each of the substituents and does not mean the total number of carbon atoms counted in a case where there is a plurality of substituents.

In a case where "$R^{51}$ and $R^{52}$ are bonded to each other through an alkylene group having 2 to 4 carbon atoms" in the general formula [8], the alkylene group having 2 to 4 carbon atoms may be linear or branched. Examples thereof include a dimethylene group (ethylene group), a trimethylene group, a propylene group, a tetramethylene group, a 1-methyltrimethylene group, a 2-methyltrimethylene group, a 1,2-dimethyldimethylene group (1,2-dimethylethylene group), a 1,1-dimethydimethylene group (1,1-dimethylethylene group), an ethyldimethylene group (ethylethylene group), and the like. Among these alkylene groups, the dimethylene group (ethylene group) is preferable.

In a case where "$R^{51}$ and $R^{52}$ are bonded to each other through an alkylene group having 2 to 4 carbon atoms" in the general formula [8], the alkylene group and a —N—C=N— group bonded to the alkylene group form a 5- to 7-membered cyclic structure together.

Specific examples of the cyclic structure include an imidazoline ring, a 1,4,5,6-tetrahydropyrimidine ring, a 4-methylimidazoline ring, a 5-methylimidazoline ring, a 1,3-diaza-2-cycloheptene ring, a 1,4,5,6-tetrahydro-4-methylpyrimidine ring, a 1,4,5,6-tetrahydro-5-methylpyrimidine ring, a 1,4,5,6-tetrahydro-6-methylpyrimidine ring, a 4-ethylimidazoline ring, a 5-ethylimidazoline ring, a 4,4-dimethylimidazoline ring, a 4,5-dimethylimidazoline ring, and a 5,5-dimethylimidazoline ring. Among these cyclic structures, the imidazoline ring is preferable.

As $Q^1$ to $Q^4$ in the general formula [9], the group represented by the general formula [10] is preferable.

The alkyl group having 1 to 6 carbon atoms represented by $R^{54}$ to $R^{57}$ in the general formula [10] may be a linear, branched, or cyclic. Examples thereof include a methyl group, an ethyl group, a n-propyl group, an isopropyl group, a cyclopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, and the like. Among these alkyl groups, a linear, branched, or cyclic alkyl group having 1 to 3 carbon atoms is preferable, and a methyl group is more preferable.

As $R^{54}$ to $R^{57}$ in the general formula [10], an alkyl group having 1 to 6 carbon atoms is preferable.

Specific examples of the alkyl group having 1 to 6 carbon atoms represented by $R^{58}$ to $R^{63}$ in the general formula [11] are the same as the specific examples of the alkyl group having 1 to 6 carbon atoms represented by $R^{54}$ to $R^{57}$ in the general formula [10], and preferred specific examples are also the same.

As $R^{58}$ to $R^{63}$ in the general formula [11], an alkyl group having 1 to 6 carbon atoms is preferable.

Specific examples of the amidinium cation represented by the general formula [6] include cations represented by the following formulae [6-1] and [6-2].

Formulae [6-1] and [6-2]

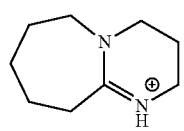

[6-1]

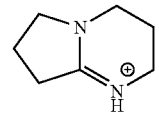

[6-2]

Specific examples of the guanidium cation represented by the general formula [7] include cations represented by the following formulae [7-1] to [7-3].

Formulae [7-1] to [7-3]

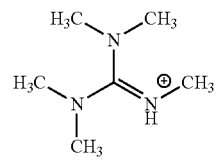

[7-1]

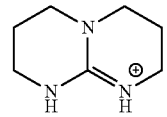

[7-2]

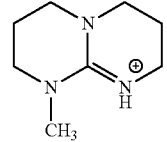

[7-3]

Specific examples of the biguanidinium cation represented by the general formula [8] include cations represented by the following formulae [8-1] to [8-9].

Formulae [8-1] to [8-9]

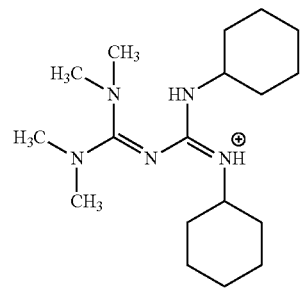

[8-1]

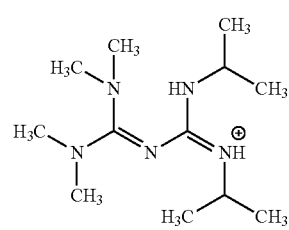

[8-2]

-continued
[8-3] 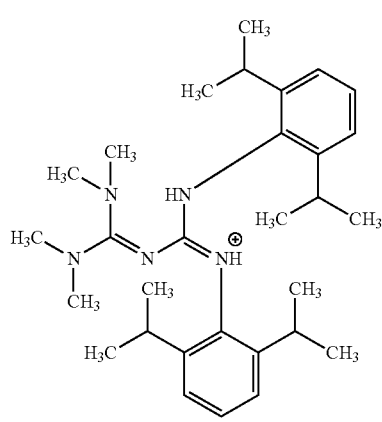
[8-8] 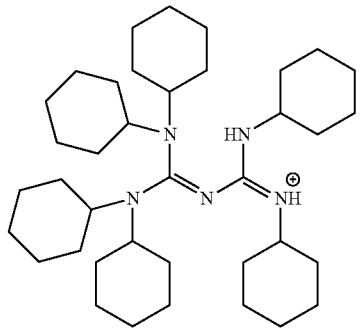
[8-4] 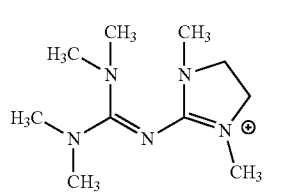
[8-9] 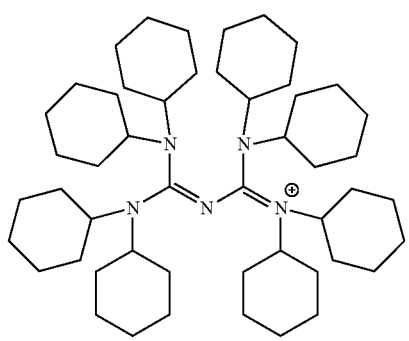
[8-5] 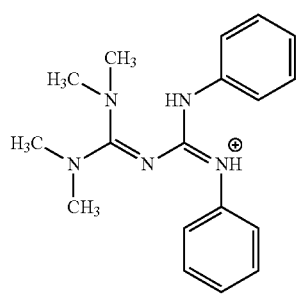
Specific examples of the phosphazenium cation represented by the general formula [9] include cations represented by the following formulae [9-1] to [9-6].
Formulae [9-1] to [9-6]
[9-1] 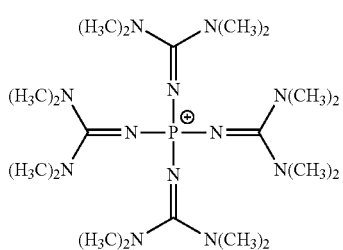
[8-6] 
[8-7] 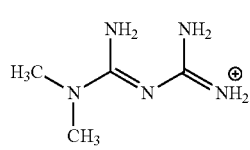
[9-2] 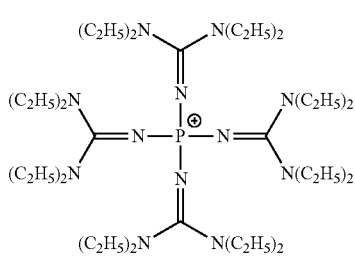

[9-3]

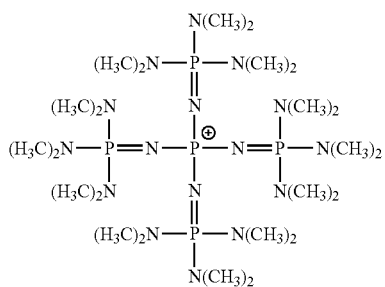

[9-4]

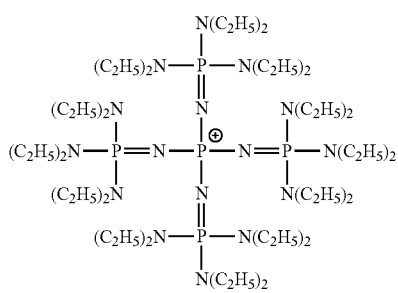

[9-5]

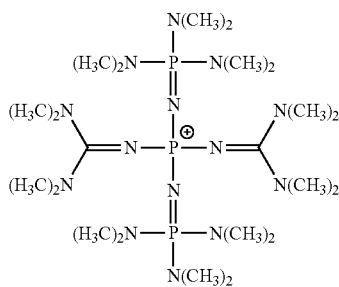

[9-6]

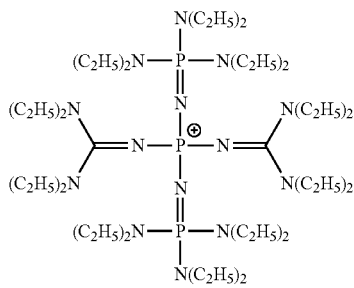

Among the cations represented by $Z_1^+$, the biguanidinium cation which can generate a strong base is preferable. The compound (E) or the compound (A/E) having the biguanidinium cation can generate biguanide which is a strong base. Therefore, in a case where the compound (E) or the compound (A/E) in which $Z_1^+$ represents a biguanidinium cation is used in the photocuring method of the present invention, a uniform crosslinked product (resin) is easily obtained.

Among the biguanidinium cations represented by the general formula [8], a biguanidinium cation represented by the following general formula [8'] is preferable.

General formula [8']

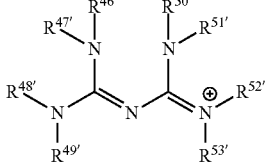

wherein $R^{46'}$ to $R^{50'}$ and $R^{53'}$ each independently represent a hydrogen atom or an alkyl group having 1 to 6 carbon atoms, and $R^{51'}$ and $R^{52'}$ each independently represent an alkyl group having 2 to 8 carbon atoms; or a phenyl group which may have a substituent selected from the group consisting of an alkyl group having 1 to 3 carbon atoms, an alkoxy group having 1 to 3 carbon atoms, a halogen atom, and a nitro group.

Specific examples of the alkyl group having 1 to 6 carbon atoms represented by $R^{46'}$ to $R^{50'}$ and $R^{53'}$ in the general formula [8'] are the same as the specific examples of the alkyl group having 1 to 6 carbon atoms represented by $R^{46}$ to $R^{50}$ and $R^{53}$ in the general formula [8], and preferred specific examples are also the same.

As $R^{46'}$ to $R^{49'}$ in the general formula [8'], an alkyl group having 1 to 6 carbon atoms is preferable.

As $R^{50'}$ and $R^{53'}$ in the general formula [8'], a hydrogen atom is preferable. It is more preferable that both of $R^{50'}$ and $R^{53'}$ are hydrogen atoms.

Specific examples of the alkyl group having 2 to 8 carbon atoms represented by $R^{51'}$ and $R^{52'}$ in the general formula [8'] are the same as the specific examples of the alkyl group having 2 to 8 carbon atoms represented by $R^{51}$ and $R^{52}$ in the general formula [8], and preferred specific examples are also the same.

In "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'], the "phenyl group which may have a substituent" means that the phenyl group includes both of a phenyl group which does not have a substituent and a phenyl group which has a substituent.

Specific examples of the alkyl group having 1 to 3 carbon atoms in "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'] are the same as the specific examples of the alkyl group having 1 to 3 carbon atoms that is a preferred example of the alkyl group having 1 to 6 carbon atoms in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8].

Specific examples of the alkoxy group having 1 to 3 carbon atoms in "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'] are the same as the specific examples of the alkoxy group having 1 to 3 carbon atoms that is a preferred example of the alkoxy group having 1 to 6 carbon atoms in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8].

Specific examples of the halogen atom in "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'] are the same as the specific examples of the halogen atom in "an aryl group having 6 to 14 carbon atoms that may have a substituent selected from the group consisting of an alkyl group having 1 to 6 carbon atoms, an alkoxy group having 1 to 6 carbon atoms, an alkylthio group having 1 to 6 carbon atoms, a dialkylamino group having 2 to 12 carbon atoms, a halogen atom, and a nitro group" represented by $R^{51}$ and $R^{52}$ in the general formula [8]. Furthermore, specific preferred examples of the halogen atom in the phenyl group are the same as the specific preferred examples of the halogen atom in the aryl group.

As "a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'], an alkyl group having 1 to 3 carbon atoms and an alkoxy group having 1 to 3 carbon atoms are preferable. Among these, the alkyl group having 1 to 3 carbon atoms is more preferable.

In "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'], the number of substituents on the phenyl group is, for example, an integer of 0 (unsubstituted) to 5. Among these, an integer of 0 (unsubstituted) to 2 is preferable.

In "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'], the substitution position of the substituent on the phenyl group is the same as the substitution position of the substituent on the phenyl group in a case where the aryl group having 6 to 14 carbon atoms in "an aryl group having 6 to 14 carbon atoms that may have a substituent selected from the group consisting of an alkyl group having 1 to 6 carbon atoms, an alkoxy group having 1 to 6 carbon atoms an alkylthio group having 1 to 6 carbon atoms, a dialkylamino group having 2 to 12 carbon atoms, a halogen atom, and a nitro group" represented by $R^{51}$ and $R^{52}$ in the general formula [8] is a phenyl group. The preferred substitution position and the more preferred substitution position are also the same.

Specific examples of "a phenyl group which may have a substituent selected from the group consisting of an alkyl group having 1 to 3 carbon atoms, an alkoxy group having 1 to 3 carbon atoms, a halogen atom, and a nitro group" represented by $R^{51'}$ and $R^{52'}$ in the general formula [8'] include a (unsubstituted) phenyl group which does not have a substituent such as a phenyl group; a phenyl group substituted with an alkyl group having 1 to 3 carbon atoms (having an alkyl group having 1 to 3 carbon atoms) such as a 2-methylphenyl group, a 3-methylphenyl group, a 4-methylphenyl group, a 2,4-dimethylphenyl group, a 2,6-dimethylphenyl group, a 2,4,6-trimethylphenyl group, a 2,6-diethylphenyl group, a 2,6-di-n-propylphenyl group, or a 2,6-diisopropylphenyl group; a phenyl group substituted with an alkoxy group having 1 to 3 carbon atoms (having an alkoxy group having 1 to 3 carbon atoms), such as a 2-methoxyphenyl group, a 3-methoxyphenyl group, a 4-methoxyphenyl group, a 2,4-dimethoxyphenyl group, a 2,6-dimethoxyphenyl group, a 2,4,6-trimethoxyphenyl group, a 2,6-diethoxyphenyl group, a 2,6-di-n-propoxyphenyl group, or a 2,6-diisopropoxyphenyl group; a phenyl group substituted with a halogen atom (having a halogen atom) such as a 2-fluorophenyl group, a 3-fluorophenyl group, a 4-fluorophenyl group, a 2,4-difluorophenyl group, a 2,6-difluorophenyl group, a 2,4,6-trifluorophenyl group, a 2,6-dichlorophenyl group, a 2,6-dibromophenyl group, or a 2,6-iodophenyl group; a phenyl group substituted with a nitro group (having a nitro group) such as a 2-nitrophenyl group, a 3-nitrophenyl group, a 4-nitrophenyl group, a 2,4-dinitrophenyl group, a 2,6-dinitrophenyl group, or a 2,4,6-trinitrophenyl group; and the like. Among these phenyl groups, the (unsubstituted) phenyl group which does not have a substituent; the phenyl group substituted with an alkyl group having 1 to 3 carbon atoms (having an alkyl group having 1 to 3 carbon atoms); and the phenyl group substituted with an alkoxy group having 1 to 3 carbon atoms (having an alkoxy group having 1 to 3 carbon atoms) are preferable. Among these, the (unsubstituted) phenyl group which does not have a substituent; and the phenyl group substituted with an alkyl group having 1 to 3 carbon atoms (having an alkyl group having 1 to 3 carbon atoms) are more preferable. It should be noted that the number of carbon atoms constituting the substituents means the number of carbon atoms contained in each of the substituents and does not mean the total number of carbon atoms counted in a case where there is a plurality of substituents. For example, in the case of the 2,6-diisopropylphenyl group and the 2,6-diisopropoxyphenyl group, these are phenyl groups substituted with an alkyl or alkoxy group having 3 carbon atoms (having an alkyl or alkoxy group having 3 carbon atoms) and have two isopropyl groups or two isopropoxy groups. Accordingly, the total number of carbon atoms in the substituent is 6.

As $R^{51'}$ and $R^{52'}$ in the general formula [8'], an alkyl group having 1 to 6 carbon atoms is preferable.

Specific examples of the biguanidinium cation represented by the general formula [8] include cations represented by the formulae [8-1] to [8-3], the formula [8-5], the formula [8-6], the formula [8-8], and the formula [8-9].

The compound (E) and the compound (A/E) having the biguanidinium cation represented by the general formula [8'] among the biguanidinium cations can further increase the contrast between an exposed portion (portion irradiated with light) and an unexposed portion (portion not being irradiated with light) in the photocuring method of the present invention.

Specific examples of the compound (E) having the biguanidinium cation include compounds represented by the following formulae [4-1] to [4-7].

Formulae [4-1] to [4-7]

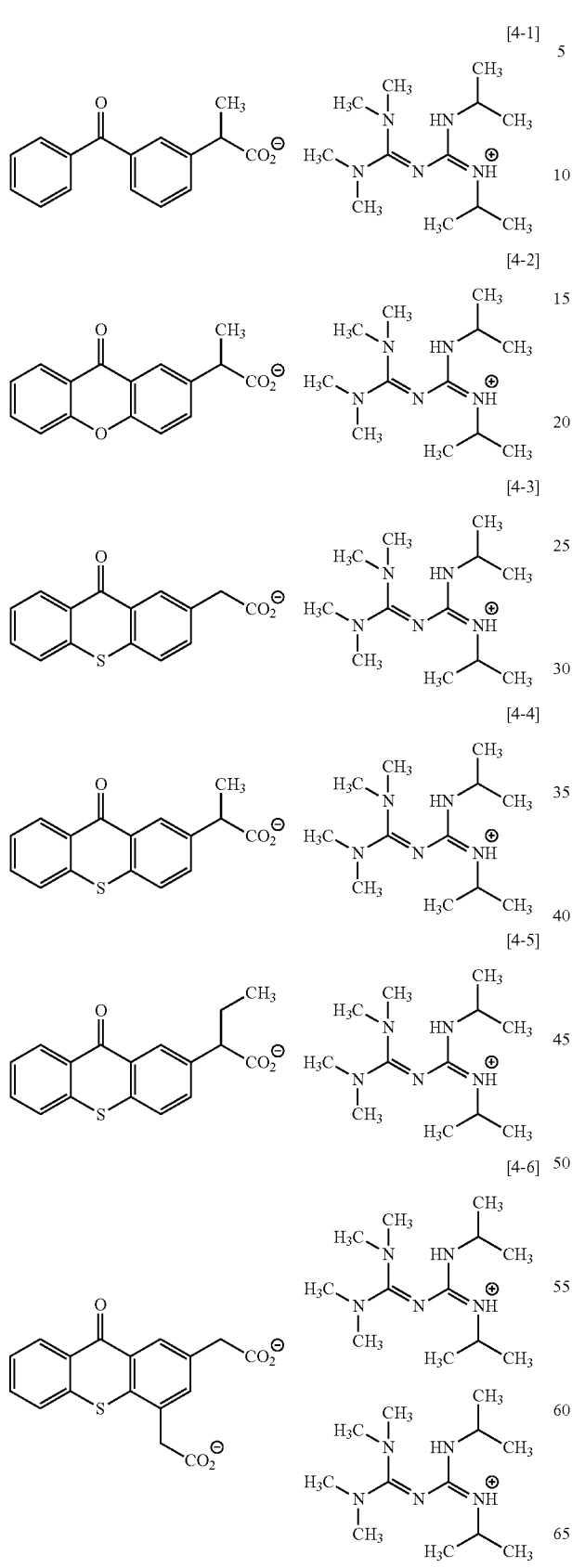

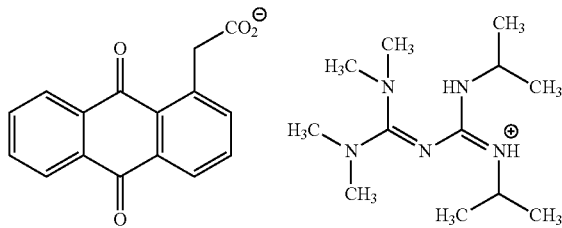

Specific examples of the compound (A/E) having the biguanidinium cation include a compound represented by the following formula [4-8].

Formula [4-8]

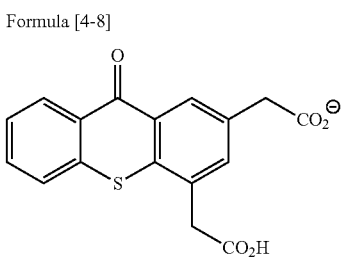

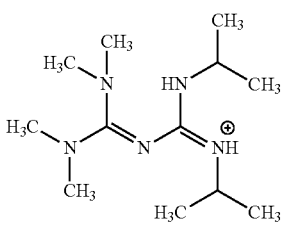

The silane coupling agent (B) according to the photocuring method of the present invention is a raw material of a crosslinked product containing a constitutional unit derived from the silane compound (D) in the photocuring method of the present invention, and is (B) silane coupling agent having at least one dialkoxysilyl group or a trialkoxysilyl group which causes a sol-gel reaction and at least one mercapto group which causes an ene-thiol reaction or a yne-thiol reaction or at least one (meth)acryl group which causes radical polymerization.

Specific examples of the silane coupling agent having a trialkoxysilyl group and at least one mercapto group among the silane coupling agents (B) include a silane coupling agent represented by the following general formula [12].

General formula [12]:

$$R^{65}-Si(OR^{64})_3 \qquad [12]$$

wherein three $R^{64}$'s each independently represent an alkyl group having 1 to 4 carbon atoms, and $R^{65}$ represents an alkyl group having 1 to 8 carbon atoms that has at least one mercapto group.

The alkyl group having 1 to 4 carbon atoms represented by $R^{64}$ in the general formula [12] may be linear, branched, or cyclic. Examples thereof include a methyl group, an ethyl group, a n-propyl group, an isopropyl group, a cyclopropyl group, a n-butyl group, an isobutyl group, a sec-butyl group, a tert-butyl group, a cyclobutyl group, and the like. Among these alkyl groups, the methyl group is preferable.

The alkyl group having 1 to 8 carbon atoms in "an alkyl group having 1 to 8 carbon atoms that has at least one mercapto group" represented by $R^{65}$ in the general formula [12] may be linear, branched, or cyclic. Examples thereof include a methyl group, an ethyl group, a n-propyl group, an isopropyl group, a cyclopropyl group, a n-butyl group, an isobutyl group, a sec-butyl group, a tert-butyl group, a cyclobutyl group, n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a norbornyl group (norbornan-χ-yl group), and the like. Among these alkyl groups, a linear, branched, or cyclic alkyl group having 1 to 6 carbon atoms is preferable. Among these, a linear, branched, or cyclic alkyl group having 1 to 4 carbon atoms is more preferable.

In "an alkyl group having 1 to 8 carbon atoms that has at least one mercapto group" represented by $R^{65}$ in the general formula [12], the mercapto group (thiol group) is bonded to the middle of a chain of the alkyl group and/or bonded to the terminal of the alkyl group, and the binding position is not limited. In addition, at least one mercapto group (thiol group) may be bonded to the alkyl group. For example, a plurality of mercapto groups (thiol groups) such as 2 to 4 mercapto groups may be bonded to the alkyl group.

Specific examples of the silane coupling agent represented by the general formula [12] include (3-mercaptopropyl)trimethoxysilane, (3-mercaptopropyl)triethoxysilane, (3-mercaptopropyl)tripropoxysilane, (3-mercaptopropyl)tributoxysilane, 1,4-dimercapto-2-(trimethoxysilyl)butane, 1,4-dimercapto-2-(triethoxysilyl)butane, 1,4-dimercapto-2-(tripropoxysilyl)butane, 1,4-dimercapto-2-(tributoxysilyl)butane, 2-mercaptomethyl-3-mercaptopropyltrimethoxysilane, 2-mercaptomethyl-3-mercaptopropyltriethoxysilane, 2-mercaptomethyl-3-mercaptopropyltripropoxysilane, 2-mercaptomethyl-3-mercaptopropyltributoxysilane, 1,2-dimercaptoethyltrimethoxysilane, 1,2-dimercaptoethyltriethoxysilane, 1,2-dimercaptoethyltripropoxysilane, 1,2-dimercaptoethyltributoxysilane, and the like. Among these silane coupling agents, the (3-mercaptopropyl)trimethoxysilane is preferable because this compound exhibits high reactivity in a hydrolysis reaction and has excellent economic efficiency. It should be noted that one kind of these silane coupling agents may be used singly, or two or more kinds of these silane coupling agents may be used in combination.

Specific examples of the silane coupling agent having a dialkoxysilyl group or a trialkoxysilyl group and at least one (meth)acryl group include a silane coupling agent represented by the following general formula [13].

General formula [13]:

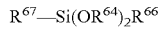

$R^{67}$—Si(O$R^{64}$)$_2R^{66}$    [13]

wherein $R^{66}$ represents an alkyl group having 1 to 4 carbon atoms or an alkoxy group having 1 to 4 carbon atoms, $R^{67}$ represents an alkyl group having 1 to 8 carbon atoms that has at least one (meth)acryl group (methacrylate), and two $R^{64}$'s are the same as $R^{64}$ described above.

Specific examples of the alkyl group having 1 to 4 carbon atoms represented by $R^{66}$ in the general formula [13] are the same as the Example of the alkyl group having 1 to 4 carbon atoms represented by $R^{64}$ in the general formula [12], and preferred specific examples are also the same.

The alkoxy group having 1 to 4 carbon atoms represented by $R^{66}$ in the general formula [13] may be linear, branched, or cyclic. Examples thereof include a methoxy group, an ethoxy group, a n-propoxy group, an isopropoxy group, a cyclopropoxy group, a n-butoxy group, an isobutoxy group, a sec-butoxy group, a tert-butoxy group, a cyclobutoxy group, and the like. Among these alkoxy groups, the methoxy group is preferable.

Specific examples of the alkyl group having 1 to 8 carbon atoms in "an alkyl group having 1 to 8 carbon atoms having at least one (meth)acryl group (methacrylate)" represented by $R^{67}$ in the general formula [13] are the same as the specific examples of the alkyl group having 1 to 8 carbon atoms represented by $R^{65}$ in the general formula [12], and preferred specific examples are also the same.

In "an alkyl group having 1 to 8 carbon atoms that has at least one (meth)acryl group (methacrylate)" represented by $R^{67}$ in the general formula [13], the (meth)acryl group (methacrylate) is bonded to the middle of a chain of the alkyl group and/or bonded to the terminal of the alkyl group, and the binding position is not limited. In addition, at least one (meth)acryl group (methacrylate) may be bonded to the alkyl group. For example, a plurality of (meth)acryl groups (methacrylates) such as 2 to 4 (meth)acryl groups may be bonded to the alkyl group.

Specific examples of the silane coupling agent having a (meth)acryl group represented by the general formula [13] include 3-(acryloxy)propylmethyldimethoxysilane, 3-(acryloxy)propyltrimethoxysilane, 3-(acryloxy)propylmethyldiethoxysilane, 3-(acryloxy)propyltriethoxysilane, 3-(methacryloxy)propylmethyldimethoxysilane, 3-(methacryloxy)propyltrimethoxysilane, 3-(methacryloxy)propylmethyldiethoxysilane, 3-(methacryloxy)propyltriethoxysilane, and the like. Among these silane coupling agents, the 3-(acryloxy)propyltrimethoxysilane and 3-(methacryloxy)propyltrimethoxysilane are preferable because these compounds exhibit high reactivity in a hydrolysis reaction and have excellent economic efficiency. It should be noted that one kind of these silane coupling agents may be used singly, or two or more kind of these silane coupling agents may be used in combination.

(C) water according to the photocuring method of the present invention causes hydrolysis of the alkoxysilyl group in the silane coupling agent (B) in the step 1. (C) water is not particularly limited as long as it is water generally used in the field of the related art. Specifically, examples thereof include purified water such as distilled water and deionized water.

(D) silane compound having a mercapto group or a (meth)acryl group and at least one silanol group according to the photocuring method of the present invention is a silane compound obtained through the hydrolysis reaction between the silane coupling agent (B) and (C) water in the step 1.

Specific examples of a silane compound having a mercapto group and at least one silanol group among the silane compounds (D), that is, specific examples of a silane compound obtained through the reaction between a silane coupling agent having a mercapto group and water include a silane compound represented by the following general formula [14].

General formula [14]:

$$R^{65}\text{—Si}(OR^{68})_3 \quad [14]$$

wherein three $R^{68}$'s each independently represent a hydrogen atom or an alkyl group having 1 to 4 carbon atoms, and $R^{65}$ is the same as $R^{65}$ described above, provided that at least one of three $R^{68}$'s is a hydrogen atom.

Specific examples of the alkyl group having 1 to 4 carbon atoms represented by $R^{68}$ in the general formula [14] are the same as the specific examples of the alkyl group having 1 to 4 carbon atoms represented by $R^{64}$ in the general formula [12], and preferred specific examples are also the same.

At least one of three $R^{68}$'s in the general formula [14] is a hydrogen atom. Particularly, it is preferable that one or two out of three $R^{68}$'s represent a hydrogen atom.

Specific examples of the silane compound having a mercapto group and at least one silanol group represented by the general formula [14] include (3-mercaptopropyl)monohydroxydimethoxysilane, (3-mercaptopropyl)dihydroxymonomethoxysilane, (3-mercaptopropyl)trihydroxysilane, (3-mercaptopropyl)monohydroxydiethoxysilane, (3-mercaptopropyl)dihydroxymonoethoxysilane, (3-mercaptopropyl)monohydroxydipropoxysilane, (3-mercaptopropyl)dihydroxymonopropoxysilane, (3-mercaptopropyl)monohydroxydibutoxysilane, (3-mercaptopropyl)dihydroxymonobutoxysilane, 1,4-dimercapto-2-(monohydroxydimethoxysilyl)butane, 1,4-dimercapto-2-(dihydroxymonomethoxysilyl)butane, 1,4-dimercapto-2-(trihydroxysilyl)butane, 1,4-dimercapto-2-(monohydroxydiethoxysilyl)butane, 1,4-dimercapto-2-(dihydroxymonoethoxysilyl)butane, 1,4-dimercapto-2-(monohydroxydipropoxysilyl)butane, 1,4-dimercapto-2-(dihydroxymonopropoxysilyl)butane, 1,4-dimercapto-2-(monohydroxydibutoxysilyl)butane, 1,4-dimercapto-2-(dihydroxymonobutoxysilyl)butane, 2-mercaptomethyl-3-mercaptopropylmonohydroxydimethoxysilane, 2-mercaptomethyl-3-mercaptopropyldihydroxymonomethoxysilane, 2-mercaptomethyl-3-mercaptopropyltrihydroxysilane, 2-mercaptomethyl-3-mercaptopropylmonohydroxydiethoxysilane, 2-mercaptomethyl-3-mercaptopropyldihydroxymonoethoxysilane, 2-mercaptomethyl-3-mercaptopropylmonohydroxysipropoxysilane, 2-mercaptomethyl-3-mercaptopropyldihydroxymonopropoxysilane, 2-mercaptomethyl-3-mercaptopropylmonohydroxydibutoxysilane, 2-mercaptomethyl-3-mercaptopropyldihydroxymonobutoxysilane, 1,2-dimercaptoethylmonohydroxydimethoxysilane, 1,2-dimercaptoethyldihydroxymonomethoxysilane, 1,2-dimercaptoethyltrihydroxysilane, 1,2-dimercaptoethylmonohydroxydiethoxysilane, 1,2-dimercaptoethyldihydroxymonoethoxysilane, 1,2-dimercaptoethylmonohydroxydipropoxysilane, 1,2-dimercaptoethyldihydroxymonopropoxysilane, 1,2-dimercaptoethylmonohydroxydibutoxysilane, 1,2-dimercaptoethyldihydroxymonobutoxysilane, and the like. Among these silane compounds, the (3-mercaptopropyl)monohydroxydimethoxysilane and the (3-mercaptopropyl)dihydroxymonomethoxysilane are preferable because these compounds can inhibit the polycondensation (the sol-gel process) occurring between the silane compounds (D) in the step 1 and make it easy for the polycondensation (the sol-gel process) to proceed in the step 2. It should be noted that, in the step 1, one kind of these silane compounds are obtained in some cases or two or more kinds of these silane compounds are obtained in some cases. In addition, in the step 2, one kind of these silane compounds may be used singly, or two or more kinds of these silane compounds may be used in combination.

Specific examples of the silane compound having a (meth)acryl group and at least one silanol group, that is, specific examples of the silane compound obtained through the reaction between the silane coupling agent having a (meth)acryl group and water include a silane compound represented by the following general formula [15].

General formula [15]:

$$R^{67}\text{—Si}(OR^{68})_2R^{69} \quad [15]$$

wherein $R^{69}$ represents a hydroxy group, an alkyl group having 1 to 4 carbon atoms, or an alkoxy group having 1 to 4 carbon atoms, and $R^{67}$ and $R^{68}$ are the same as $R^{67}$ and $R^{68}$ described above, provided that in a case where $R^{69}$ among two $R^{68}$'s and $R^{69}$ is an alkyl group having 1 to 4 carbon atoms or an alkoxy group having 1 to 4 carbon atoms, at least one of two $R^{68}$'s is a hydrogen atom, and in a case where both of two $R^{68}$'s represent an alkyl group having 1 to 4 carbon atoms, $R^{69}$ is a hydroxy group.

Specific examples of the alkyl group having 1 to 4 carbon atoms represented by $R^{69}$ in the general formula [15] are the same as the specific examples of the alkyl group having 1 to 4 carbon atoms represented by $R^{64}$ in the general formula [12], and preferred specific examples are also the same.

Specific examples of the alkoxy group having 1 to 4 carbon atoms represented by $R^{69}$ in the general formula [15] are the same as the specific examples of the alkoxy group having 1 to 4 carbon atoms represented by $R^{66}$ in the general formula [13], and preferred specific examples are also the same.

In a case where $R^{69}$ among two $R^{68}$'S and $R^{69}$ in the general formula [15] is an alkyl group having 1 to 4 carbon atoms or an alkoxy group having 1 to 4 carbon atoms, at least one of two $R^{68}$'s is a hydrogen atom, and in a case where both of two $R^{68}$'s represent an alkyl group having 1 to 4 carbon atoms, $R^{69}$ is a hydroxy group. That is, the silane compound represented by the general formula [15] has at least one hydroxy group. Particularly, it is preferable that (1) one of two $R^{68}$'s is an alkyl group having 1 to 4 carbon atoms in a case where $R^{69}$ is a hydroxy group and (2) $R^{69}$ is an alkyl group having 1 to 4 carbon atoms or an alkoxy group having 1 to 4 carbon atoms in a case where both of two $R^{68}$'s represent a hydrogen atom. That is, it is preferable the combination of $R^{68}$'s and $R^{69}$ is other than the combination in which both of two $R^{68}$'s are hydrogen atoms and $R^{69}$ is a hydroxy group. It is preferable that in the silane compound represented by the general formula [15], at least one hydroxy group is present but not all of three $R^{68}$'s and $R^{69}$ represent a hydroxy group.

Specific examples of the silane compound having a (meth)acryl group and at least one silanol group represented by the general formula [15] include 3-(acryloxy)propylmethylmonohydroxymonomethoxysilane, 3-(acryloxy)propylmethyldihydroxysilane, 3-(acryloxy)propylmonohydroxydimethoxysilane, 3-(acryloxy)propyldihydroxymonomethoxysilane, 3-(acryloxy)propyltrihydroxysilane, 3-(acryloxy)propylmethylmonohydroxymonoethoxysilane, 3-(acryloxy)propylmonohydroxydiethoxysilane, 3-(acryloxy)propyldihydroxymonoethoxysilane, 3-(methacryloxy)propylmethylmonohydroxymonomethoxysilane, 3-(methacryloxy)propylmethyldihydroxysilane, 3-(methacryloxy)propylmonohydroxydimethoxysilane, 3-(methacryloxy)propyldihydroxymonomethoxysilane, 3-(methacryloxy)propyltrihydroxysilane, 3-(methacryloxy)propylmethylmonohydroxymonoethoxysilane, 3-(methacryloxy)propylmonohydroxydiethoxysilane, 3-(methacryloxy)propyldihydroxymonoethoxysilane, and the like. Among these silane compounds, the 3-(acryloxy)propylmonohydroxydimethoxysilane, the 3-(acryloxy)propyldihydroxymonomethoxysilane, the 3-(methacryloxy)propylmonohydroxydimethoxysilane, and the 3-(methacryloxy)propyldihydroxymonomethoxysilane are preferable because these compounds can inhibit the polycondensation (the sol-gel process) between the silane compounds (D) in the step 1 and make it easy for the polycondensation (the sol-gel process) to easily proceed in the step 2. It should be noted that, in the step 1, one kind of these silane compounds are obtained in some cases or two or more kinds of these silane compounds are obtained in some cases. In addition, in the step 2, one kind of these silane compounds may be used singly, or two or more kinds of these silane compounds may be used in combination.

(F) compound having two or more polymerizable unsaturated groups according to the photocuring method of the present invention is a raw material reacting with (D) silane compound having a mercapto group or a (meth)acryl group and at least one silanol group obtained in the step 1 to obtain a crosslinked product containing a constitutional unit derived from the silane compound (D) and a constitutional unit derived from the compound (F) having the polymerizable unsaturated groups. The compound (F) is a compound having two or more polymerizable unsaturated groups causing a radical polymerization reaction or an ene-thiol reaction or a yne-thiol reaction.

Examples of the compound (F) include compounds that are generally used in the field of the related art. Examples thereof include the compounds described in JP2007-291313 A, JP2014-28938 A, and the like; a polyfunctional allyl compound such as a compound having 2 allyl group including diallylhexahydrophthalate, diallylchlorendate, diallyldiphenylsilane, or the like, a compound having 3 allyl groups including a 2,4,6-tris(allyloxy)-1,3,5-triazine, triallyltrimellitate, or the like, or a compound having 4 or more allyl groups including tetraallylpyromellitate or the like; a polyfunctional (meth)acryl compound such as a compound having 2 (meth)acryl groups including 1,3-butylene glycol di(meth)acrylate, 1,4-butanedion di(meth)acrylate, 1,6-hexanediol di(meth)acrylate, 1,9-nonanediol di(meth)acrylate, a 1,10-decanediol di(meth)acrylate, ethylene glycol di(meth)acrylate, diethylene glycol di(meth)acrylate, triethylene glycol di(meth)acrylate, tetraethylene glycol di(meth)acrylate, dipropylene glycol di(meth)acrylate, tripropylene glycol di(meth)acrylate, tetrapropylene glycol di(meth)acrylate or the like or a compound having 3 or 4 (meth)acryl groups including trimethylolpropane trimethacrylate, ditrimethylolpropane tetraacrylate, pentaerythritol tetraacrylate, or the like; a polyfunctional olefin compound other than an allyl compound and a (meth)acryl compound, such as 1,3-butadiene, 1,3-pentadiene, 1,4-pentadiene, isoprene, 1,4-hexadiene, 1,5-hexadiene, 2,4-hexadiene, 2-methyl-1,4-pentadiene, 2,3-dimethyl-1,3-butadiene, 1,4-pentadiene, 1,5-heptadiene, 1,6-heptadiene, 2-methyl-1,5-hexadiene, 1,7-octadiene, 2,5-dimethyl-1,5-hexadiene, 1,5-cyclooctadiene, 1,8-nonadiene, 1,9-decadiene, 1,10-undecadiene, 1,11-dodecadiene, 1,12-tridecadiene, 1,13-tetradecadiene, tetraalloxyethane, 1,3-divinylbenzene, 1,4-divinylbenzene, 1,3,5-trivinylbenzene, 1,3-diisopropenylbenzene, 1,4-diisopropenylbenzene, 1,3,5-triisopropenylbenzene, 3,3'-divinylbiphenyl, 3,4'-divinylbiphenyl, 4,4'-divinylbiphenyl, 4,4'-diisopropenylbiphenyl, 2,6-diisopropenylnaphthalene, 1,2-bis(vinylphenyl)ethane, or 2,4,6,8-tetramethyl-2,4,6,8-tetravinylcyclotetrasiloxane; and a polyfunctional alkynyl compound such as a compound having 2 alkynyl groups including 1,6-heptadiyne, 1,7-octadiyne, 1,8-nonadiyne, 1,9-decadiyne, dipropargylamine, diethylene glycol bis(2-propynyl)ether, ethylene glycol-1,2-bis(2-propynyl)ether, 1,3-diethynylbenzene, 1,4-diethynylbenzene, 1,3-bis(2-propynyloxy)benzene, 3,5-bis(propargyloxy)benzyl alcohol, bisphenol A dipropargyl ether, bisphenol E dipropargyl ether, 4,4'-diethynylbiphenyl, 2,6-diethynylnaphthalene, 9,10-diethynylanthracene, 3,6-diethynylcarbazole, or the like, a compound having 3 alkynyl groups including tripropargylamine, 1,3,5-trialkynylbenzene, 2,4,6-tris(propynyl-2-oxy)-1,3,5-triazine, or the like, or a compound having 4 or more alkynyl groups including tetrakis(4-ethynylphenyl)methane or the like. Among these compounds (F), the compound having 4 or more alkyl groups such as tetraallylpyromellitate is preferable because this compound makes it possible to obtain a crosslinked product having high crosslinking density. It should be noted that one kind of these compounds (F) may be used singly, or two or more kinds of these compounds (F) may be used in combination.

The organic solvent according to the photocuring method of the present invention is not particularly limited as long as it is an organic solvent generally used in the field of the related art. Examples of the organic solvent include a saturated or unsaturated aliphatic hydrocarbon-based solvent such as pentane, hexane, heptane, octane, nonane, decane, tetrahydronaphthalene, menthane, or squalane, an aromatic hydrocarbon-based solvent such as benzene, toluene, ethyl benzene, diethyl benzene, trimethyl benzene, styrene, or xylene, a halogen-based solvent such as dichloromethane, trichloromethane (chloroform), or tetrachloromethane (carbon tetrachloride), an ether-based solvent such as diethyl ether, di-n-propyl ether, diisopropyl ether, methyl-tert-butyl ether, di-n-butyl ether, di-tert-butyl ether, cyclopentyl methyl ether, tetrahydrofuran, 2-methyl tetrahydrofuran, or 1,4-dioxane, an alcohol-based solvent such as methanol, ethanol, n-propanol, isopropanol, n-butanol, isobutanol, sec-butanol, tert-butanol, or 2-methoxyethanol, a glycol ether-based solvent such as ethylene glycol monomethyl ether, propylene glycol monomethyl ether (PGME), propylene glycol monoethyl ether, diethylene glycol monomethyl ether, dipropylene glycol monomethyl ether, dipropylene glycol monoethyl ether, ethylene glycol dimethyl ether, propylene glycol dimethyl ether, ethylene glycol diethyl ether, propylene glycol diethyl ether, diethylene glycol dimethyl ether, diethylene glycol diethyl ether, dipropylene glycol dimethyl ether, or dipropylene glycol diethyl ether, a glycol ether acetate-based solvent such as ethylene glycol monoethyl ether acetate, diethylene glycol monoethyl ether acetate, diethylene glycol monobutyl ether acetate, propylene glycol monomethyl ether acetate (PGMEA), propylene glycol monoethyl ether acetate, dipropylene glycol monomethyl ether acetate, or dipropylene glycol monoethyl ether acetate, a ketone-based solvent such as 2-propanone (acetone), 2-butanone (ethyl methyl ketone), diethyl ketone, 4-methyl-2-pentanone (methyl isobutyl ketone), cyclopentanone, cyclohexanone, or cycloheptanone, an ester-based solvent such as methyl acetate, ethyl acetate, n-propyl acetate, isopropyl acetate, isobutyl acetate, sec-butyl acetate, tert-butyl acetate, ethyl butyrate, isoamyl butyrate, ethyl lactate (EL), n-propyl lactate, isopropyl lactate, isobutyl lactate, sec-butyl lactate, tert-butyl lactate, isoamyl lactate, γ-butyrolactone, or butyl stearate, an amide-based solvent such as N,N-dimethylformamide, N,N-dimethylacetamide, 1-methyl-2-pyrrolidinone (N-methylpyrrolidone), or 1,3-dimethyl-2-imidazolidinone (dimethylethylene urea), a nitrile-based solvent such as acetonitrile, and the like. It should be noted that one kind of these organic solvents may be used singly, or two or more kinds of these organic solvents may be used in combination.

In the step 1 and/or the step 2, in a case where an organic solvent is contained in the reaction system, the content of the organic solvent (amount of the organic solvent used) is not particularly limited and may be appropriately set according to the purpose such as improving the compatibility of (A) to (F) or improving the coating properties of the product, which is obtained after the step 1, applied to a substrate. For example, the content of the organic solvent (amount of the organic solvent used) is generally 1 to 10 g with respect to 1 g of the compound (E) having a carbonyl group generating a radical and a group generating a base by being decarboxylated.

Examples of the additives according to the photocuring method of the present invention include a polymerization inhibitor, a UV absorber, a sensitizer, a pigment, a dye, a curing accelerator.chain transfer catalyst, an deoxidation agent.reductone, an antioxidant, a leveling agent, a surface modifier, a foaming agent, an antifoaming agent, a pH adjuster, a dispersant, a dispersion aid, an antifoggant, a surfactant, a colorant, an antifading agent, a fluorescent whitening agent, an antihalation agent, a filler, a bulking agent, a plasticizer, a plasticization accelerator, a flame retardant, an ultraviolet absorber, a fungicide, an antistatic agent, an anti-sagging agent, a magnetic substance, and the like. These additives can be used without particular limitation as long as they are generally used in the field of the related art. Among these additives, specific examples preferred as the polymerization inhibitor include p-methoxyphenol, hydroquinone, alkyl-substituted hydroquinone, catechol, tert-butyl catechol, phenothiazine, cupferron, ammonium N-nitrosophenylhydroxyalkylamine, and the like. Specific examples preferred as the sensitizer include benzophenone, p,p'-tetramethyldiaminobenzophenone, p,p'-tetraethyldiaminobenzophenone, 2-chlorothioxanthone, 2-isopropylthioxanthone, 2,4-diethylthioxanthone, anthrone, benzanthrone, anthracene, 9-ethoxyanthracene, 9,10-diphenylanthracene, acenaphthene, anthraquinone, benzoquinone, and the like. Specific examples preferred as the dispersant include a polymeric dispersant such as polyvinyl pyrrolidone, a polycarboxylic acid, sodium polycarboxylate, sodium polysulfonate, polyether such as polyethylene glycol, polyalkylene polyamine, or polyalkylene sulfonic acid. Specific examples preferred as the filler include silicon nitride, aluminum, aluminum oxide (alumina), aluminum hydroxide, aluminum nitride, beryllium oxide, boron nitride, red phosphorus, magnesium oxide, magnesium hydroxide, calcium oxide, calcium carbonate, titanium oxide, titanium nitride, potassium titanate, iron oxide, zinc oxide, zinc carbonate, zinc borate, molybdenum sulfide, lead, lead zirconate titanate, antimony oxide, barium sulfate, barium titanate, silver, talc, clay, mica, zeolite, xonotlite, hydrotalcite, wollastonite, a ferrite magnet, a samarium-cobalt (Sm—Co) magnet, a neodymium (Nd—Fe—B) magnet, gypsum, activated white earth, aramid, Teflon (registered trademark), polyoxybenzoyl whiskers, carbon, graphite, carbon black, charcoal, catechin, copper phthalocyanine, and the like. These fillers may be in the form of power, glass, fiber, flake, foil, balloon, or spherical moss. Specific examples preferred as silane monomers include methyltrimethoxysilane, ethyltrimethoxysilane, propyltrimethoxysilane, butyltrimethoxysilane, methyltriethoxysilane, ethyltriethoxysilane, propyltriethoxysilane, butyltriethoxysilane, methyltripropoxysilane, ethyltripropoxysilane, propyltripropoxysilane, butyltripropoxysilane, methyltributoxysilane, ethyltributoxysilane, propyltributoxysilane, butyltributoxysilane, tetramethoxysilane, tetraethoxysilane, tetrapropoxysilane, tetrabutoxysilane, vinyltrimethoxysilane, vinyltriethoxysilane, vinyltripropoxysilane, vinyltributoxysilane, allyltrimethoxysilane, allyltriethoxysilane, allyltripropoxysilane, allyltributoxysilane, and the like. It should be noted that one kind of these additives may be used singly, or two or more kinds of these additives may be used in combination.

The content of the additives is not particularly limited and may be appropriately set such that the intended crosslinked product (resin) is obtained. For example, the content of the dispersant (amount of the dispersant used) is generally 0.001 to 0.1 g and preferably 0.005 to 0.05 g with respect to 1 g of the filler. For example, the content of the filler (amount of the filler used) is generally 1 to 20 g and preferably 2 to 10 g with respect to the total amount of 1 g of the silane coupling agent (B) and the compound (F).

In a case where the filler is added, the particle diameter of the used filler is not particularly limited as long as the particle diameter is generally used in the field of the related art. Specifically, in a case where the filler is in coarse powder, the average particle diameter of the filler is generally 5 to 50 µm and preferably 10 to 20 µm. In a case where the average particle diameter of the coarse powder is less than 5 µm, sometimes the thermal conductivity is reduced. In a case where the average particle diameter is larger than 50 µm, sometimes the insulating properties deteriorate. Meanwhile, in a case where the filler is fine powder, the average particle diameter of the filler is generally 0.2 to 3 µm, and preferably 0.5 to 2.5 µm. In a case where the average particle diameter of the fine powder is less than 0.2 µm, sometimes the insulating properties deteriorate. In a case where the average particle diameter is larger than 3 µm, sometimes the insulating properties deteriorate.

As the compound (A), the compound (E), and the compound (A/E) according to the photocuring method of the present invention, commercial products or compounds appropriately synthesized by the known methods described in WO2014/208632, Macromolecules 2012, 45, 2219-2224, J. Am. Chem. Soc., 2001, 123, 7996-8002, J. Org. Chem., 2002, 67, 2, 541-555, and the like may be used. Specific examples of the manufacturing methods of these compounds include a method in which a thiosalicylic acid derivative and a m-phenylenediacetic acid derivative are reacted with each other in sulfuric acid to cause sulfidation, and then the reactants are reacted under heating conditions to cause a Friedel-crafts acylation type dehydration ring-closing reaction. By this method, it is possible to synthesize the compound (A) having two acetic acid units on a thioxanthone ring. In addition, as another method, a malonic acid ester having an active proton at α-position, a palladium catalyst, a phosphine ligand, and a base (for example, tripotassium phosphate) are added to a compound, which has one or plural halides on carbon atoms constituting an aromatic ring on a benzophenone ring, a xanthone ring, a thioxanthone ring, or an anthraquinone ring, and the reactants are reacted in toluene under heating conditions, thereby synthesizing a compound in which a malonic acid unit is selectively introduced into the position of the halide of the aromatic ring. Then, if necessary, various bases and electrophiles (for example, an alkyl halide, an aldehyde, and the like) are reacted with the obtained malonic acid ester derivative such that a carbon chain is introduced into the derivative, and then the malonic acid ester is hydrolyzed. By this method, the compound (A) can be synthesized. In addition, by reacting a base selected from amidine, guanidine, biguanide, and phosphazene that is a source of $Z_1^+$ in the general formula [3] with the obtained compound (A) to form a salt, the compound (E) and the compound (A/E) can be synthesized.

As the silane coupling agent (B), (C) water, the compound (F), and the organic solvent, the additives, and the like which are optional component according to the photocuring method of the present invention, commercial products of those appropriately synthesized by known methods may be used.

—Compound Represented by General Formula [16] of the Present Invention—

The compound represented by the following general formula [16] of the present invention is a compound having at least two groups represented by the general formula [2], among the compounds (A) according to the photocuring method of the present invention. That is, because the compound represented by the general formula [16] is a compound having at least two carboxyl groups decarboxylated by photoirradiation, this compound is a novel and useful compound (a photo-radical generator) which can function as an acid catalyst even being added in a small amount and can generate a radical by photoirradiation.

General formula [16]

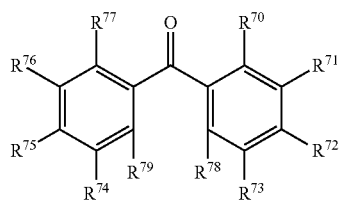

[16]

wherein $R^{70}$ to $R^{77}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], and $R^{78}$ and $R^{79}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{78}$ and $R^{79}$ are bonded to each other through an oxygen atom, a sulfur atom, or a carbonyl group, provided that at least two among the groups represented by $R^{70}$ to $R^{77}$ are groups represented by the general formula [2].

General formula [2]

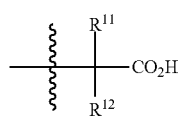

[2]

wherein $R^{11}$ and $R^{12}$ each independently represent a hydrogen atom, an alkyl group having 1 to 6 carbon atoms, or a hydroxyalkyl group having 1 to 6 carbon atoms.

General formula [3]

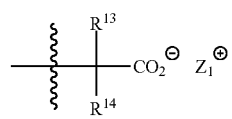

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

Specific examples of the alkyl group having 1 to 12 carbon atoms represented by $R^{70}$ to $R^{79}$ in the general formula [16] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{70}$ to $R^{79}$ in the general formula [16] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{70}$ to $R^{79}$ in the general formula [16] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{70}$ to $R^{79}$ in the general formula [16] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{70}$ to $R^{79}$ in the general formula [16] are the same as the specific examples of the halogen atom represented by $R^1$ to $R^{10}$ in the general formula [1], and preferred specific examples are also the same.

The state where $R^{78}$ and $R^{79}$ in the general formula [16] are bonded to each other through an oxygen atom, a sulfur atom, or a carbonyl group means that $R^{78}$ and $R^{79}$ form a group represented by —O—, —S—, or —C(=O)— together.

In a case where $R^{78}$ and $R^{79}$ in the general formula [16] each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{78}$ and $R^{79}$ are bonded to each other through an oxygen atom or a sulfur atom, it is desirable that the group represented by the general formula [2] and the group represented by the general formula [3] are bonded to any of $R^{71}$, $R^{73}$, $R^{74}$, and $R^{76}$. That is, in a case where $R^{78}$ and $R^{79}$ are bonded to each other through a carbonyl group, the group represented by the general formula [2] and the group represented by the general formula [3] may be bonded to any of $R^{70}$ to $R^{77}$. However, in a case where $R^{78}$ and $R^{79}$ are groups other than the above, it is desirable that the group represented by the general formula [2] and the group represented by the general formula [3] are bonded to any of $R^{71}$, $R^{73}$, $R^{74}$, and $R^{76}$.

As $R^{70}$, $R^{71}$, $R^{73}$, and $R^{77}$ in the general formula [16], a hydrogen atom and the group represented by the general formula [2] are preferable.

As $R^{72}$ and $R^{75}$ in the general formula [16], a hydrogen atom is preferable.

As $R^{74}$ in the general formula [16], a hydrogen atom, the group represented by the general formula [2], and the group represented by the general formula [3] are preferable. Among these, the hydrogen atom and the group represented by the general formula [2] are more preferable, and the hydrogen atom is even more preferable.

As $R^{76}$ in the general formula [16], a hydrogen atom, the group represented by the general formula [2], and the group represented by the general formula [3] are preferable. Among these, the hydrogen atom is more preferable.

As $R^{78}$ and $R^{79}$ in the general formula [16], a group formed by $R^{78}$ and $R^{79}$ bonded to each other through an oxygen atom or a sulfur atom is preferable.

Specific examples preferred as the compound represented by the general formula [16] include compounds represented by the following general formulae [16-A] to [16-C].

General formula [16-A]

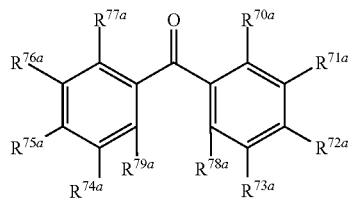

[16-A]

wherein $R^{71a}$, $R^{73a}$, $R^{74a}$, and $R^{76a}$ each independently represent a hydrogen atom, an alkyl group having 1 to 12 carbon atoms, a aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], and $R^{70a}$, $R^{72a}$, $R^{75a}$, $R^{77a}$, $R^{78a}$, and $R^{79a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least two among the groups represented by $R^{71a}$, $R^{73a}$, $R^{74a}$, and $R^{76a}$ represent the group represented by the general formula [2].

General formula [16-B]

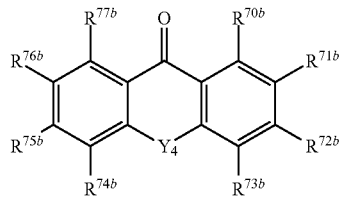

[16-B]

wherein $R^{71b}$, $R^{73b}$, $R^{74b}$, and $R^{76b}$ each independently represent a hydrogen atom, an alkyl group having 1 to 12 carbon atoms, a aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{70b}$, $R^{72b}$, $R^{75b}$, and $R^{77b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and $Y_4$ represents an oxygen atom or a sulfur atom, provided that at least two among the groups represented by $R^{71b}$, $R^{73b}$, $R^{74b}$, and $R^{76b}$ represent the group represented by the general formula [2].

General formula [16-C]

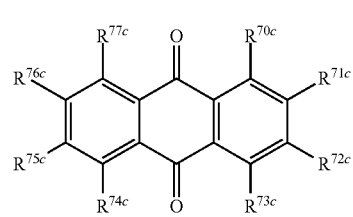

[16-C]

wherein $R^{70c}$ to $R^{77c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least two among the groups represented by $R^{70c}$ to $R^{77c}$ represent the group represented by the general formula [2].

Specific examples of the alkyl group having 1 to 12 carbon atoms represented by $R^{70a}$ to $R^{79a}$ in the general formula [16-A], $R^{70b}$ to $R^{77b}$ in the general formula [16-B], and $R^{70c}$ to $R^{77c}$ in the general formula [16-C] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{70a}$ to $R^{79a}$ in the general formula [16-A], $R^{70b}$ to $R^{77b}$ in the general formula [16-B], and $R^{70c}$ to $R^{77c}$ in the general formula [16-C] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{70a}$ to $R^{79a}$ in the general formula [16-A], $R^{70b}$ to $R^{77b}$ in the general formula [16-B], and $R^{70c}$ to $R^{77c}$ in the general formula [16-C] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{70a}$ to $R^{79a}$ in the general formula [16-A], $R^{70b}$ to $R^{77b}$ in the general formula [16-B], and $R^{70c}$ to $R^{77c}$ in the general formula [16-C] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{70a}$ to $R^{79a}$ in the general formula [16-A], $R^{70b}$ to $R^{77b}$ in the general formula [16-B], and $R^{70c}$ to $R^{77c}$ in the general formula [16-C] are the same as the specific examples of the halogen atom represented by $R^1$ to $R^{10}$ in the general formula [1], and preferred specific examples are also the same.

As $R^{70a}$, $R^{72a}$, $R^{75a}$, $R^{77a}$, $R^{78a}$, and $R^{79a}$ in the general formula [16-A], a hydrogen atom is preferable.

As $R^{71a}$ and $R^{73a}$ in the general formula [16-A], the group represented by the general formula [2] is preferable.

As $R^{74a}$ and $R^{76a}$ in the general formula [16-A], a hydrogen atom, the group represented by the general formula [2], and the group represented by the general formula [3] are preferable. Among these, the hydrogen atom is more preferable.

Examples of the preferred combination of $R^{70a}$ to $R^{79a}$ in the general formula [16-A] include combinations represented by <1> to <4> in Table 10.

TABLE 10

| Combination | $R^{70a}$ | $R^{71a}$ | $R^{72a}$ | $R^{73a}$ | $R^{74a}$ | $R^{75a}$ | $R^{76a}$ | $R^{77a}$ | $R^{78a}$ | $R^{79a}$ |
|---|---|---|---|---|---|---|---|---|---|---|
| <1> | Hydrogen atom | General formula [2] | Hydrogen atom | Hydrogen atom | Hydrogen atom | Hydrogen atom | General formula [2] | Hydrogen atom | Hydrogen atom | Hydrogen atom |
| <2> | Hydrogen atom | General formula [2] | Hydrogen atom | General formula [2] | Hydrogen atom | Hydrogen atom | Hydrogen atom | Hydrogen atom | Hydrogen atom | Hydrogen atom |
| <3> | Hydrogen atom | General formula [2] | Hydrogen atom | General formula [2] | Hydrogen atom | Hydrogen atom | General formula [2] | Hydrogen atom | Hydrogen atom | Hydrogen atom |
| <4> | Hydrogen atom | General formula [2] | Hydrogen atom | General formula [2] | General formula [2] | Hydrogen atom | General formula [2] | Hydrogen atom | Hydrogen atom | Hydrogen atom |

As $R^{70b}$, $R^{72b}$, $R^{75b}$, and $R^{77b}$ in the general formula [16-B], a hydrogen atom is preferable.

As $R^{71b}$ and $R^{73b}$ in the general formula [16-B], the group represented by the general formula [2] is preferable.

As $R^{74b}$ and $R^{76b}$ in the general formula [16-B], a hydrogen atom, the group represented by the general formula [2], and the group represented by the general formula [3] are preferable. Among these, the hydrogen atom is more preferable.

As $Y_4$ in the general formula [16-B], a sulfur atom is preferable.

Examples of the preferred combination of $Y_4$ and $R^{70b}$ to $R^{77b}$ in the general formula [16-B] include combinations represented by <1> to <8> in Table 11.

TABLE 11

| Combination | $Y_4$ | $R^{70b}$ | $R^{71b}$ | $R^{72b}$ | $R^{73b}$ | $R^{74b}$ | $R^{75b}$ | $R^{76b}$ | $R^{77b}$ |
|---|---|---|---|---|---|---|---|---|---|
| <1> | Oxygen atom | Hydrogen atom | General formula [2] | Hydrogen atom | Hydrogen atom | Hydrogen atom | Hydrogen atom | General formula [2] | Hydrogen atom |
| <2> | Oxygen atom | Hydrogen atom | General formula [2] | Hydrogen atom | General formula [2] | Hydrogen atom | Hydrogen atom | Hydrogen atom | Hydrogen atom |
| <3> | Oxygen atom | Hydrogen atom | General formula [2] | Hydrogen atom | General formula [2] | Hydrogen atom | Hydrogen atom | General formula [2] | Hydrogen atom |
| <4> | Oxygen atom | Hydrogen atom | General formula [2] | Hydrogen atom | General formula [2] | General formula [2] | Hydrogen atom | General formula [2] | Hydrogen atom |
| <5> | Sulfur atom | Hydrogen atom | General formula [2] | Hydrogen atom | Hydrogen atom | Hydrogen atom | Hydrogen atom | General formula [2] | Hydrogen atom |
| <6> | Sulfur atom | Hydrogen atom | General formula [2] | Hydrogen atom | General formula [2] | Hydrogen atom | Hydrogen atom | Hydrogen atom | Hydrogen atom |
| <7> | Sulfur atom | Hydrogen atom | General formula [2] | Hydrogen atom | General formula [2] | Hydrogen atom | Hydrogen atom | General formula [2] | Hydrogen atom |
| <8> | Sulfur atom | Hydrogen atom | General formula [2] | Hydrogen atom | General formula [2] | General formula [2] | Hydrogen atom | General formula [2] | Hydrogen atom |

As $R^{70c}$, $R^{71c}$, $R^{73c}$, $R^{74c}$, and $R^{77c}$ in the general formula [16-C], a hydrogen atom and the group represented by the general formula [2] are preferable.

As $R^{72c}$ and $R^{75c}$ in the general formula [16-C], a hydrogen atom is preferable.

As $R^{76c}$ in the general formula [16-C], a hydrogen atom, the group represented by the general formula [2], and the group represented by the general formula [3] are preferable. Among these, the hydrogen atom is more preferable.

Examples of the preferred combination of $R^{70c}$ to $R^{77c}$ in the general formula [16-C] include combinations represented by <1> to <9> in Table 12.

TABLE 12

| Combination | $R^{70c}$ | $R^{71c}$ | $R^{72c}$ | $R^{73c}$ | $R^{74c}$ | $R^{75c}$ | $R^{76c}$ | $R^{77c}$ |
|---|---|---|---|---|---|---|---|---|
| <1> | Hydrogen atom | General formula [2] | Hydrogen atom | Hydrogen atom | Hydrogen atom | Hydrogen atom | General formula [2] | Hydrogen atom |
| <2> | Hydrogen atom | General formula [2] | Hydrogen atom | General formula [2] | Hydrogen atom | Hydrogen atom | Hydrogen atom | Hydrogen atom |
| <3> | Hydrogen atom | General formula [2] | Hydrogen atom | General formula [2] | Hydrogen atom | Hydrogen atom | General formula [2] | Hydrogen atom |
| <4> | Hydrogen atom | General formula [2] | Hydrogen atom | General formula [2] | General formula [2] | Hydrogen atom | General formula [2] | Hydrogen atom |
| <5> | General formula [2] | Hydrogen atom | Hydrogen atom | General formula [2] | Hydrogen atom | Hydrogen atom | Hydrogen atom | Hydrogen atom |
| <6> | General formula [2] | Hydrogen atom | Hydrogen atom | Hydrogen atom | General formula [2] | Hydrogen atom | Hydrogen atom | Hydrogen atom |
| <7> | General formula [2] | Hydrogen atom | Hydrogen atom | Hydrogen atom | Hydrogen atom | Hydrogen atom | Hydrogen atom | General formula [2] |
| <8> | General formula [2] | Hydrogen atom | Hydrogen atom | General formula [2] | General formula [2] | Hydrogen atom | Hydrogen atom | General formula [2] |
| <9> | General formula [2] | General formula [2] | General formula [2] | General formula [2] | General formula [2] | General formula [2] | General formula [2] | General formula [2] |

Specific examples of the compound represented by the general formula [16-A] include the compounds represented by the formulae [1-A6] to [1-A9].

Specific examples of the compound represented by the general formula [16-B] include the compounds represented by the formulae [1-B8] to [1-B11].

Specific examples of the compound represented by the general formula [16-C] include the compounds represented by the formulae [1-C6] to [1-C9] and the formulae [1-C12] to [1-C14].

—Compound Represented by General Formula [17] of the Present Invention—

A compound represented by the following general formula [17] of the present invention contains (1) compound having at least one group represented by the general formula [2] and at least one group represented by the general formula [3] and (2) compound having at least two groups represented by the general formula [3]. Among these, (1) compound having at least one group represented by the general formula [2] and at least one group represented by the general formula [3] is a compound having at least one carboxyl group decarboxylated by photoirradiation and at least one group generating a base by being decarboxylated by photoirradiation. Therefore, the compound (1) is a compound which functions as both the compounds including the compound (A) and the compound (E) according to the photocuring method of the present invention. That is, the compound (1) is a novel and useful compound which can become the compound (A/E). In contrast, (2) compound having at least two groups represented by the general formula [3] is a compound having at least two groups generating a base by decarboxylated by photoirradiation. Therefore, the compound (2) is a novel and useful compound (a photobase and photo-radical generator) which can function as a photobase generator even being added in a small amount and can generate a radical by photoirradiation.

General formula [17]

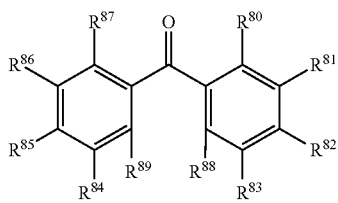

[17]

wherein $R^{80}$ to $R^{87}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by the following general formula [2], or a group represented by the following general formula [3], and $R^{88}$ and $R^{89}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{88}$ and $R^{89}$ are bonded to each other through an oxygen atom, a sulfur atom, or a carbonyl group, provided that at least one of the groups represented by $R^{80}$ to $R^{87}$ is the group represented by the following general formula [3], and at least one of the remaining 7 groups is the group represented by the following general formula [2] or the group represented by the following general formula [3].

General formula [2]

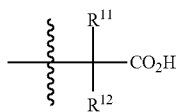

[2]

wherein $R^{11}$ and $R^{12}$ each independently represent a hydrogen atom, an alkyl group having 1 to 6 carbon atoms, or a hydroxyalkyl group having 1 to 6 carbon atoms.

General formula [3]

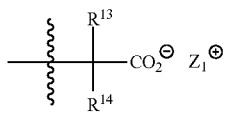

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

Specific examples of the alkyl group having 1 to 12 carbon atoms represented by $R^{80}$ to $R^{89}$ in the general formula [17] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{80}$ to $R^{89}$ in the general formula [17] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{80}$ to $R^{89}$ in the general formula [17] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{80}$ to $R^{89}$ in the general formula [17] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{80}$ to $R^{89}$ in the general formula [17] are the same as the specific examples of the halogen atom represented by $R^1$ to $R^{10}$ in the general formula [1], and preferred specific examples are also the same.

The state where $R^{88}$ and $R^{89}$ in the general formula [17] are bonded to each other through an oxygen atom, a sulfur atom, or a carbonyl group means that $R^{88}$ and $R^{89}$ form a group represented by —O—, —S—, or —C(=O)— together.

In a case where $R^{88}$ and $R^{89}$ in the general formula [17] each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{88}$ and $R^{89}$ are bonded to each other through an oxygen atom or a sulfur atom, it is desirable that the group represented by the general formula [2] and the group represented by the general formula [3] are bonded to any of $R^{81}$, $R^{83}$, $R^{84}$, and $R^{86}$. That is, in a case where $R^{88}$ and $R^{89}$ are bonded to each other through a carbonyl group, the group represented by the general formula [2] and the group represented by the general formula [3] may be bonded to any of $R^{80}$ to $R^{87}$. However, in a case where $R^{88}$ and $R^{89}$ are groups other than the above, it is desirable that the group represented by the general formula [2] and the group represented by the general formula [3] are bonded to any of $R^{81}$, $R^{83}$, $R^{84}$, and $R^{86}$.

As $R^{80}$ and $R^{81}$ in the general formula [17], a hydrogen atom, the group represented by the general formula [2], and the group represented by the general formula [3] are preferable. Among these, the hydrogen atom and the group represented by the general formula [3] are more preferable.

As $R^{82}$ and $R^{85}$ in the general formula [17], a hydrogen atom is preferable.

As $R^{83}$ in the general formula [17], the group represented by the general formula [2] and the group represented by the general formula [3] are preferable.

As $R^{84}$, $R^{86}$, and $R^{87}$ in the general formula [17], a hydrogen atom, the group represented by the general formula [2], and the group represented by the general formula [3] are preferable. Among these, the hydrogen atom is more preferable.

As $R^{88}$ and $R^{89}$ in the general formula [17], a group formed by $R^{88}$ and $R^{89}$ bonded to each other through an oxygen atom or a sulfur atom is preferable.

Specific examples preferred as the compound represented by the general formula [17] include compounds represented by the following general formulae [17-A] to [17-C].

General formula [17-A]

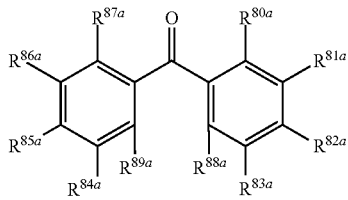

[17-A]

wherein $R^{81a}$, $R^{83a}$, $R^{84a}$, and $R^{86a}$ each independently represent a hydrogen atom, an alkyl group having 1 to 12 carbon atoms, a aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], and $R^{80a}$, $R^{82a}$, $R^{85a}$, $R^{87a}$, $R^{88a}$, and $R^{89a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of the groups represented by $R^{81a}$, $R^{83a}$, $R^{84a}$, and $R^{86a}$ is the group represented by the general formula [3], and at least one of the remaining 3 groups is the group represented by the general formula [2] or the group represented by the general formula [3].

General formula [17-B]

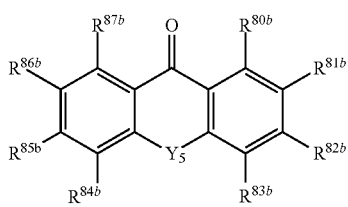

[17-B]

wherein $R^{81b}$, $R^{83b}$, $R^{84b}$, and $R^{86b}$ each independently represent a hydrogen atom, an alkyl group having 1 to 12 carbon atoms, a aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{80b}$, $R^{82b}$, $R^{85b}$, and $R^{87b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, and $Y_5$ represents an oxygen atom or a sulfur atom, provided that at least one of the groups represented by $R^{81b}$, $R^{83b}$, $R^{84b}$, and $R^{86b}$ is the group represented by the general formula [3], and at least one of the remaining 3 groups is the group represented by the general formula [2] or the group represented by the general formula [3].

General formula [17-C]

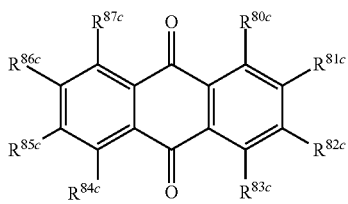

[17-C]

wherein $R^{80c}$ to $R^{87c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{80c}$ to $R^{87c}$ is the group represented by the general formula [3], and at least one of the remaining 7 groups is the group represented by the general formula [2] or the group represented by the general formula [3].

Specific examples of the alkyl group having 1 to 12 carbon atoms represented by $R^{80a}$ to $R^{89a}$ in the general formula [17-A], $R^{80b}$ to $R^{87b}$ in the general formula [17-B], and $R^{80c}$ to $R^{87c}$ in the general formula [17-C] are the same as the specific examples of the alkyl group having 1 to 12 carbon atoms represented by $R^1$ to $R^{10}$ in the general formula [1], and preferred specific examples are also the same.

Specific examples of the aryl group having 6 to 14 carbon atoms represented by $R^{80a}$ to $R^{89a}$ in the general formula [17-A], $R^{80b}$ to $R^{87b}$ in the general formula [17-B], and $R^{80c}$ to $R^{87c}$ in the general formula [17-C] are the same as the specific examples of the aryl group having 6 to 14 carbon atoms represented by $R^1$ to $R^{10}$ in the general formula [1], and preferred specific examples are also the same.

Specific examples of the arylalkyl group having 7 to 15 carbon atoms represented by $R^{80a}$ to $R^{89a}$ in the general formula [17-A], $R^{80b}$ to $R^{87b}$ in the general formula [17-B], and $R^{80c}$ to $R^{87c}$ in the general formula [17-C] are the same as the specific examples of the arylalkyl group having 7 to 15 carbon atoms represented by $R^1$ to $R^{10}$ in the general formula [1], and preferred specific examples are also the same.

Specific examples of the alkoxy group having 1 to 12 carbon atoms represented by $R^{80a}$ to $R^{89a}$ in the general formula [17-A], $R^{80b}$ to $R^{87b}$ in the general formula [17-B], and $R^{80c}$ to $R^{87c}$ in the general formula [17-C] are the same as the specific examples of the alkoxy group having 1 to 12 carbon atoms represented by $R^1$ to $R^{10}$ in the general formula [1], and preferred specific examples are also the same.

Specific examples of the halogen atom represented by $R^{80a}$ to $R^{89a}$ in the general formula [17-A], $R^{80b}$ to $R^{87b}$ in the general formula [17-B], and $R^{80c}$ to $R^{87c}$ in the general formula [17-C] are the same as the specific examples of the halogen atom represented by $R^1$ to $R^{10}$ in the general formula [1], and preferred specific examples are also the same.

As $R^{80a}$, $R^{82a}$, $R^{85a}$, $R^{87a}$, $R^{88a}$, and $R^{89a}$ in the general formula [17-A], a hydrogen atom is preferable.

As $R^{81a}$ in the general formula [17-A], the group represented by the general formula [2] and the group represented by the general formula [3] are preferable. Among these, the group represented by the general formula [3] is more preferable.

As $R^{83a}$ in the general formula [17-A], the group represented by the general formula [2] and the group represented by the general formula [3] are preferable.

As $R^{84a}$ and $R^{86a}$ in the general formula [17-A], a hydrogen atom, the group represented by the general formula [2], and the group represented by the general formula [3] are preferable. Among these, the hydrogen atom is more preferable.

Examples of the preferred combination of $R^{80a}$ to $R^{89a}$ in the general formula [17-A] include combinations represented by <1> to <6> in Table 13.

TABLE 13

| Combination | $R^{80a}$ | $R^{81a}$ | $R^{82a}$ | $R^{83a}$ | $R^{84a}$ | $R^{85a}$ | $R^{86a}$ | $R^{87a}$ | $R^{88a}$ | $R^{89a}$ |
|---|---|---|---|---|---|---|---|---|---|---|
| <1> | Hydrogen atom | General formula [2] | Hydrogen atom | General formula [3] | Hydrogen atom | Hydrogen atom | Hydrogen atom | Hydrogen atom | Hydrogen atom | Hydrogen atom |
| <2> | Hydrogen atom | General formula [3] | Hydrogen atom | Hydrogen atom | Hydrogen atom | Hydrogen atom | General formula [3] | Hydrogen atom | Hydrogen atom | Hydrogen atom |
| <3> | Hydrogen atom | General formula [3] | Hydrogen atom | General formula [3] | Hydrogen atom | Hydrogen atom | Hydrogen atom | Hydrogen atom | Hydrogen atom | Hydrogen atom |
| <4> | Hydrogen atom | General formula [3] | Hydrogen atom | General formula [3] | Hydrogen atom | Hydrogen atom | General formula [3] | Hydrogen atom | Hydrogen atom | Hydrogen atom |
| <5> | Hydrogen atom | General formula [3] | Hydrogen atom | General formula [3] | General formula [3] | Hydrogen atom | General formula [3] | Hydrogen atom | Hydrogen atom | Hydrogen atom |
| <6> | Hydrogen atom | General formula [3] | Hydrogen atom | General formula [2] | Hydrogen atom | Hydrogen atom | Hydrogen atom | Hydrogen atom | Hydrogen atom | Hydrogen atom |

As $R^{80b}$, $R^{82b}$, $R^{85b}$, and $R^{87b}$ in the general formula [17-B], a hydrogen atom is preferable.

As $R^{81b}$ in the general formula [17-B], the group represented by the general formula [2] and the group represented by the general formula [3] are preferable. Among these, the group represented by the general formula [3] is more preferable.

As $R^{83b}$ in the general formula [17-B], the group represented by the general formula [2] and the group represented by the general formula [3] are preferable.

As $R^{84b}$ and $R^{86b}$ in the general formula [17-B], a hydrogen atom, the group represented by the general formula [2], and the group represented by the general formula [3] are preferable. Among these, the hydrogen atom is more preferable.

As $Y_5$ in the general formula [17-B], a sulfur atom is preferable.

Examples of the preferred combination of $Y_5$ and $R^{80b}$ to $R^{87b}$ in the general formula [17-B] include combinations represented by <1> to <12> in Table 14.

TABLE 14

| Combination | $Y_5$ | $R^{80b}$ | $R^{81b}$ | $R^{82b}$ | $R^{83b}$ | $R^{84b}$ | $R^{85b}$ | $R^{86b}$ | $R^{87b}$ |
|---|---|---|---|---|---|---|---|---|---|
| <1> | Oxygen atom | Hydrogen atom | General formula [2] | Hydrogen atom | General formula [3] | Hydrogen atom | Hydrogen atom | Hydrogen atom | Hydrogen atom |
| <2> | Oxygen atom | Hydrogen atom | General formula [3] | Hydrogen atom | Hydrogen atom | Hydrogen atom | Hydrogen atom | General formula [3] | Hydrogen atom |
| <3> | Oxygen atom | Hydrogen atom | General formula [3] | Hydrogen atom | General formula [3] | Hydrogen atom | Hydrogen atom | Hydrogen atom | Hydrogen atom |
| <4> | Oxygen atom | Hydrogen atom | General formula [3] | Hydrogen atom | General formula [3] | Hydrogen atom | Hydrogen atom | General formula [3] | Hydrogen atom |
| <5> | Oxygen atom | Hydrogen atom | General formula [3] | Hydrogen atom | General formula [3] | General formula [3] | Hydrogen atom | General formula [3] | Hydrogen atom |
| <6> | Oxygen atom | Hydrogen atom | General formula [3] | Hydrogen atom | General formula [2] | Hydrogen atom | Hydrogen atom | Hydrogen atom | Hydrogen atom |
| <7> | Sulfur atom | Hydrogen atom | General formula [2] | Hydrogen atom | General formula [3] | Hydrogen atom | Hydrogen atom | Hydrogen atom | Hydrogen atom |
| <8> | Sulfur atom | Hydrogen atom | General formula [3] | Hydrogen atom | Hydrogen atom | Hydrogen atom | Hydrogen atom | General formula [3] | Hydrogen atom |

TABLE 14-continued

| Combination | $Y_5$ | $R^{80b}$ | $R^{81b}$ | $R^{82b}$ | $R^{83b}$ | $R^{84b}$ | $R^{85b}$ | $R^{86b}$ | $R^{87b}$ |
|---|---|---|---|---|---|---|---|---|---|
| <9> | Sulfur atom | Hydrogen atom | General formula [3] | Hydrogen atom | General formula [3] | Hydrogen atom | Hydrogen atom | Hydrogen atom | Hydrogen atom |
| <10> | Sulfur atom | Hydrogen atom | General formula [3] | Hydrogen atom | General formula [3] | Hydrogen atom | Hydrogen atom | General formula [3] | Hydrogen atom |
| <11> | Sulfur atom | Hydrogen atom | General formula [3] | Hydrogen atom | General formula [3] | General formula [3] | Hydrogen atom | General formula [3] | Hydrogen atom |
| <12> | Sulfur atom | Hydrogen atom | General formula [3] | Hydrogen atom | General formula [2] | Hydrogen atom | Hydrogen atom | Hydrogen atom | Hydrogen atom |

As $R^{80c}$ and $R^{81c}$ in the general formula [17-C], a hydrogen atom, the group represented by the general formula [2], and the group represented by the general formula [3] are preferable. Among these, the hydrogen atom and the group represented by the general formula [3] are more preferable.

As $R^{82c}$ and $R^{85c}$ in the general formula [17-C], a hydrogen atom is preferable.

As $R^{83c}$ in the general formula [17-C], the group represented by the general formula [2] and the group represented by the general formula [3] are preferable.

As $R^{84c}$, $R^{86c}$, and $R^{87c}$ in the general formula [17-C], a hydrogen atom, the group represented by the general formula [2], and the group represented by the general formula [3] are preferable. Among these the hydrogen atom is more preferable.

Examples of the preferred combination of $R^{80c}$ to $R^{87c}$ in the general formula [17-C] include combinations represented by <1> to <13> in Table 15.

Specific examples of the compound represented by the general formula [17-A] include the compounds represented by the formula [1-A10] and the formulae [4-A6] to [4-A10].

Specific examples of the compound represented by the general formula [17-B] include the compounds represented by the formula [1-B12] and the formulae [4-B8] to [4-B12].

Specific examples of the compound represented by the general formula [17-C] include the compounds represented by the formula [1-C10], the formulae [4-C6] to [4-C10], and the formulae [4-C12] to [4-C14].

Among the above compounds, the compounds represented by the formula [1-A10], the formula [1-B12], the formula [1-C10], the formula [4-A10], the formula [4-B12], and the formula [4-C10] correspond to (1) compound represented by the general formula [17] having at least one group represented by the general formula [2] and at least one group represented by the general formula [3]. The compounds represented by the formulae [4-A6] to [4-A9], formulae [4-B8] to [4-B11], the formulae [4-C6] to [4-C9], and the formulae [4-C12] to [4-C14] correspond to (2) compound represented by the general formula [17] having at least two groups represented by the general formula [3].

—Photocuring Resin Composition of the Present Invention—

The photocuring resin composition of the present invention is a resin composition which contains (A) compound having a carbonyl group generating a radical by photoirradiation and a carboxyl group decarboxylated by photoirra-

TABLE 15

| Combination | $R^{80c}$ | $R^{81c}$ | $R^{82c}$ | $R^{83c}$ | $R^{84c}$ | $R^{85c}$ | $R^{86c}$ | $R^{87c}$ |
|---|---|---|---|---|---|---|---|---|
| <1> | Hydrogen atom | General formula [2] | Hydrogen atom | General formula [3] | Hydrogen atom | Hydrogen atom | Hydrogen atom | Hydrogen atom |
| <2> | Hydrogen atom | General formula [3] | Hydrogen atom | Hydrogen atom | Hydrogen atom | Hydrogen atom | General formula [3] | Hydrogen atom |
| <3> | Hydrogen atom | General formula [3] | Hydrogen atom | General formula [3] | Hydrogen atom | Hydrogen atom | Hydrogen atom | Hydrogen atom |
| <4> | Hydrogen atom | General formula [3] | Hydrogen atom | General formula [3] | Hydrogen atom | Hydrogen atom | General formula [3] | Hydrogen atom |
| <5> | Hydrogen atom | General formula [3] | Hydrogen atom | General formula [3] | General formula [3] | Hydrogen atom | General formula [3] | Hydrogen atom |
| <6> | Hydrogen atom | General formula [3] | Hydrogen atom | General formula [2] | Hydrogen atom | Hydrogen atom | Hydrogen atom | Hydrogen atom |
| <7> | General formula [2] | Hydrogen atom | Hydrogen atom | General formula [3] | Hydrogen atom | Hydrogen atom | Hydrogen atom | Hydrogen atom |
| <8> | General formula [3] | Hydrogen atom | Hydrogen atom | General formula [3] | Hydrogen atom | Hydrogen atom | Hydrogen atom | Hydrogen atom |
| <9> | General formula [3] | Hydrogen atom | Hydrogen atom | Hydrogen atom | General formula [3] | Hydrogen atom | Hydrogen atom | Hydrogen atom |
| <10> | General formula [3] | Hydrogen atom | Hydrogen atom | Hydrogen atom | Hydrogen atom | Hydrogen atom | Hydrogen atom | General formula [3] |
| <11> | General formula [3] | Hydrogen atom | Hydrogen atom | General formula [3] | General formula [3] | Hydrogen atom | Hydrogen atom | General formula [3] |
| <12> | General formula [3] | Hydrogen atom | Hydrogen atom | General formula [2] | Hydrogen atom | Hydrogen atom | Hydrogen atom | Hydrogen atom |
| <13> | General formula [3] | General formula [3] | General formula [3] | General formula [3] | General formula [3] | General formula [3] | General formula [3] | General formula [3] | diation, (D) silane compound having a mercapto group or a (meth)acryl group and at least one silanol group, (E) compound having a carbonyl group generating a radical by photoirradiation and a group generating a base by being decarboxylated by photoirradiation, and may further contain (F) compound having two or more polymerizable unsaturated groups.

In a case where the silane compound (D) in the photocuring resin composition of the present invention is (D') silane compound having a mercapto group and at least one silanol group, (F) compound having two or more polymerizable unsaturated groups is an essential component. That is, the photocuring resin composition of the present invention, in which the silane compound (D) is (D') silane compound having a mercapto group and at least one silanol group, is a resin composition containing at least (A) compound having a carbonyl group generating a radical by photoirradiation and a carboxyl group decarboxylated by photoirradiation, (D') silane compound having a mercapto group and at least one silanol group, (E) compound having a carbonyl group generating a radical by photoirradiation and a group generating a base by being decarboxylated by photoirradiation, and (F) compound having two or more polymerizable unsaturated groups.

In a case where the silane compound (D) in the photocuring resin composition of the present invention is (D") compound having a (meth)acryl group and at least one silanol group, (F) compound having two or more polymerizable unsaturated groups is an optional component. That is, the photocuring resin composition of the present invention, in which the silane compound (D) is (D") compound having a (meth)acryl group and at least one silanol group, is a resin composition containing at least (A) compound having a carbonyl group generating a radical by photoirradiation and a carboxyl group decarboxylated by photoirradiation, (D") compound having a (meth)acryl group and at least one silanol group, and (E) compound having a carbonyl group generating a radical by photoirradiation and a group generating a base by being decarboxylated by photoirradiation.

The photocuring resin composition of the present invention may contain, in addition to the components described above, for example, an organic solvent, additives, a monomer component such as a crosslinking agent other than the silane compound (D) or the compound (F), and the like.

Specific examples of the components of the compound (A), the silane compound (D), the compound (E), and the compound (F), the organic solvent, the additives, the monomer component, and the like in the photocuring resin composition of the present invention are as described above.

The contents of the components of the compound (A), the silane compound (D), the compound (E), and the compound (F), the organic solvent, the additives, the monomer component, and the like in the photocuring resin composition of the present invention are as described above.

The photocuring resin composition of the present invention can be prepared by adding the compound (E) to a composition containing the compound (A), the silane coupling agent (B), and (C) water and further adding the compound (F) if necessary. That is, the photocuring resin composition of the present invention can be prepared by adding the compound (E) to the composition, which is obtained by adding, if necessary, the compound (A) to the silane compound (D) obtained by reacting the silane coupling agent (B) and (C) water with each other in the presence of the compound (A), and further adding the compound (F) thereto if necessary.

By irradiating the photocuring resin composition of the present invention with light (active energy rays), the carboxyl group in the compound (A) is decarboxylated, hence the acidic group (the carboxyl group) is lost, and the compound (E) generates a base. Accordingly, the pH of the composition shifts to an alkaline pH from an acidic pH. With this change, a radical is generated in the composition. That is, by the irradiation of light (active energy rays), the sol-gel reaction and the radical polymerization reaction, the ene-thiol reaction, or the yne-thiol reaction efficiently proceed in the photocuring resin composition of the present invention, and as a result, a crosslinked product containing a constitutional unit derived from the silane compound (D) can be obtained. Therefore, the photocuring resin composition of the present invention is a useful composition which makes it possible to obtain a crosslinked product (resin) by the irradiation of light (active energy rays).

The photocuring resin composition of the present invention can be used as a resin raw material in optical materials or electronic materials such as paint, printing ink, dental materials, resist, color filters, films for flexible display, electronic parts, semiconductor devices, interlayer insulating films, coating film for wiring, thermally conductive films, optical circuits, optical circuit portions, antireflection films, and holograms.

In a case where the photocuring resin composition of the present invention is used as a thermally conductive film, it is desirable that a cured film obtained from the photocuring resin composition of the present invention has electrical insulating properties. Specifically, the electrical insulating properties are generally indicated by an electric resistivity which is equal to or higher than 1 $\Omega \cdot cm$, preferably equal to or higher than 10 $\Omega \cdot cm$, more preferably equal to or higher than $10^5$ $\Omega \cdot cm$, even more preferably equal to or higher than $10^{10}$ $\Omega \cdot cm$, and most preferably equal to or higher than 1013 $\Omega \cdot cm$.

EXAMPLES

Hereinbelow, the present invention will be specifically described based on examples and comparative examples, but the present invention is not limited thereto. It should be noted that unless otherwise specified, % in the following examples is based on weight.

Synthesis Example 1: Synthesis of
1-(2-thioxanthenyl)diethyl malonate

Diethyl malonate (0.88 g, 5.5 mmol; manufactured by Wako Pure Chemical Industries, Ltd.), 3.18 g of tripotassium phosphate (15.0 mmol; manufactured by Wako Pure Chemical Industries, Ltd.), and 15 mL of toluene were added to 1.23 g of 2-chlorothioxanthone (5.0 mmol; manufactured by Wako Pure Chemical Industries, Ltd.), and then 36.9 mg (0.1 mmol) of $Pd_2(allyl)Cl_2$ and 123 mg of S-phos(2-dichlorohexylphosphino-2',6'-dimethoxybiphenyl) (0.3 mmol; manufactured by Wako Pure Chemical Industries, Ltd.) were added thereto, and the mixture was heated and stirred for 4 hours at 100° C. After the reaction ended, the reaction solution was cooled to room temperature, ethyl acetate and 1 N hydrochloric acid were added to the reaction solution, and the generated black powder was removed by being filtered through celite. Thereafter, water was added to the filtrate to perform liquid separation and washing, the organic layer obtained after the liquid separation and washing was then concentrated under reduced pressure, and the obtained residue was purified by silica gel column chromatography, thereby obtaining 1.30 g of 1-(2-thioxanthenyl)diethyl malonate (yellow oil-like substance, yield: 70%). The result of $^1$H-NMR measured and the structural formula of the 1-(2-thioxanthenyl)diethyl malonate are shown below.

$^1$H-NMR (400 MHz, $CDCl_3$) δ (ppm): 1.26 (6H, t), 4.25 (4H, q), 4.79 (1H, s), 7.50-7.65 (4H, m), 7.81 (1H, dd), 8.55 (1H, dd), 8.61 (1H, dd).

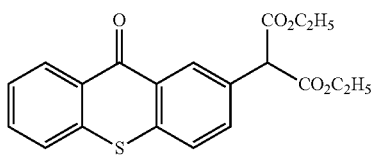 [SMILES: CCOC(=O)C(C(=O)OCC)c1ccc2sc3ccccc3c(=O)c2c1]

Synthesis Example 2: Synthesis of 2-Thioxanthenyl Acetate (Compound Represented by Formula [1-B3])

Sodium hydroxide (25%, 1.28 g, 8.0 mmol; manufactured by Wako Pure Chemical Industries, Ltd.) and 15 mL of ethanol were added to 1.0 g (2.6 mmol) of the 1-(2-thioxanthenyl)diethyl malonate obtained in the Synthesis Example 1, and the mixture was heated and stirred for 0.5 hours at 80° C. After the reaction ended, the reaction solution was cooled to room temperature, and diisopropyl ether was added to the reaction solution to subject the aqueous layer to liquid separation and washing. Thereafter, the aqueous layer was made acidic by using 1 N hydrochloric acid, liquid separation and extraction was then performed using ethyl acetate, the extract was washed with water, and then the obtained organic layer was concentrated under reduced pressure, thereby obtaining 0.65 g of 2-thioxanthenyl acetate (yellow oil-like substance, yield: 92%). The result of $^1$H-NMR measured and the structural formula of the 2-thioxanthenyl acetate (formula [1-B3]) are shown below.

$^1$H-NMR (400 MHz, CDCl$_3$) δ (ppm): 3.77 (2H, s), 7.58 (1H, t), 7.67 (1H, dd), 7.74-7.84 (3H, m), 8.35 (1H, s), 8.47 (1H, d).

[1-B3]

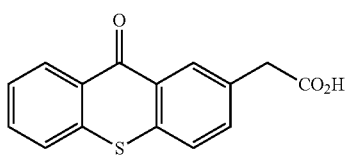

Example 1: Synthesis of (2,4-thioxanthenyl)diacetate (Compound Represented by Formula [1-B9])

Sulfuric acid (10 mL) and 2.23 g (12.0 mmol) of m-phenylene diacetate were added to 1.54 g of thiosalicylic acid (10.0 mmol; manufactured by Wako Pure Chemical Industries, Ltd.), and the mixture was heated and stirred for 2 hours at 90° C. After the reaction ended, the reaction solution was put into ice water such that the reaction solution was cooled to 5° C., the precipitated crystals were then collected by filtration and subjected to a deliquoring treatment. The obtained crystals were first made alkaline by using an aqueous sodium hydroxide solution and then neutralized using hydrochloric acid. Thereafter, the crystals were washed with acetone, and the obtained organic layer was concentrated under reduced pressure, thereby obtaining 0.82 g of (2,4-thioxanthenyl)diacetate (yellow powder, yield: 25%). The result of $^1$H-NMR measured and the structural formula of the (2,4-thioxanthenyl)diacetate (compound represented by the formula [1-B9]) are shown below.

$^1$H-NMR (400 MHz, d-DMSO) δ (ppm): 3.77 (2H, s), 3.94 (2H, s), 7.60 (1H, ddd), 7.65 (1H, dd), 7.78 (1H, ddd), 7.88 (1H, d), 8.35 (1H, dd), 8.45 (1H, dd), 12.64 (2H, brm).

[1-B9]

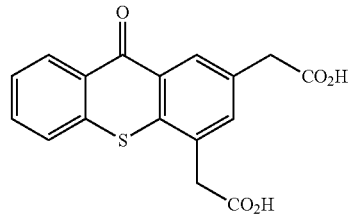

Synthesis Example 3: Synthesis of 2-(2-thioxanthenyl)propionate (Compound Represented by Formula [1-B4])

Potassium tert-butoxide (134 mg, 1.2 mmol; manufactured by Wako Pure Chemical Industries, Ltd.), 0.17 g of methyl iodide (1.2 mmol; manufactured by Wako Pure Chemical Industries, Ltd.), and 20 mL of DMF were added to 0.38 g (1.0 mmol) of the 1-(2-thioxanthenyl)diethyl malonate obtained in the Synthesis Example 1, and the mixture was heated and stirred for 1 hour at 50° C. Whether the reaction was finished was checked by thin-layer chromatography (TLC), and then water was added to the reaction solution to cause hydrolysis. Thereafter, diisopropyl ether was added to the reaction solution to perform liquid separation and washing on the aqueous layer, the aqueous layer was made acidic by using 1 N hydrochloric acid, and then liquid separation and extraction were performed using ethyl acetate. The extract was washed with water, and then the obtained organic layer was concentrated under reduced pressure, thereby obtaining 0.28 g of 2-(2-thioxanthenyl)propionate (yellow powder, yield: 100%). The result of $^1$H-NMR measured and the structural formula of the 2-(2-thioxanthenyl)propionate (compound represented by the formula [1-B4]) are shown below.

$^1$H-NMR (400 MHz, CDCl$_3$) δ (ppm): 1.60 (3H, t), 3.92 (1H, q), 7.48-7.64 (5H, m), 8.56 (1H, d), 8.63 (1H, dd), 9.50 (1H, brs).

[1-B4]

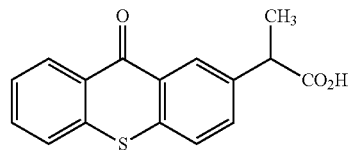

Synthesis Example 4: Synthesis of 2-(2-thioxanthenyl)butyrate (Compound Represented by Formula [1-B5])

Potassium tert-butoxide (134 mg, 1.2 mmol; manufactured by Wako Pure Chemical Industries, Ltd.), 0.18 g of ethyl iodide (1.2 mmol; manufactured by Wako Pure Chemical Industries, Ltd.), and 20 mL of DMF were added to 0.38 g (1.0 mmol) of the 1-(2-thioxanthenyl)diethyl malonate obtained in the Synthesis Example 1, and the mixture was heated and stirred for 1 hour at 50° C. Whether the reaction was finished was checked by thin-layer chromatography (TLC), and then water was added to the reaction solution to cause hydrolysis. Thereafter, diisopropyl ether was added to the reaction solution to perform liquid separation and washing on the aqueous layer, the aqueous layer was made acidic by using 1 N hydrochloric acid, and then liquid separation and extraction were performed using ethyl acetate. The extract was washed with water, and then the obtained organic layer was concentrated under reduced pressure, thereby obtaining 0.29 g of 2-(2-thioxanthenyl)butyrate (yellow oil-like substance, yield: 100%). The result of $^1$H-NMR measured and the structural formula of the 2-(2-thioxanthenyl)butyrate (compound represented by the formula [1-B5]) are shown below.

$^1$H-NMR (400 MHz, CDCl$_3$) δ (ppm): 1.60 (3H, t), 1.91 (1H, td), 2.17 (1H, td), 3.64 (1H, t), 7.26 (1H, t), 7.55-7.65 (4H, m), 8.53 (1H, d), 8.61 (1H, dd), 9.50 (1H, brs).

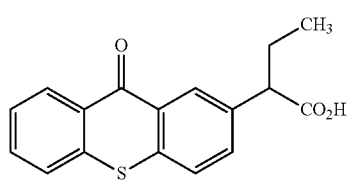

[1-B5]

Synthesis Example 5: Synthesis of 1,2-Diisopropyl-4,4,5,5-Tetramethylbiguanidium 2-Thioxanthenyl Acetate (Compound Represented by Formula [4-3])

1,2-Diisopropyl-4,4,5,5-tetramethylbiguanide (0.24 g, 1.0 mmol; manufactured by Wako Pure Chemical Industries, Ltd.) and 0.26 g (1.0 mmol) of the 2-thioxanthenyl acetate obtained in the Synthesis Example 2 were dissolved in 20 mL of methanol, and the solution was stirred for 10 minutes at room temperature. After the reaction ended, the reaction solution was concentrated under reduced pressure, and the obtained residue was washed with diisopropyl ether and then dried under reduced pressure, thereby obtaining 0.51 g of 1,2-diisopropyl-4,4,5,5-tetramethylbiguanidium 2-thioxanthenyl acetate (light yellow, amorphous, yield: 100%). The result of $^1$H-NMR measured and the structural formula of the 1,2-diisopropyl-4,4,5,5-tetramethylbiguanidium 2-thioxanthenyl acetate (compound represented by the formula [4-3]) are shown below.

$^1$H-NMR (400 MHz, CDCl$_3$) δ (ppm): 1.12 (12H, d), 2.80 (12H, s), 2.90-3.10 (3H, brm), 3.75 (2H, s), 7.56 (1H, t), 7.66 (1H, dd), 7.74-7.84 (3H, m), 8.35 (1H, s), 8.47 (1H, d), 9.50 (1H, brs).

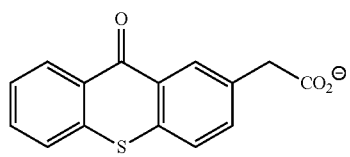

[4-3]

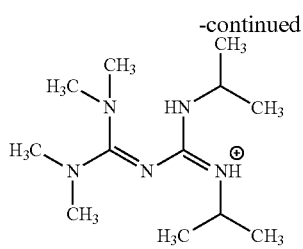

-continued

Synthesis Example 6: Synthesis of 1,2-Diisopropyl-4,4,5,5-Tetramethylbiguanidium 2-(2-Thioxanthenyl) Propionate (Compound Represented by Formula [4-4])

1,2-Diisopropyl-4,4,5,5-tetramethylbiguanide (0.24 g, 1.0 mmol; manufactured by Wako Pure Chemical Industries, Ltd.) and 0.28 g (1.0 mmol) of the 2-(2-thioxanthenyl) propionate obtained in the Synthesis Example 3 were dissolved in 20 mL of methanol, and the solution was stirred for 10 minutes at room temperature. After the reaction ended, the reaction solution was concentrated under reduced pressure, and the obtained residue was washed with diisopropyl ether and then dried under reduced pressure, thereby obtaining 0.51 g of 1,2-diisopropyl-4,4,5,5-tetramethylbiguanidium 2-(2-thioxanthenyl) propionate (light yellow, amorphous, yield: 100%). The result of $^1$H-NMR measured and the structural formula of the 1,2-diisopropyl-4,4,5,5-tetramethylbiguanidium 2-(2-thioxanthenyl) propionate (compound represented by the formula [4-4]) are shown below.

$^1$H-NMR (400 MHz, CDCl$_3$) δ (ppm): 1.13 (12H, d), 1.56 (3H, d), 2.80 (12H, s), 2.90-3.10 (1H, brm), 3.25 (2H, d), 3.84 (1H, q), 7.44-7.58 (4H, m), 7.80 (1H, dd), 8.60 (1H, s), 8.62 (1H, d), 9.56 (1H, brs).

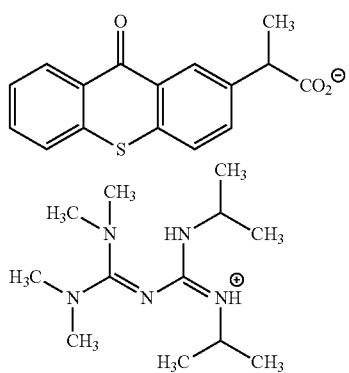

[4-4]

Synthesis Example 7: Synthesis of 1,2-Diisopropyl-4,4,5,5-Tetramethylbiguanidium 2-(2-Thioxanthenyl) Butyrate (Compound Represented by Formula [4-5])

1,2-Diisopropyl-4,4,5,5-tetramethylbiguanide (0.24 g, 1.0 mmol; manufactured by Wako Pure Chemical Industries, Ltd.) and 0.29 g (1.0 mmol) of the 2-(2-thioxanthenyl) butyrate obtained in the Synthesis Example 4 were dissolved in 20 mL of methanol, and the solution was stirred for 10 minutes at room temperature. After the reaction ended, the reaction solution was concentrated under reduced pressure, and the obtained residue was washed with diisopropyl ether and then dried under reduced pressure, thereby obtaining 0.53 g of 1,2-diisopropyl-4,4,5,5-tetramethylbiguanidium 2-(2-thioxanthenyl) butyrate (light yellow, amorphous, yield: 100%). The result of $^1$H-NMR measured and the structural formula of the 1,2-diisopropyl-4,4,5,5-tetramethylbiguanidium 2-(2-thioxanthenyl) butyrate (compound represented by the formula [4-5]) are shown below.

$^1$H-NMR (400 MHz, CDCl$_3$) δ (ppm): 0.94 (3H, t), 1.13 (12H, d), 1.82 (1H, td), 1.99 (1H, brs), 2.21 (1H, td), 2.83 (12H, s), 3.24 (2H, brm), 3.55 (1H, t), 7.41-7.74 (4H, m), 7.96 (1H, d), 8.59-8.63 (2H, m), 9.94 (1H, brs).

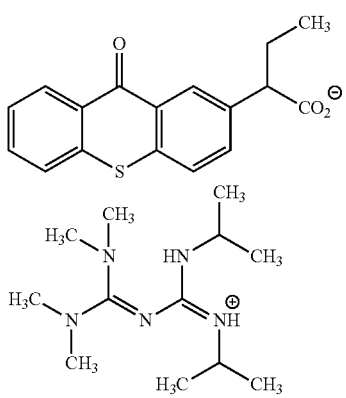

[4-5]

Example 2: Synthesis of (2,4-Thioxanthenyl)Diacetate Di(1,2-Diisopropyl-4,4,5,5-Tetramethylbiguanide) Salt (Compound Represented by Formula [4-6])

(2,4-thioxanthenyl)diacetate (0.32 g, 1.0 mmol) obtained in the Example 1 and 0.49 g of the 1,2-diisopropyl-4,4,5,5-tetramethylbiguanide (2.0 mmol; manufactured by Wako Pure Chemical Industries, Ltd.) were dissolved in 20 mL of methanol, and the mixture was stirred for 10 minutes at room temperature. After the reaction ended, the reaction solution was concentrated under reduced pressure, and the obtained residue was washed with diisopropyl ether and then dried under reduced pressure, thereby obtaining 0.57 g a (2,4-thioxanthenyl)diacetate 1,2-diisopropyl-4,4,5,5-tetramethylbiguanide salt (yellow powder, yield: 70%). The result of $^1$H-NMR measured and the structural formula of the (2,4-thioxanthenyl)diacetate di(1,2-diisopropyl-4,4,5,5-tetramethylbiguanide) salt (compound represented by the formula [4-6]) are shown below.

$^1$H-NMR (400 MHz, CDCl$_3$) δ (ppm): 1.14 (24H, d), 2.81 (24H, s), 3.26-3.30 (4H, m), 3.71 (2H, s), 2.87 (2H, brs), 3.87 (2H, s), 7.51 (1H, ddd), 7.64 (1H, dd), 7.68 (1H, dd), 7.72 (1H, ddd), 8.43 (1H, d), 8.50 (1H, dd), 9.86-9.90 (2H, brm).

[4-6]

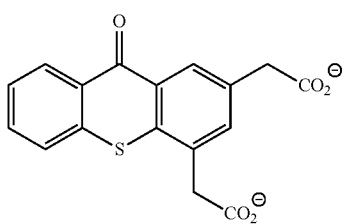

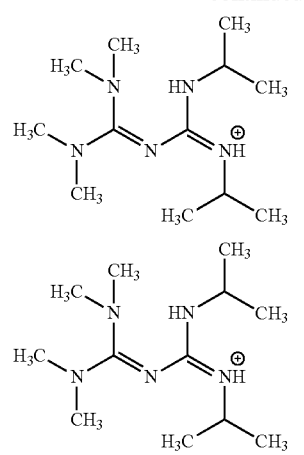

Example 3: Synthesis of (2,4-thioxanthenyl)diacetate 1,2-diisopropyl-4,4,5,5-tetramethylbiguanide Salt (Compound Represented by Formula [4-8])

(2,4-thioxanthenyl)diacetate (0.16 g, 0.5 mmol) obtained in the Example 1 and 0.11 g of the 1,2-diisopropyl-4,4,5,5-tetramethylbiguanide (0.5 mmol; manufactured by Wako Pure Chemical Industries, Ltd.) were dissolved in 20 mL of methanol, and the mixture was stirred for 10 minutes at room temperature. After the reaction ended, the reaction solution was concentrated under reduced pressure, and the obtained residue was washed with diisopropyl ether and then dried under reduced pressure, thereby obtaining 0.28 g a (2,4-thioxanthenyl)diacetate 1,2-diisopropyl-4,4,5,5-tetramethylbiguanide salt (yellow powder, yield: 100%). The result of $^1$H-NMR measured and the structural formula of the (2,4-thioxanthenyl)diacetate 1,2-diisopropyl-4,4,5,5-tetramethylbiguanide salt (compound represented by the formula [4-8]) are shown below.

$^1$H-NMR (400 MHz, CD$_3$OD) δ (ppm): 1.21 (12H, d), 2.86 (12H, s), 3.30 (2H, t), 3.70 (2H, s), 3.80 (1H, brs), 3.87 (2H, s), 7.51 (1H, ddd), 7.64 (1H, ddd), 7.68 (1H, dd), 7.72 (1H, ddd), 8.43 (1H, d), 8.50 (1H, dd).

[4-8]

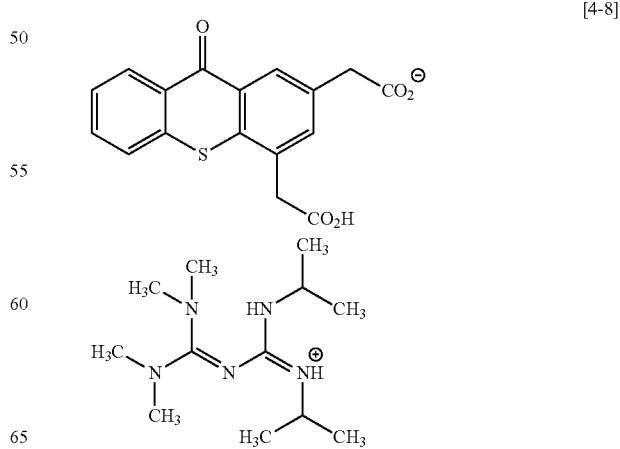

Synthesis Example 8: Synthesis of 1-Anthraquinolyl Acetate (Compound Represented by Nucleic Acid Amplification Reaction [1-C11])

Diethyl malonate (0.88 g, 5.5 mmol; manufactured by Wako Pure Chemical Industries, Ltd.), 3.18 g of tripotassium phosphate (15.0 mmol; manufactured by Wako Pure Chemical Industries, Ltd.), and 15 mL of toluene were added to 1.21 g of 1-chloroanthraquinone (5.0 mmol; manufactured by Wako Pure Chemical Industries, Ltd.), and then 36.9 mg (0.1 mmol) of $Pd_2(allyl)Cl_2$ and 123 mg of S-phos (2-dichlorohexylphosphino-2',6'-dimethoxybiphenyl) (0.3 mmol; manufactured by Wako Pure Chemical Industries, Ltd.) were added thereto, and the mixture was heated and stirred for 10 hours at 100° C. After the reaction ended, the reaction solution was cooled to room temperature, ethyl acetate and 1 N hydrochloric acid were added to the reaction solution, and the generated black powder was removed by being filtered through celite. Thereafter, water was added to the filtrate to perform liquid separation and washing, the organic layer obtained after the liquid separation and washing was then concentrated under reduced pressure, thereby obtaining a crude substance of 1-(1-anthraquinolyl)diethyl malonate. Sodium hydroxide (25%, 1.6 g, 10 mmol; manufactured by Wako Pure Chemical Industries, Ltd.) and 10 mL of ethanol were added to the obtained crude substance, and the mixture was heated and stirred for 1 hour at 80° C. After the reaction ended, the reaction solution was cooled to room temperature, and dichloromethane was added to the reaction solution to perform liquid separation and washing on the aqueous layer. Subsequently, the obtained aqueous layer was made acidic, and the precipitated solids were collected by filtration, thereby obtaining 0.64 g of 1-anthraquinolyl acetate (yellow powder, yield: 47%). The result of $^1$H-NMR measured and the structural formula of the 1-anthraquinolyl acetate (compound represented by the formula [1-C11]) are shown below.

$^1$H-NMR (400 MHz, d-DMSO) δ (ppm): 4.13 (2H, s), 7.75 (1H, d), 7.82-7.94 (3H, m), 8.13-8.22 (3H, dd).

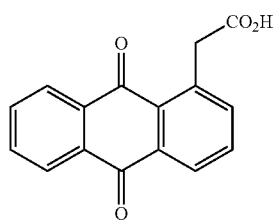

[1-C11]

Synthesis Example 9: Synthesis of 1-Anthraquinolyl Acetate 1,2-Diisopropyl-4,4,5,5-Tetramethyl Biguanide Salt (Compound Represented by Formula [4-7])

1-Anthraquiolyl acetate (0.26 g, 1.0 mmol) obtained in the Synthesis Example 8 and 0.24 g of 1,2-Diisopropyl-4,4,5,5-tetramethylbiguanide (1.0 mmol; manufactured by Wako Pure Chemical Industries, Ltd.) were dissolved in 20 mL of methanol, and the solution was stirred for 10 minutes at room temperature. After the reaction ended, the reaction solution was concentrated under reduced pressure, and the obtained residue was washed with diisopropyl ether and then dried under reduced pressure, thereby obtaining 0.50 g of a 1-anthraquinolyl acetate 1,2-diisopropyl-4,4,5,5-tetramethylbiguanide salt (yellow powder, yield: 100%). The result of $^1$H-NMR measured and the structural formula of the 1-anthraquinolyl acetate 1,2-diisopropyl-4,4,5,5-tetramethylbiguanide salt (compound represented by the formula [4-7]) are shown below.

$^1$H-NMR (400 MHz, $D_2O$) δ (ppm): 1.06 (12H, d), 2.75 (12H, s), 3.64 (2H, brs), 3.76 (2H, s), 7.36 (1H, d), 7.51 (3H, t), 7.59-7.64 (2H, m), 7.80-7.85 (3H, m).

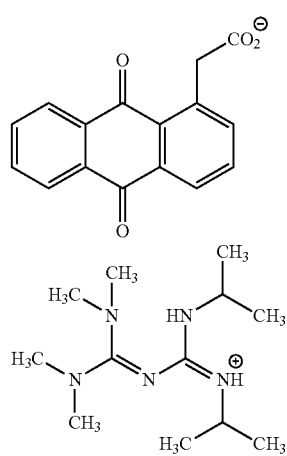

[4-7]

Examples 4 to 14 and Comparative Examples 1 and 2: Photocuring Method by Sol-Gel Reaction and Ene-Thiol Reaction Through Irradiation of Light (Active Energy Rays)

Deionized water and methanol, which is used if necessary, were added to a solution containing either (A) compound having a carbonyl group generating a radical by photoirradiation and a carboxyl group decarboxylated by photoirradiation and (E) compound having a carbonyl group generating a radical by photoirradiation and a group generating a base by being decarboxylated by photoirradiation or (A/E) compound having a carbonyl group generating a radical by photoirradiation, a carboxyl group decarboxylated by photoirradiation, and a group generating a base by being decarboxylated by photoirradiation and (3-mercaptopropyl) trimethoxysilane (manufactured by Wako Pure Chemical Industries, Ltd.). The solution was stirred for a certain period of time at room temperature until the solution became a homogeneous and clear solution. After cloudiness resulting from water disappeared and the solution became clear, (F) compound having at least two or more polymerizable unsaturated groups and various additives (polymerization inhibitor or/and UV absorber), which are used if necessary, were added thereto and mixed together again, and an alcohol generated as a side product by hydrolysis was concentrated under reduced pressure at room temperature (in addition, the number of days taken for the mixed composition to become in a state of gel that cannot be taken out of a container in a case where the composition is stored at room temperature in a sealed.light blocking state was measured). Thereafter, a coating film was prepared by coating a glass substrate with the concentrate (composition) by means of bar coating, and by using an ultraviolet irradiation light source device having a specific exposure intensity with respect to the coating film, that is, REX-250 (manufactured by Asahi Spectra Co., Ltd.), the coating film was cured by being irradiated with light (active energy rays) having a wavelength of 365 nm without using a filter such that the cumulative exposure amount became 1.0 J. The cured coating film (cured film) was immersed in acetone for 30 seconds, and whether the film was dissolved or peeled was checked. In a case where the cured film was not dissolved and peeled even being immersed in acetone, the film was evaluated as "Solvent resistance: 0", and in a case where the cured film had insufficient hardness and was dissolved in acetone or peeled, the film was evaluated as "Solvent resistance: X". In addition, pencil hardness and abrasion resistance were evaluated by performing a pencil hardness test (JIS K5600-5-4) and an abrasion resistance test (the film was rubbed back and forth 10 times with #0000 steel wool manufactured by BONSTAR SALES Co., Ltd., and then the scratches were visually checked) on the cured film. The evaluation results are shown in Tables 16 to 18. It should be noted that among the compounds (A) and the compounds (E) used in Tables 16 to 18, the structural formulae and the suppliers of the compounds for which the synthesis method thereof is not shown in synthesis examples or examples, the name of the compound (F) and various additives, and the suppliers thereof are shown below.

Compound (A): Formulae [1-A2] and [1-B2]:

[1-A2]

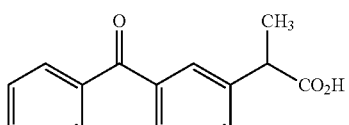

[1-B2]

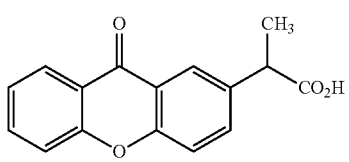

Compound (E): Formulae [4-1] and [4-2]:

[4-1]

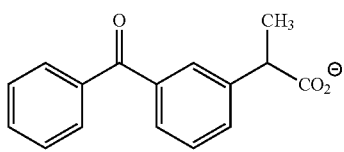

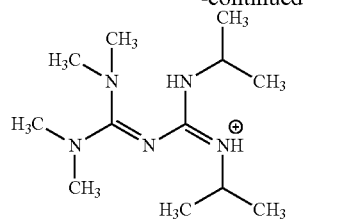

[4-2]

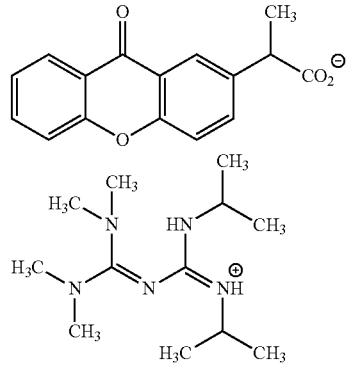

Compound (A):
[1-A2]: ketoprofen (manufactured by Hamari Chemicals, Ltd.)
[1-B2]: 2-(9-oxoxanthen-2-yl)propionate (manufactured by TOKYO CHEMICAL INDUSTRY CO., LTD.)
Compound (E):
[4-1]: 1,2-diisopropyl-4,4,5,5-tetramethyl biguanidinium 2-(3-benzoylphenyl)propionate (the compound synthesized according to WO2014/208632 was used.)
[4-2]: 1,2-diisopropyl-4,4,5,5-tetramethyl biguanidinium 2-(2-oxoxanthenyl)propionate (the compound synthesized according to WO2014/208632 was used.)
Compound (F):
TAOT: 2,4,6-tris(allyloxy)-1,3,5-triazine (manufactured by Wako Pure Chemical Industries, Ltd.)
TRIAM-805: tetraallyl pyromellitate (manufactured by Wako Pure Chemical Industries, Ltd.)
TAIC: triallyl isocyanurate (manufactured by TOKYO CHEMICAL INDUSTRY CO., LTD.)
TPOT 2,4,6-tris(propargyloxy)-1,3,5-triazine (the compound synthesized according to Angew, Chem. Int. Ed. 2004, 43, 3928-3932 was used.)
Additives:
Q-1301 (polymerization inhibitor): ammonium N-nitrosophenylhydroxylamine (manufactured by Wako Pure Chemical Industries, Ltd.)
TINUVIN-900 (UV absorber): 2-[2-hydroxy-3,5-bis($\alpha,\alpha$-dimethylbenzyl)phenyl]-2H-benzotriazole (manufactured by BASF SE)

TABLE 16

| | | Example 4 | Example 5 | Example 6 | Comparative Example 1 | Comparative Example 2 |
|---|---|---|---|---|---|---|
| Compound (A) | 1-A2 | 0.1 g (0.40 mmol) | 0.1 g (0.40 mmol) | 0.1 g (0.40 mmol) | 0.1 g (0.40 mmol) | — |
| Compound (E) | 4-1 | 0.15 g (0.30 mmol) | 0.15 g (0.30 mmol) | 0.15 g (0.30 mmol) | — | 0.15 g (0.30 mmol) |
| Silane coupling agent (B) | (3-Mercaptopropyl)trimethoxysilane | 1.96 g (10 mmol) | 1.96 g (10 mmol) | 1.96 g (10 mmol) | 1.96 g (10 mmol) | 1.96 g (10 mmol) |
| (C) Water | Deionized water | 0.52 g (30 mmol) | 0.52 g (30 mmol) | 0.52 g (30 mmol) | 0.52 g (30 mmol) | 0.52 g (30 mmol) |

TABLE 16-continued

|  |  | Example 4 | Example 5 | Example 6 | Comparative Example 1 | Comparative Example 2 |
|---|---|---|---|---|---|---|
| Organic solvent | Methanol | — | — | — | — | — |
| Compound (F) | TAOT | 0.79 g (3 mmol) |  |  | 0.79 g (3 mmol) | 0.79 g (3 mmol) |
|  | TRIAM-805 |  | 0.99 g (2.4 mmol) |  |  |  |
|  | TAIC |  |  | 0.79 g (3 mmol) |  |  |
| Hydrolysis | Stirring time taken until the solution becomes homogenous and clear solution | 1 h | 1 h | 1 h | 4 h | Gel precipitation |
| Storage stability of composition | Number of days taken until the composition becomes gel | 4 | 3 | 3 | Equal to or greater than 30 | — |
| Solvent resistance of cured film | Immersion in acetone | ○ | ○ | ○ | X | X |
| Pencil Hardness | Load 0.75 kg | 6H | 6H | 6H | — | — |
| Abrasion resistance test | Steel wool #0000 | No scratch | No scratch | No scratch | — | — |

As is evident from the results of Examples 4 to 6 in Table 16, it was understood that in a case where (A) compound having a carbonyl group generating a radical by photoirradiation and a carboxyl group decarboxylated by photoirradiation and (E) compound having a carbonyl group generating a radical by photoirradiation and a group generating a base by being decarboxylated by photoirradiation are used in combination, and the irradiation of light (active energy rays) is performed thereon, it is possible to simultaneously generate a strong base and a radical and to establish a curing system in which the sol-gel reaction and the ene-thiol reaction simultaneously proceed, and a crosslinked product (resin) containing a constitutional unit derived from the silane compound (D) is rapidly and efficiently obtained. In addition, it was understood that the obtained crosslinked product (resin) has excellent solvent resistance and high hardness. In contrast, as is evident from the results of Comparative Examples 1 and 2, it was understood that in the system in which (A) compound having a carbonyl group generating a radical by photoirradiation and a carboxyl group decarboxylated by photoirradiation and (E) compound having a carbonyl group generating a radical by photoirradiation and a group generating a base by being decarboxylated by photoirradiation are not used in combination, a crosslinked product (resin) is not obtained.

TABLE 17

|  |  | Example 7 | Example 8 | Example 9 | Example 10 | Example 11 |
|---|---|---|---|---|---|---|
| Compound (A) | 1-A2 | 0.1 g (0.40 mmol) | 0.1 g (0.40 mmol) | 0.05 g (0.20 mmol) | 0.025 g (0.10 mmol) | 0.025 g (0.10 mmol) |
| Compound (E) | 4-1 | 0.15 g (0.30 mmol) | 0.15 g (0.30 mmol) | 0.15 g (0.30 mmol) | 0.15 g (0.30 mmol) | 0.05 g (0.10 mmol) |
| Silane coupling agent (B) | (3-Mercaptopropyl)trimethoxysilane | 1.96 g (10 mmol) | 1.96 g (10 mmol) | 1.96 g (10 mmol) | 1.96 g (10 mmol) | 1.96 g (10 mmol) |
| (C) Water | Deionized water | 0.52 g (30 mmol) | 0.27 g (15 mmol) | 0.27 g (15 mmol) | 0.27 g (15 mmol) | 0.27 g (15 mmol) |
| Organic solvent | Methanol | — | — | — | — | — |
| Compound (F) | TAOT | 0.79 g (3 mmol) | 0.79 g (3 mmol) | 0.79 g (3 mmol) | 0.79 g (3 mmol) | 0.79 g (3 mmol) |
| Polymerization inhibitor | Q-1301 | 0.003 g (6 μmol) | 0.003 g (6 μmol) | 0.003 g (6 μmol) | 0.003 g (6 μmol) | 0.003 g (6 μmol) |
| Hydrolysis | Stirring time taken until the solution becomes homogenous and clear solution | 1 h | 1 h | 0.5 h | 0.5 h | 0.5 h |
| Storage stability of composition | Number of days taken until the composition becomes gel | 6 | 7 | 7 | 7 | Equal to or greater than 30 |
| Solvent resistance of cured film | Immersion in acetone | ○ | ○ | ○ | ○ | ○ |
| Pencil hardness | Load 0.75 kg | 6H | 6H | 6H | 6H | 6H |
| Abrasion resistance test | Steel wool #0000 | No scratch | No scratch | No scratch | No scratch | No scratch |

As is evident from the results of Examples 7 to 11 in Table 17, it was understood that even though the amount of (A) compound having a carbonyl group generating a radical by photoirradiation and a carboxyl group decarboxylated by photoirradiation used and the amount of (E) compound having a carbonyl group generating a radical by photoirradiation and a group generating a base by being decarboxylated by photoirradiation used are changed, a crosslinked product (resin) having excellent solvent resistance and high hardness is rapidly and efficiently obtained. In addition, it was understood that the composition of Example 11 has high storage stability.

TABLE 18

|  |  | Example 12 | Example 13 | Example 14 |
|---|---|---|---|---|
| Compound (A) | 1-B9 | 0.025 g (0.08 mmol) |  | 0.025 g (0.08 mmol) |
| Compound (E) | 4-4 | 0.05 g (0.095 mmol) |  |  |
|  | 4-6 |  |  | 0.038 g (0.08 mmol) |
| Compound (A/E) | 4-8 |  | 0.05 g (0.087 mmol) |  |
| Silane coupling agent (B) | (3-Mercaptopropyl)trimethoxysilane | 1.96 g (10 mmol) | 1.96 g (10 mmol) | 1.96 g (10 mmol) |
| (C) Water | Deionized water | 0.27 g (15 mmol) | 0.27 g (15 mmol) | 0.27 g (15 mmol) |
| Organic solvent | Methanol | 0.1 g | — | 0.1 g |
| Compound (F) | TAOT | 0.79 g (3 mmol) | 0.79 g (3 mmol) | 0.79 g (3 mmol) |
| Polymerization inhibitor | Q-1301 | 0.003 g (6 μmol) | 0.003 g (6 μmol) | 0.003 g (6 μmol) |
| UV absorber | TINUVIN-900 | 0.04 g (89 μmol) | 0.04 g (89 μmol) | 0.04 g (89 μmol) |
| Hydrolysis | Stirring time taken until the solution becomes homogenous and clear solution | 1 h | 1 h | 1 h |
| Storage stability of composition | Number of days taken until the composition becomes gel | Equal to or greater than 30 | Equal to or greater than 30 | 12 |
| Solvent resistance of cured film | Immersion in acetone | ○ | ○ | ○ |
| Pencil hardness | Load 0.75 kg | 6 H | 6 H | 6 H |
| Abrasion resistance test | Steel wool #0000 | No scratch | No scratch | No scratch |

As is evident from the results of Examples 12 to 14 in Table 18, it was understood that even in a case where the curing system in the photocuring method of the present invention contains a UV absorber which may hinder the absorption of ultraviolet rays (UV), by using the compound (A) having a thioxanthone skeleton and the compound (E) or the compound (A/E) and performing irradiation of light (active energy rays) having a wavelength of 365 nm or 405 nm thereon, a crosslinked product (resin) containing a constitutional unit derived from the silane compound (D) is obtained. In addition, it was understood that in a case where the compound (A/E) is used instead of the combination of the compound (A) and the compound (E) in the photocuring method of the present invention, a crosslinked product (resin) is obtained by adding small amount of the compound (A/E).

Examples 15 to 18: Photocuring Method by Sol-Gel Reaction and Yne-Thiol Reaction Through Irradiation of Light (Active Energy Rays)

Deionized water and methanol, which is used if necessary, were added to a solution containing either (A) compound having a carbonyl group generating a radical by photoirradiation and a carboxyl group decarboxylated by photoirradiation and (E) compound having a carbonyl group generating a radical by photoirradiation and a group generating a base by being decarboxylated by photoirradiation or (A/E) compound having a carbonyl group generating a radical by photoirradiation, a carboxyl group decarboxylated by photoirradiation, and a group generating a base by being decarboxylated by photoirradiation and (3-mercaptopropyl) trimethoxysilane (manufactured by Wako Pure Chemical Industries, Ltd.). The solution was stirred for a certain period of time at room temperature until the solution became a homogeneous and clear solution. After cloudiness resulting from water disappeared and the solution became clear, (F) compound having at least two or more polymerizable unsaturated groups and various additive (polymerization inhibitor or/and UV absorber), which are used if necessary, were added thereto and mixed together again, and an alcohol generated as a side product by hydrolysis was concentrated under reduced pressure at room temperature (in addition, the number of days taken for the mixed composition to become in a state of gel that cannot be taken out of a container in a case where the composition is stored at room temperature in a sealed.light blocking state was measured). Thereafter, a coating film was prepared by coating a glass substrate with the concentrate (composition) by means of bar coating, and by using an ultraviolet irradiation light source device having a specific exposure intensity with respect to the coating film, that is, REX-250 (manufactured by Asahi Spectra Co., Ltd.), the coating film was cured by being irradiated with light (active energy rays) having a wavelength of 365 nm without using a filter such that the cumulative exposure amount became 1.0 J. The cured coating film (cured film) was immersed in acetone for 30 seconds, and whether the film was dissolved or peeled was checked. In a case where the cured film was not dissolved and peeled even being immersed in acetone, the film was evaluated as "Solvent resistance: ○", and in a case where the cured film had insufficient hardness and was dissolved in acetone or peeled, the film was evaluated as "Solvent resistance: X". The evaluation results are shown in Table 19.

TABLE 19

|  |  | Example 15 | Example 16 | Example 17 | Example 18 |
|---|---|---|---|---|---|
| Compound (A) | 1-A2 | 0.025 g (0.10 mmol) | | | |
|  | 1-B2 | | 0.025 g (0.09 mmol) | | |
|  | 1-B9 | | | 0.025 g (0.08 mmol) | |
| Compound (E) | 4-1 | 0.05 g (0.10 mmol) | | | |
|  | 4-2 | | 0.05 g (0.098 mmol) | | |
|  | 4-4 | | | 0.05 g (0.095 mmol) | |
| Compound (A/E) | 4-8 | | | | 0.05 g (0.087 mmol) |
| Silane coupling agent (B) | (3-Mercaptopropyl)trimethoxysilane | 1.96 g (10 mmol) | 1.96 g (10 mmol) | 1.96 g (10 mmol) | 1.96 g (10 mmol) |
| (C) Water | Deionized water | 0.27 g (15 mmol) | 0.27 g (15 mmol) | 0.27 g (16 mmol) | 0.27 g (15 mmol) |
| Organic solvent | Methanol | — | 0.1 g | 0.1 g | — |
| Compound (F) | TPOP | 0.40 g (3 mmol) | 0.40 g (3 mmol) | 0.40 g (3 mmol) | 0.40 g (3 mmol) |
| Polymerization inhibitor | Q-1301 | 0.003 g (6 μmol) | 0.003 g (6 μmol) | 0.003 g (6 μmol) | 0.003 g (6 μmol) |
| Hydrolysis | Stirring time taken until the solution becomes homogenous and clear solution | 0.5 h | 1 h | 1 h | 1 h |
| Storage stability of composition | Number of days taken until the composition becomes gel | Equal to or greater than 30 | Equal to or greater than 30 | Equal to or greater than 30 | Equal to or greater than 30 |
| Solvent resistance of cured film | Immersion in acetone | ○ | ○ | ○ | ○ |

As is evident from the results of Examples 15 to 18 in Table 19, even in a case where a compound having a triple bond was used as (F) compound having two or more polymerizable unsaturated groups, a crosslinked product (resin) containing a constitutional unit derived from the silane compound (D) was rapidly and efficiently obtained. It was understood that, therefore, the photocuring method of the present invention can be applied to a curing system in which the sol-gel reaction and the yne-thiol reaction are combined.

Examples 19 and 20 and Comparative Examples 3 and 4: Photocuring Method by Sol-Gel Reaction and Radical Polymerization Reaction Through Irradiation of Light (Active Energy Rays)

Deionized water was added to a solution containing (A) compound having a carbonyl group generating a radical by photoirradiation and a carboxyl group decarboxylated by photoirradiation or a carboxylic acid represented by the following formula [101] or [102], (E) compound having a carbonyl group generating a radical by photoirradiation and a group generating a base by being decarboxylated by photoirradiation or a photobase generator represented by the following formula [103] or [104], or (A/E) compound having a carbonyl group generating a radical by photoirradiation, a carboxyl group decarboxylated by photoirradiation, and a group generating a base by being decarboxylated by photoirradiation, and (3-acryloxy)propyltrimethoxysilane (manufactured by TOKYO CHEMICAL INDUSTRY CO., LTD.). The solution was stirred for a certain period of time at room temperature until the solution became a homogeneous and clear solution. After cloudiness resulting from water disappeared and the solution became clear, an alcohol generated as a side product by hydrolysis was concentrated under reduced pressure at room temperature (in addition, the number of days taken for the mixed composition to become in a state of gel that cannot be taken out of a container in a case where the composition is stored at room temperature in a sealed.light blocking state was measured). Thereafter, a coating film was prepared by coating a glass substrate with the concentrate (composition) by means of bar coating, and by using an ultraviolet irradiation light source device having a specific exposure intensity with respect to the coating film, that is, REX-250 (manufactured by Asahi Spectra Co., Ltd.), the coating film was cured by being irradiated with light (active energy rays) having a wavelength of 365 nm under a nitrogen stream without using a filter such that the cumulative exposure amount became 1.0 J. The cured coating film (cured film) was immersed in acetone for 30 seconds, and whether the film was dissolved or peeled was checked. In a case where the cured film was not dissolved and peeled even being immersed in acetone, the film was evaluated as "Solvent resistance: ○", and in a case where the cured film had insufficient hardness and was dissolved in acetone or peeled, the film was evaluated as "Solvent resistance: X". In addition, pencil hardness and abrasion resistance were evaluated by performing a pencil hardness test (JIS K5600-5-4) and an abrasion resistance test (the film was rubbed back and forth 10 times with #0000 steel wool manufactured by BONSTAR SALES Co., Ltd., and then the scratches were visually checked) on the cured film. The evaluation results are shown in Table 20. It should be noted that the structural formulae of the carboxylic acids represented by the formula [101] and [102] and the photobase generators represented by the formulae [103] and [104] are shown below.

Carboxylic Acids: Formula [101] and Formula [102]:

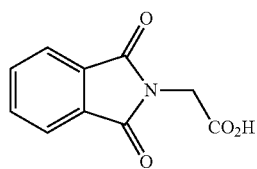

[101]

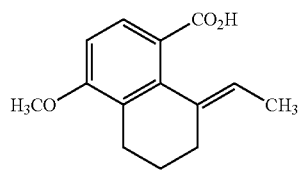

[102]

Photobase Generators: Formula [103] and Formula [104]:

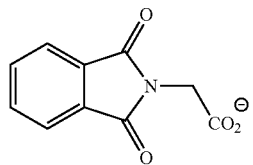

[103]

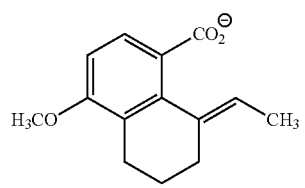

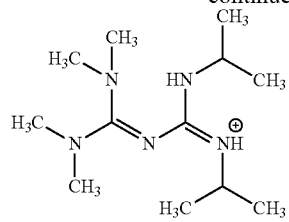

[104]

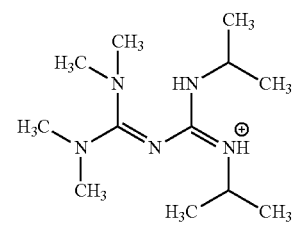

TABLE 20

|  |  | Example 19 | Example 20 | Comparative Example 3 | Comparative Example 4 |
|---|---|---|---|---|---|
| Compound (A) | 1-A2 | 0.1 g (0.40 mmol) |  |  |  |
| Carboxylic acid | 101 |  |  | 0.08 g (0.40 mmol) |  |
|  | 102 |  |  |  | 0.09 g (0.40 mmol) |
| Compound (E) | 4-1 | 0.15 g (0.30 mmol) |  |  |  |
| Photobase generator | 103 |  |  | 0.13 g (0.30 mmol) |  |
|  | 104 |  |  |  | 0.14 g (0.30 mmol) |
| Compound (A/E) | 4-8 |  | 0.17 g (0.30 mmol) |  |  |
| Silane coupling agent (B) | 3-(Acryloxy)propyltrimethoxysilane | 2.34 g (10 mmol) | 2.34 g (10 mmol) | 2.34 g (10 mmol) | 2.34 g (10 mmol) |
| (C) Water | Deionized water | 0.52 g (30 mmol) | 0.52 g (30 mmol) | 0.52 g (30 mmol) | 0.52 g (30 mmol) |
| Hydrolysis | Stirring time taken until the solution becomes homogenous and clear solution | 1 h | 2 h | 1 h | 1 h |
| Storage stability of composition | Number of days taken until the composition becomes gel | Equal to or greater than 30 | Equal to or greater than 30 | Equal to or greater than 30 | Equal to or greater than 30 |
| Solvent resistance of cured film | Immersion in acetone | ○ | ○ | x | x |
| Pencil hardness | Load 0.75 kg | 6 H | 6 H | — | — |
| Abrasion resistance test | Steel wool #0000 | No scratch | No scratch | — | — |

As is evident from the results of Examples 19 and 20 in Table 20, even in a case where a silane coupling agent having a (meth)acryl group was used as the silane coupling agent (D), a crosslinked product (resin) containing a constitutional unit derived from the silane compound (D) was rapidly and efficiently obtained. It was understood that, therefore, the photocuring method of the present invention can be applied to a curing system in which the sol-gel reaction and the radical polymerization reaction are combined. In contrast, as is evident from the results of Comparative Examples 3 and 4, it was understood that in a case where a carboxylic acid, which does not have a functional group being able to generate a radical by the irradiation of light (active energy rays), or a photobase generator, which does not have a functional group being able to generate a radical by the irradiation of light (active energy rays), is used, a crosslinked product (resin) is not obtained. That is, it was understood that for obtaining a crosslinked product (resin) by using a silane coupling agent having a (meth)acryl group, a curing system in which the sol-gel reaction and the radical polymerization reaction simultaneously proceed is important.

Examples 21 and 22: Photocuring Method by Sol-Gel Reaction and Ene-Thiol Reaction Through Irradiation of Light (Active Energy Rays) by Using Colloidal Silica as Filler SNOWTEX O (registered trademark) (manufactured by NISSAN CHEMICAL INDUSTRIES, LTD., content of amorphous silica: 20%, content of water: 80%, particle diameter: 10 to 15 nm) was added to a solution containing (A) compound having a carbonyl group generating a radical by photoirradiation and a carboxyl group decarboxylated by photoirradiation, (E) compound having a carbonyl group generating a radical by photoirradiation and a group generating a base by being decarboxylated by photoirradiation, and (3-mercaptopropyl)trimethoxysilane (manufactured by Wako Pure Chemical Industries, Ltd.). The solution was stirred for 1 hour at room temperature and then for 1 hour at 80° C. After cloudiness disappeared, (F) compound having two or more polymerizable unsaturated groups were added thereto and mixed together again, and an alcohol generated as a side product by hydrolysis was concentrated under reduced pressure at room temperature. Thereafter, a coating film was prepared by coating a glass substrate with the concentrate (composition) by means of bar coating, and by using an ultraviolet irradiation light source device having a specific exposure intensity with respect to the coating film, that is, REX-250 (manufactured by Asahi Spectra Co., Ltd.), the coating film was cured by being irradiated with light (active energy rays) having a wavelength of 365 nm under a nitrogen stream without using a filter such that the cumulative exposure amount became 1.0 J. The cured coating film (cured film) was immersed in acetone for 30 seconds, and whether the film was dissolved or peeled was checked. In a case where the cured film was not dissolved and peeled even being immersed in acetone, the film was evaluated as "Solvent resistance: ○", and in a case where the cured film had insufficient hardness and was dissolved in acetone or peeled, the film was evaluated as "Solvent resistance: X". In addition, pencil hardness and abrasion resistance were evaluated by performing a pencil hardness test (JIS K5600-5-4) and an abrasion resistance test (the film was rubbed back and forth 10 times with #0000 steel wool manufactured by BONSTAR SALES Co., Ltd., and then the scratches were visually checked) on the cured film. The evaluation results are shown in Table 21.

TABLE 21

| | | Example 21 | Example 22 |
|---|---|---|---|
| Compound (A) | 1-A2 | 0.05 g (0.20 mmol) | |
| | 1-C11 | | 0.05 g (0.19 mmol) |
| Compound (E) | 4-1 | 0.15 g (0.30 mmol) | |
| | 4-7 | | 0.15 g (0.28 mmol) |
| Silane coupling agent (B) | (3-Mercaptopropyl)trimethoxysilane | 1.98 g (10 mmol) | 1.98 g (10 mmol) |
| (C) Water | Water contained in SNOWTEX O | 0.27 g (15 mmol) | 0.27 g (15 mmol) |
| Compound (F) | TAOT | 0.82 g (3.3 mmol) | 0.82 g (3.3 mmol) |
| Filler | Colloidal silica ($SiO_2$ component in SNOWTEX O) | 0.07 g | 0.07 g |
| Solvent resistance of cured film | Immersion in acetone | ○ | ○ |
| Pencil hardness | Load 0.75 kg | 7 H | 7 H |
| Abrasion resistance test | Steel wool #0000 | No scratch | No scratch |

As is evident from the results of Examples 21 and 22 in Table 21, it was understood that even though colloidal silica having a particle diameter of 10 to 15 nm is added as a filler, a crosslinked product (resin) containing a constitutional unit derived from the silane compound (D) is rapidly and efficiently obtained. In addition, it was understood that the obtained crosslinked product (resin) has hardness higher than that of the crosslinked products (resins) of Examples 4 to 20. Generally, in a case where a filler having a particle diameter larger than 50 nm is used, cloudiness occurs, and light-transmitting properties are lost. However, it was understood that in the curing system in the photocuring method of the present invention, even in a case where the resin composition contains a filler, a transparent crosslinked product (resin) is obtained.

Examples 23 to 27: Photocuring Method by Sol-Gel Reaction and Ene-Thiol Reaction Through Irradiation of Light (Active Energy Rays) by Using Aluminum Nitride as Filler Deionized water was added to a solution containing (A) compound having a carbonyl group generating a radical by photoirradiation and a carboxyl group decarboxylated by photoirradiation, (E) compound having a carbonyl group generating a radical by photoirradiation and a group generating a base by being decarboxylated by photoirradiation, and (3-mercaptopropyl)trimethoxysilane (manufactured by Wako Pure Chemical Industries, Ltd.), and the solution was stirred for 30 minutes, thereby preparing sol. Thereafter, the sol prepared as above was added to a composition, which was obtained by adding 2,4,6-tris(allyloxy)-1,3,5-triazine and aluminum nitride to an ethyl lactate solution containing PVP-K25 as a dispersant, and the mixture was kneaded for 120 minutes at a rotation speed of 300 rpm by using a planetary ball mill P-6 (manufactured by Fritsch Japan Co., Ltd), thereby preparing a resin composition. Then, a coating film was prepared by coating an aluminum plate with the composition prepared as above by means of bar coating, and then the coating film was pre-baked at 150° C. Subsequently, by using an ultraviolet irradiation light source device having a specific exposure intensity with respect to the coating film, that is, HLR-100-2 (manufactured by SEN LIGHTS Co., Ltd.), the coating film was cured by being irradiated with light for 1 minute at a surface illuminance of 254 nm=9 mW/cm$^2$ and 365 nm=11 mW/cm$^2$ without using a filter. The coating was then further heated for 5 minutes at 150° C., thereby obtaining a cured film having a film thickness of 10 to 40 μm. Various physical properties of the obtained cured film were evaluated by the following evaluation methods. The evaluation results are shown in Table 22. It should be noted that the names and the suppliers of the aluminum nitride and the dispersant used in Table 22 are shown below.

Aluminum Nitride (AlN):

Toyalnite JC (registered trademark): average particle diameter of 1.2 μm (manufactured by Toyo Aluminum K. K.)

AlN020SF: average particle diameter of 2.1 μm (manufactured by THRUTEK APPLIED MATERIALS)

TFZ-A02P: average particle diameter of 1.5 μm (manufactured by Toyo Aluminum K. K.)

TFZ-A15P: average particle diameter of 15.0 μm (manufactured by Toyo Aluminum K. K.)

Dispersant:

PVP-K25: polyvinyl pyrrolidone (manufactured by Wako Pure Chemical Industries, Ltd.)

Method for Evaluating Various Physical Properties of Cured Film

[Solvent Resistance]

The cured film was immersed in each of three kinds of solvents including acetone, methanol, and methyl ethyl ketone for 30 seconds, and whether the film was dissolved or peeled was checked. In a case where the cured film was immersed in each of the three kinds of solvents including acetone, methanol, and methyl ethyl ketone, and the cured film was not dissolved and peeled in any of the solvents, the cured film was evaluated as "Solvent resistance: ○". In a case where the cured film had insufficient hardness and was dissolved or peeled, the cured film was evaluated as "Solvent resistance: X".

[Pencil Hardness]

Pencils with hardness of B to 9H were sharpened such that the pencil lead became flat. Each of the pencils was loaded on a scratch hardness tester (KT-VF 2380), the pencil lead of the pencil was pressed on the cured film at an angle of about 45° with respect to the film, and the hardness of the pencil at the point in time when the cured film was not peeled was recorded (JIS K5600-5-4, load: 0.75 kg).

[Crosscut Test]

The cured film was scored with a cutter knife such that the knife reached the base material, thereby making cuts in the form of grids at an interval of 1 mm (100 meshes). Then, a pressure sensitive adhesive tape with a length of about 50 mm was stuck to the cured film cut in the form of grids, and the top of the pressure sensitive adhesive tape was rubbed with an eraser such that the tape was attached to the cured film. After 1 to 2 minutes, the end of the tape was held, the tape was instantaneously peeled in a state where the angle between the tape and the surface of the cured film was being kept at 90°, and the peeling of the cured film was evaluated. In a case where the cured film was not peeled at all, the film was evaluated as "Adhesiveness: ○", and in a case where a portion of the cured film was peeled, the film was evaluated as "Adhesiveness: X".

[Volume Resistivity (Electrical Insulating Properties)]

The volume resistivity (electrical insulating properties) of the cured film prepared on an aluminum plate having a size of 5 cm (width)×5 cm×1.0 mm (thickness) was measured using a multipurpose high resistivity meter which is a meter based on JIS K6911, that is, HIRESTA UX MCP-HT800 (manufactured by Mitsubishi Chemical Corporation) (measurement range: $9.99 \times 10^4$ to $1.0 \times 10^{14} \Omega$, applied voltage: 500 V).

[Thermal Conductivity]

By using a cylindrical silicon mold, a circular cured film having a size of 5 mm (width)×1 mm (thickness) was prepared from the resin composition under the same conditions as those in examples, and the surface thereof was treated with graphite. Then, by accurately measuring the thickness (to 3 places of decimals), the diameter (to 3 places of decimals), and the weight (to 4 places of decimals) thereof, the specific gravity of the film was calculated. By using a thermophysical property measuring device adopting a xenon laser flash method, that is, LFA-502 (manufactured by TOKYO ELECTRONICS MANUFACTURING CO., LTD.), a thermal diffusivity and specific heat were determined (based on the testing method for thermal diffusivity.specific heat capacity in JIS R1611-2010 "Measurement methods of thermal diffusivity.specific heat capacity.thermal conductivity for fine ceramics by flash method" and JIS 7810-2005 "Thermal diffusivity measurement using metal laser flash method"). The thermal conductivity was calculated by multiplying the obtained thermal diffusivity, specific gravity, and specific heat together.

photoirradiation and a carboxyl group decarboxylated by photoirradiation, (E) compound having a carbonyl group generating a radical by photoirradiation and a group generating a base by being decarboxylated by photoirradiation or

TABLE 22

| | | Example 23 | Example 24 | Example 25 | Example 26 | Example 27 |
|---|---|---|---|---|---|---|
| Compound (A) | 1-A2 | 0.05 g (0.20 mmol) | 0.05 g (0.20 mmol) | 0.05 g (0.20 mmol) | 0.05 g (0.20 mmol) | 0.05 g (0.20 mmol) |
| Compound (E) | 4-1 | 0.15 g (0.30 mmol) | 0.15 g (0.30 mmol) | 0.15 g (0.30 mmol) | 0.15 g (0.30 mmol) | 0.15 g (0.30 mmol) |
| Silane coupling agent (B) | (3-Mercaptopropyl)trimethoxysilane | 1.98 g (10 mmol) | 1.98 g (10 mmol) | 1.98 g (10 mmol) | 1.98 g (10 mmol) | 1.98 g (10 mmol) |
| (C) Water | Deionized water | 0.27 g (15 mmol) | 0.27 g (15 mmol) | 0.27 g (15 mmol) | 0.27 g (15 mmol) | 0.27 g (15 mmol) |
| Organic solvent | Ethyl lactate | 3 g | 3 g | 3 g | 3 g | 3 g |
| Compound (F) | TAOT | 0.82 g (3.3 mmol) | 0.82 g (3.3 mmol) | 0.82 g (3.3 mmol) | 0.82 g (3.3 mmol) | 0.82 g (3.3 mmol) |
| Filler | AlN Toyalnite JC | 12 g (292 mmol) | | | | |
| | AlN AlN020SF | | 12 g (292 mmol) | | | |
| | AlN TFZ-A02P | | | 12 g (292 mmol) | | 8.6 g (209 mmol) |
| | AlN TFZ-A15P | | | | 12 g (292 mmol) | 3.4 g (82 mmol) |
| Dispersant | PVP-25K | 0.12 g | 0.12 g | 0.12 g | 0.12 g | 0.12 g |
| Solvent resistance of cured film | Immersion in solvent | ○ | ○ | ○ | ○ | ○ |
| Pencil hardness | Load 0.75 kg | 4H | 4H | 4H | 2H | 2H |
| Adhesiveness of cured film | Crosscut test | ○ | ○ | ○ | ○ | ○ |
| Electrical insulating properties of cured film | Volume resistivity Ω · cm | $1.0 \times 10^{14}$ | $2.2 \times 10^{12}$ | $1.0 \times 10^{14}$ | $1.0 \times 10^{14}$ | $1.0 \times 10^{14}$ |
| Thermal conductivity of cured film | Thermal conductivity W/m × K | 1.08 | 0.85 | 1.33 | 0.71 | 1.42 |

As is evident from the results of Examples 23 to 27 in Table 22, it was understood that even though a large amount of the filler such as aluminum nitride which does not easily transmit ultraviolet rays (UV) is added as a filler, a crosslinked product (resin) containing a constitutional unit derived from the silane compound (D) is rapidly and efficiently obtained. The results imply that because the radical generated by the irradiation of light (active energy rays) is hardly deactivated by the ene-thiol reaction, even though the curing system contains a large amount of filler which has a large particle diameter and does not easily transmit light, the ene-thiol reaction can effectively function. In addition, it was understood that because the obtained crosslinked product (resin) uses a silane coupling agent having a mercapto group as a raw material, the adhesiveness between the fillers or the adhesiveness of aluminum or the like with respect to a metal substrate is high. Furthermore, it was understood that the addition of aluminum nitride improves the thermal conductivity of the crosslinked product (resin). Moreover, as is evident from the results of Example 27, in a case where a mixture, which is obtained by mixing together fillers having a large particle diameter and a small particle diameter at any ratio, is added as a filler, the thermal conductivity is greatly improved.

Examples 28 and 29: Photocuring Method by Sol-Gel Reaction and Ene-Thiol Reaction Through Irradiation of Light (Active Energy Rays) of Long-Wavelength Range by Using Aluminum Nitride as Filler Deionized water was added to a solution containing (A) compound having a carbonyl group generating a radical by photoirradiation and a carboxyl group decarboxylated by photoirradiation, (E) compound having a carbonyl group generating a radical by photoirradiation and a group generating a base by being decarboxylated by photoirradiation or (A/E) compound having a carbonyl group generating a radical by photoirradiation, a carboxyl group decarboxylated by photoirradiation, and a group generating a base by being decarboxylated by photoirradiation, and (3-mercaptopropyl)trimethoxysilane (manufactured by Wako Pure Chemical Industries, Ltd.), and the solution was stirred for 30 minutes, thereby preparing sol. Thereafter, the sol prepared as above was added to a composition, which was obtained by adding 2,4,6-tris(allyloxy)-1,3,5-triazine and aluminum nitride to an ethyl lactate solution containing PVP-K25 as a dispersant, and the mixture was kneaded for 120 minutes at a rotation speed of 300 rpm by using a planetary ball mill P-6 (manufactured by Fritsch Japan Co., Ltd), thereby preparing a resin composition. Then, a coating film was prepared by coating an aluminum plate with the composition prepared as above by means of bar coating, and then the coating film was pre-baked at 150° C. Subsequently, by using an ultraviolet irradiation light source device having a specific exposure intensity with respect to the coating film, that is, "UV-LED desktop batch-type UV curing device MUVBA-0.3×0.3×0.5 (manufactured by AITEC SYSTEM Co., Ltd.)", the coating film was cured by being irradiated with light for 30 seconds at a surface illuminance of 365 nm=180 mW/cm$^2$ or 405 nm=110 mW/cm$^2$. The coating film was then further heated for 5 minutes at 150° C., thereby obtaining a cured film having a film thickness of 10 to 20 μm. Various physical properties of the obtained cured film obtained by photoirradiation under the condition of a surface illuminance of 365 nm=180 mW/cm$^2$ among the obtained cured films were evaluated in terms of three items of "solvent resistance", "pencil hardness", and "adhesiveness" based on the evaluation methods of Examples 23 to 27. The evaluation results are shown in Table 23.

TABLE 23

|  |  | Example 28 | Example 29 |
|---|---|---|---|
| Compound (A) | 1-B3 | 0.05 g (0.18 mmol) |  |
| Compound (E) | 4-3 | 0.15 g (0.29 mmol) |  |
| Compound (A/E) | 4-8 |  | 0.17 g (0.30 mmol) |
| Silane coupling agent (B) | (3-Mercaptopropyl)trimethoxysilane | 1.98 g (10 mmol) | 1.98 g (10 mmol) |
| (C) Water | Deionized water | 0.27 g (15 mmol) | 0.27 g (15 mmol) |
| Organic solvent | Ethyl lactate | 3 g | 3 g |
| Compound (F) | TAOT | 0.82 g (3.3 mmol) | 0.82 g (3.3 mmol) |
| Filler | AlN Toyalnite JC | 12 g (292 mmol) | 12 g (292 mmol) |
| Dispersant | PVP-25K | 0.12 g | 0.12 g |
| Photosensitivity at 365 nm | 365 nm UV-LED | ○ | ○ |
| Photosensitivity at 405 nm | 405 nm UV-LED | ○ | ○ |
| Solvent resistance of cured film | Immersion in solvent | ○ | ○ |
| Pencil hardness | Load 0.75 kg | 4H | 4H |
| Adhesiveness of cured film | Crosscut test | ○ | ○ |

As is evident from the results of Examples 28 and 29 in Table 23, it was understood that the photocuring method of the present invention can be applied to the curing system of a resin composition containing a large amount of filler even though UV-LED having a single emission line at 365 nm or 405 nm is used as a source of light (active energy rays).

Examples 30 to 33: Photocuring Method by Sol-Gel Reaction and Ene-Thiol Reaction Through Irradiation of Light (Active Energy Rays) Using Silane Coupling Agent in Combination Deionized water was added to a solution containing (A) compound having a carbonyl group generating a radical by photoirradiation and a carboxyl group decarboxylated by photoirradiation and (E) compound having a carbonyl group generating a radical by photoirradiation and a group generating a base by being decarboxylated by photoirradiation or (A/E) compound having a carbonyl group generating a radical by photoirradiation, a carboxyl group decarboxylated by photoirradiation, and a group generating a base by being decarboxylated by photoirradiation, (3-mercaptopropyl)trimethoxysilane (manufactured by Wako Pure Chemical Industries, Ltd.), and a silane coupling agent shown in Table 27, and the solution was stirred for 30 minutes, thereby preparing sol. Thereafter, the sol prepared as above was added to a composition, which was obtained by adding 2,4,6-tris(allyloxy)-1,3,5-triazine and aluminum nitride to an ethyl lactate solution containing PVP-K25 as a dispersant, and the mixture was kneaded for 120 minutes at a rotation speed of 300 rpm by using a planetary ball mill P-6 (manufactured by Fritsch Japan Co., Ltd), thereby preparing a resin composition. Then, a coating film was prepared by coating an aluminum plate with the composition prepared as above by means of bar coating, and then the coating film was pre-baked at 150° C. Subsequently, by using an ultraviolet irradiation light source device having a specific exposure intensity with respect to the coating film, that is, HLR-100-2 (manufactured by SEN LIGHTS Co., Ltd.), the coating film was cured by being irradiated with light for 1 minute at a surface illuminance of 254 nm=9 mW/cm$^2$ and 365 nm=11 mW/cm$^2$ without using a filter. The coating was then further heated for 5 minutes at 150° C., thereby obtaining a cured film having a film thickness of 10 to 20 μm. Various physical properties of the obtained cured film obtained by photoirradiation were evaluated in terms of four items of "solvent resistance", "pencil hardness", "adhesiveness", and "thermal conductivity" based on the evaluation methods of Examples 23 to 27. The evaluation results are shown in Table 24.

TABLE 24

|  |  | Example 30 | Example 31 | Example 32 | Example 33 |
|---|---|---|---|---|---|
| Compound (A) | 1-A2 | 0.05 g (0.20 mmol) | 0.05 g (0.20 mmol) | 0.05 g (0.20 mmol) | 0.05 g (0.20 mmol) |
| Compound (E) | 4-1 | 0.15 g (0.30 mmol) | 0.15 g (0.30 mmol) | 0.15 g (0.30 mmol) | 0.15 g (0.30 mmol) |
| Silane coupling agent (B) | (3-Mercaptopropyl)trimethoxysilane | 1.17 g (6.0 mmol) | 1.17 g (6.0 mmol) | 0.98 g (5.0 mmol) | 1.17 g (6.0 mmol) |
|  | 3-(Methacryloxy)propyltrimethoxysilane |  |  | 1.24 g (5.0 mmol) |  |
| Silane monomer | Methyltrimethoxysilane | 0.54 g (4.0 mmol) |  |  |  |
|  | Vinyltrimethoxysilane |  | 0.74 g (4.0 mmol) |  |  |
|  | Tetraethoxysilane |  |  |  | 0.62 g (3.0 mmol) |

TABLE 24-continued

|  |  | Example 30 | Example 31 | Example 32 | Example 33 |
|---|---|---|---|---|---|
| (C) Water | Deionized water | 0.27 g (15 mmol) | 0.27 g (15 mmol) | 0.27 g (15 mmol) | 0.27 g (15 mmol) |
| Organic solvent | Ethyl lactate | 3 g | 3 g | 3 g | 3 g |
| Compound (F) | TAOT | 0.49 g (2.0 mmol) | 0.49 g (2.0 mmol) |  | 0.49 g (2.0 mmol) |
| Filler | AlN | 12 g | 12 g | 12 g | 12 g |
|  | Toyalnite JC | (292 mmol) | (292 mmol) | (292 mmol) | (292 mmol) |
| Dispersant | PVP-25K | 0.12 g | 0.12 g | 0.12 g | 0.12 g |
| Solvent resistance of cured film | Immersion in solvent | ○ | ○ | ○ | ○ |
| Pencil hardness | Load 0.75 kg | 4 H | 4 H | 2 H | 4 H |
| Adhesiveness of cured film | Crosscut test | ○ | ○ | ○ | ○ |
| Thermal conductivity of cured film | Thermal conductivity W/m · K | 1.13 | 1.11 | 0.85 | 1.29 |

As is evident from the results of Examples 30 to 33 in Table 24, it was understood that even though a portion of (3-mercaptopropyl)trimethoxysilane is replaced with various silicon alkoxides described in Examples 30 to 33, a crosslinked product (resin) containing a constitutional unit derived from the silane compound (D) is rapidly and efficiently obtained. In addition, it was understood that the obtained crosslinked product (resin) has a high thermal conductivity. Furthermore, in a case where a metal alkoxide such as tetraethoxysilane having high crosslinking density is used, the thermal conductivity tended to increase.

As is evident from the above results, it was understood that in a case where the sol-gel reaction and the radical polymerization reaction, the ene-thiol reaction, or the yne-thiol reaction are caused to simultaneously proceed by using (A) compound having a carbonyl group generating a radical by photoirradiation and a carboxyl group decarboxylated by photoirradiation and (E) compound having a carbonyl group generating a radical by photoirradiation and a group generating a base by being decarboxylated by photoirradiation in combination, a crosslinked product containing a constitutional unit derived from the silane compound (D) is rapidly and efficiently obtained.

In addition, because the photocuring method of the present invention is a curing system which does not require an alkali metal salt, a problem such as precipitation or whitening of an alkali metal salt caused by the increase in the proportion of organic components used does not occur. Therefore, in the photocuring method of the present invention, by increasing or reducing the amount of organic components used, a crosslinked product (resin) having any film thickness can be prepared. Furthermore, by increasing or reducing the amount of organic components used, the content of inorganic components in the crosslinked product (resin) can be relatively increased or reduced, and various functions can be given to the crosslinked product (resin). In addition, even though the crosslinked product (resin) obtained by the photocuring method of the present invention is used in electronic materials, a problem such as the occurrence of short circuit of metal wiring caused by an alkali metal salt does not occur. Therefore, the crosslinked product (resin) obtained by the photocuring method of the present invention can be used in electronic materials.

INDUSTRIAL APPLICABILITY

The photocuring method of the present invention can cause the pH of a composition containing a silane coupling agent (a silane compound) to shift to an alkaline pH from an acidic pH before and after the irradiation of light (active energy rays), and makes it possible to generate a radical by the irradiation of light (active energy rays). Therefore, it should be noted that the photocuring method of the present invention is a method which makes it possible to rapidly and efficiently obtain a crosslinked product (resin) containing a constitutional unit derived from a silane compound by causing a sol-gel reaction and a radical polymerization reaction, an ene-thiol reaction, or a yne-thiol reaction to simultaneously proceed. Accordingly, the photocuring method of the present invention is useful as a method which makes it possible to rapidly and efficiently obtain a crosslinked product (resin) containing a constitutional unit derived from a silane compound.

The compound represented by the general formula [16] of the present invention is a useful compound (a photo-radical generator) which can function as an acid catalyst even being added in a small amount and can generate a radical by photoirradiation. In addition, the compound represented by the general formula [17] of the present invention is a useful compound which can be "(A/E) compound having a carbonyl group generating a radical by photoirradiation, a carboxyl group decarboxylated by photoirradiation, and a group generating a base by being decarboxylated by photoirradiation" according to the photocuring method of the present invention. It should be noted that the compound represented by the general formula [17] of the present invention is a useful compound (a photobase and photo-radical generator) which can function as a photobase generator even being added in a small amount and can generate a radical by photoirradiation.

The photocuring resin composition of the present invention is a composition which can cause a sol-gel reaction and an ene-thiol reaction, an yne-thiol reaction, or radical polymerization to efficiently proceed in the composition by the irradiation of light (active energy rays) and makes it possible to obtain a crosslinked product (resin) containing a constitutional unit derived from a silane compound. In addition, the photocuring resin composition of the present invention is a useful composition which exhibits high storage stability, can be handled with high stability, does not depend on the film thickness or the humidity of the surrounding environment, and makes it possible to obtain a crosslinked product (resin). Therefore, the photocuring resin composition of the present invention is useful as a resin raw material in optical materials or electronic materials such as paint, printing ink, dental materials, resist, and thermally conductive films.

The invention claimed is:
1. A photocuring method comprising a step 1 and a step 2 performed after the step 1;
wherein in the step 1, in the presence of (A) compound having a carbonyl group generating a radical by photoirradiation and a carboxyl group decarboxylated by photoirradiation, (B) silane coupling agent having a mercapto group or a (meth)acryl group is reacted with (C) water under acidic conditions to obtain (D) silane compound having a mercapto group or a (meth)acryl group and at least one silanol group, and
in the step 2, in the presence of the compound (A) and (E) compound having a carbonyl group generating a radical by photoirradiation and a group generating a base by being decarboxylated by photoirradiation, the compound (A) and the compound (E) are irradiated with light to create alkaline conditions in a reaction system by decarboxylating the carboxyl group of the compound (A) and generating a base from the compound (E), and radicals are generated from the compound (A) and the compound (E) to generate a crosslinked product containing a constitutional unit derived from the silane compound (D) from the silane compound (D) and, from (F) compound having two or more polymerizable unsaturated groups.

2. The photocuring method according to claim 1, wherein the step 1 is performed at a pH in a range of 3 to 5.

3. The photocuring method according to claim 1, wherein the step 2 is performed at a pH in a range of 8 to 14.

4. The photocuring method according to claim 1, wherein the silane coupling agent (B) is (B') silane coupling agent having a mercapto group, the silane compound (D) is (D') silane compound having a mercapto group and at least one silanol group, and the crosslinked product obtained using the compound (F) further contains a constitutional unit derived from the compound (F).

5. The photocuring method according to claim 1, wherein the silane coupling agent (B) is (B") silane coupling agent having a (meth)acryl group, the silane compound (D) is (D") silane compound having a (meth)acryl group and at least one silanol group, and the crosslinked product is obtained by reacting the silane compounds (D") with each other.

6. The photocuring method according to claim 1, wherein the compound (A) and compound (E) are (A/E) compound having a carbonyl group generating a radical by photoirradiation, a carboxyl group decarboxylated by photoirradiation, and a group generating a base by being decarboxylated by photoirradiation.

7. The photocuring method according to claim 1, wherein the compound (A) and the compound (E) are decomposed by light having the same wavelength.

8. The photocuring method according to claim 1, wherein the compound (A) is a compound represented by a general formula [1];

general formula [1]

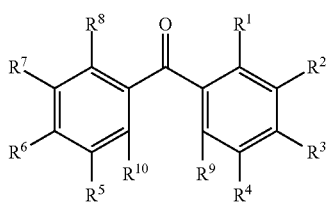

[1]

wherein $R^1$ to $R^8$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^9$ and $R^{10}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^9$ and $R^{10}$ are bonded to each other through an oxygen atom, a sulfur atom, or a carbonyl group, provided that at least one of the groups represented by $R^1$ to $R^8$ is the group represented by the general formula [2];

general formula [2]

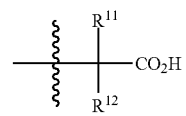

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

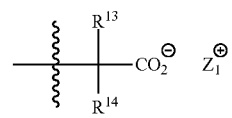

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

9. The photocuring method according to claim 1, wherein the compound (A) is a compound represented by any of general formulae [1-A] to [1-C];

general formula [1-A]

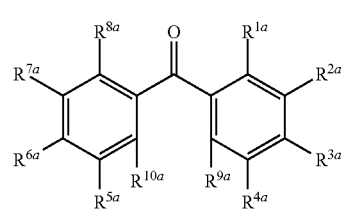

[1-A]

wherein $R^{2a}$, $R^{4a}$, $R^{5a}$, and $R^{7a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^{1a}$, $R^{3a}$, $R^{6a}$, $R^{8a}$, $R^{9a}$, and $R^{10a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of groups represented by $R^{2a}$, $R^{4a}$, $R^{5a}$, and $R^{7a}$ is the group represented by the general formula [2];

general formula [2]

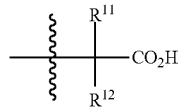

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

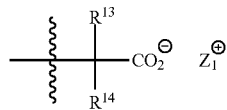

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms;

general formula [1-B]

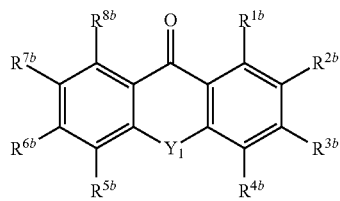

[1-B]

wherein $R^{2b}$, $R^{4b}$, $R^{5b}$ and $R^{7b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{1b}$, $R^{3b}$, $R^{6b}$, and $R^{8b}$ each independently represent a hydrogen atom, and an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, $Y_1$ represents an oxygen atom or a sulfur atom, provided that at least one of the groups represented by $R^{2b}$, $R^{4b}$, $R^{5b}$, and $R^{7b}$ is the group represented by the general formula [2];

general formula [1-C]

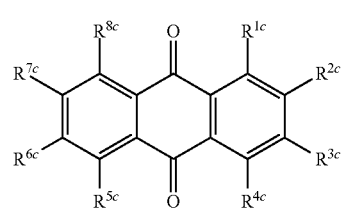

[1-C]

wherein $R^{1c}$ to $R^{8c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{1c}$ to $R^{8c}$ is the group represented by the general formula [2].

10. The photocuring method according to claim 1, wherein the compound (E) is a compound represented by a general formula [4];

general formula [4]

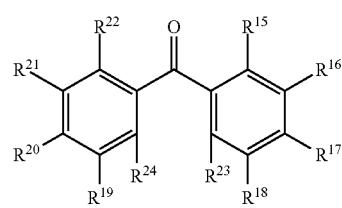

[4]

wherein $R^{15}$ to $R^{22}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^{23}$ and $R^{24}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{23}$ and $R^{24}$ are bonded to each other through an oxygen atom, a sulfur atom, or a carbonyl group, provided that at least one of the groups represented by $R^{15}$ to $R^{22}$ is the group represented by the general formula [3];

general formula [2]

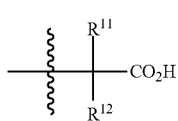

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

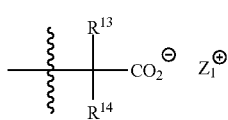

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

11. The photocuring method according to claim 1, wherein the compound (E) is a compound represented by any of general formulae [4-A] to [4-C];

general formula [4-A]

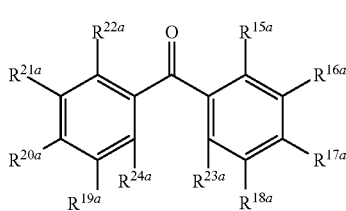

wherein $R^{16a}$, $R^{18a}$, $R^{18a}$, and $R^{21a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^{15a}$, $R^{17a}$, $R^{20a}$, $R^{22a}$, $R^{23a}$ and $R^{24a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of the groups represented by $R^{16a}$, $R^{18a}$, $R^{19a}$, and $R^{21a}$ is the group represented by the general formula [3];

general formula [2]

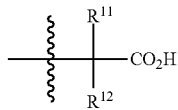

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

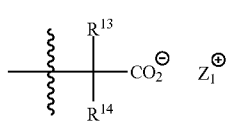

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms;

general formula [4-B]

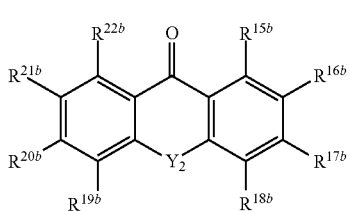

wherein $R^{16b}$, $R^{18b}$, $R^{19b}$, and $R^{21b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{15b}$, $R^{17b}$, $R^{20b}$, and $R^{22b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, $Y_2$ represents an oxygen atom or a sulfur atom, provided that at least one of the groups represented by $R^{16b}$, $R^{18b}$, $R^{19b}$, and $R^{21b}$ is the group represented by the general formula [3];

general formula [4-C]

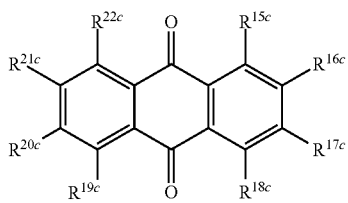

[4-C]

wherein $R^{15c}$ to $R^{22c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{15c}$ to $R^{22c}$ is the group represented by the general formula [3].

12. The photocuring method according to claim 6, wherein the compound (A/E) is a compound represented by a general formula [5];

general formula [5]

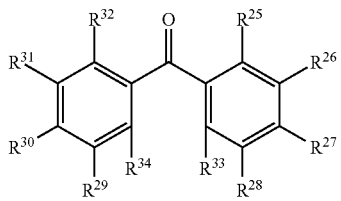

[5]

wherein $R^{25}$ to $R^{32}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^{33}$ and $R^{34}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{33}$ and $R^{34}$ are bonded to each other through an oxygen atom, a sulfur atom, or a carbonyl group, at least one of the groups represented by $R^{25}$ to $R^{32}$ is the group represented by the general formula [2], provided that at least one of the groups represented by $R^{25}$ to $R^{32}$ is the group represented by the general formula [3];

general formula [2]

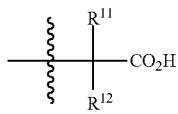

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

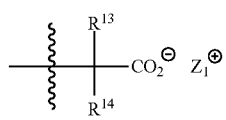

[3]

wherein $Z_1^+$ represents an amidinium cation, a guanidium cation, a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms.

13. A photocuring resin composition comprising (A) compound having a carbonyl group generating a radical by photoirradiation and a carboxyl group decarboxylated by photoirradiation, (D) silane compound having a mercapto group or a (meth)acryl group and at least one silanol group, (E) compound having a carbonyl group generating a radical by photoirradiation and a group generating a base by being decarboxylated by photoirradiation, and (F) compound having at least two polymerizable unsaturated groups.

14. The composition according to claim 13, wherein the silane compound (D) is (D') silane compound having a mercapto group and at least one silanol group.

15. The composition according to claim 13, wherein the silane compound (D) is (D") silane compound having a (meth)acryl group and at least one silanol group.

16. A photocuring resin composition comprising (A) compound having a carbonyl group generating a radical by photoirradiation and a carboxyl group decarboxylated by photoirradiation, (D) silane compound having a mercapto group or a (meth)acryl group and at least one silanol group, and (E) compound having a carbonyl group generating a radical by photoirradiation and a group generating a base by being decarboxylated by photoirradiation, wherein the composition may further comprise (F) compound having at least two polymerizable unsaturated groups,
wherein the compound (E) is a compound represented by a general formula [4];

general formula [4]

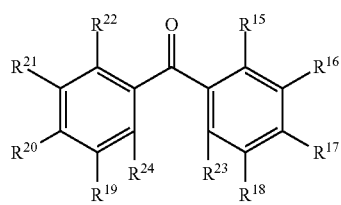

[4]

wherein $R^{15}$ to $R^{22}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^{23}$ and $R^{24}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group; or represent a state where $R^{23}$ and $R^{24}$ are bonded to each other through an oxygen atom, a sulfur atom, or a carbonyl group, provided that at least one of the groups represented by $R^{15}$ to $R^{22}$ is the group represented by the general formula [3];

general formula [2]

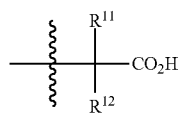

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

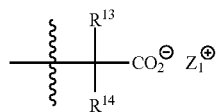

[3]

wherein $Z_1^+$ represents a biguanidinium cation, and $R^{11}$ and $R^{14}$ each independently represent a hydrogen atom, an alkyl group having 1 to 6 carbon atoms, or a hydroxyalkyl group having 1 to 6 carbon atoms.

17. The composition according to claim 16, wherein the compound (E) is a compound represented by any of general formulae [4-A] to [4-C];

general formula [4-A]

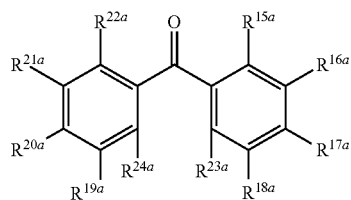

[4-A]

wherein $R^{16a}$, $R^{18a}$, $R^{19a}$, and $R^{21a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, a group represented by a general formula [2], or a group represented by a general formula [3], $R^{15a}$, $R^{17a}$, $R^{20a}$, $R^{22a}$, $R^{23a}$, and $R^{24a}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, provided that at least one of the groups represented by $R^{16a}$, $R^{18a}$, $R^{19a}$, and $R^{21a}$ is the group represented by the general formula [3];

general formula [2]

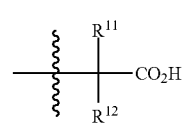

[2]

wherein $R^{11}$ and $R^{12}$ each independently represent a hydrogen atom, an alkyl group having 1 to 6 carbon atoms, or a hydroxyalkyl group having 1 to 6 carbon atoms;

general formula [3]

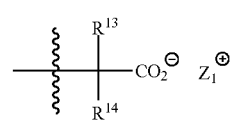

[3]

wherein $Z_1^+$ represents a biguanidinium cation, or a phosphazenium cation, and $R^{13}$ and $R^{14}$ each independently represent a hydrogen atom, an alkyl group having 1 to 6 carbon atoms, or a hydroxyalkyl group having 1 to 6 carbon atoms;

general formula [4-B]

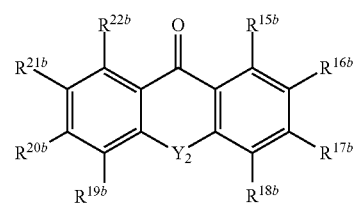

[4-B]

wherein $R^{16b}$, $R^{18b}$, $R^{19b}$, and $R^{21b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], $R^{15b}$, $R^{17b}$, $R^{20b}$, and $R^{22b}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, or a nitro group, $Y_2$ represents an oxygen atom or a sulfur atom, provided that at least one of the groups represented by $R^{16b}$, $R^{18b}$, $R^{19b}$, and $R^{21b}$ is the group represented by the general formula [3];

general formula [4-C]

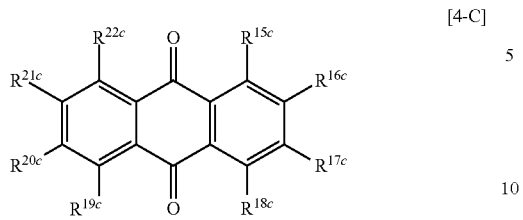

[4-C]

wherein $R^{15c}$ to $R^{22c}$ each independently represent a hydrogen atom, an alkyl group having 1 to 12 carbon atoms, an aryl group having 6 to 14 carbon atoms, an arylalkyl group having 7 to 15 carbon atoms, an alkoxy group having 1 to 12 carbon atoms, a halogen atom, a nitro group, the group represented by the general formula [2], or the group represented by the general formula [3], provided that at least one of the groups represented by $R^{15c}$ to $R^{22c}$ is the group represented by the general formula [3].

18. The composition according to claim 16, wherein the silane compound (D) is (D') silane compound having a mercapto group and at least one silanol group, and the composition includes the compound (F).

19. The composition according to claim 16, wherein the silane compound (D) is (D") silane compound having a (meth)acryl group and at least one silanol group.

* * * * *